United States Patent
Huang et al.

(10) Patent No.: US 8,927,717 B1
(45) Date of Patent: Jan. 6, 2015

(54) THIOCHROMENO[2,3-C]QUINOLIN-12-ONE DERIVATIVES, PREPARATION METHOD AND APPLICATION THEREOF

(71) Applicant: National Defense Medical Center, Taipei (TW)

(72) Inventors: Hsu-Shan Huang, Taipei (TW); Dah-Shyong Yu, Taipei (TW); Tsung-Chih Chen, Nantou County (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 14/180,707

(22) Filed: Feb. 14, 2014

(51) Int. Cl.
C07D 495/04 (2006.01)

(52) U.S. Cl.
CPC .................................. *C07D 495/04* (2013.01)
USPC ......................................... 546/62; 514/228.2

(58) Field of Classification Search
None
See application file for complete search history.

(56) References Cited

PUBLICATIONS

Riepl & Kellermann, 92(4) Helvetica Chimica Acta 668-676 (2009) (CAS Abstract).*

* cited by examiner

*Primary Examiner* — Janet L Andres
*Assistant Examiner* — Timothy R Rozof
(74) *Attorney, Agent, or Firm* — WPAT, P.C.; Anthony King

(57) ABSTRACT

The invention provides a series of novel thiochromeno[2,3-c]quinolin-12-one derivatives. Further, the invention also provides the preparation method and application of said derivatives, said application comprises: said derivatives with treating effective amount are prepared into pharmaceutical compositions for inhibition of topoisomerase type I and II, inhibition of cancer cell growth, further treating cancer.

9 Claims, 4 Drawing Sheets

THIOCHROMENO[2,3-C]QUINOLIN-12-ONE DERIVATIVES, PREPARATION METHOD AND APPLICATION THEREOF

BACKGROUND OF THE INVENTION

1. Field of the Invention

The invention relates to development of cancer drug, especially relates to the development of novel thiochromeno[2,3-c]quinolin-12-one derivatives, preparation method and application thereof.

2. Description of the Prior Art

Telomerase is the enzyme that synthesizes telomeric DNA, the terminal DNA at chromosome ends which, together with telomere-binding proteins, confers stability to chromosomes. In most of organism, the replication and maintenance of the length of telomere has to rely on telomerase. The telomerase is composed of RNA and protein subunits. At present, part of important telomerase subunits had been identified. The composition of human telomerase comprising: human telomerase reverse transcriptase (hTERT) having reverse transcriptase activity, human telomerase RNA component used as a template, and some telomere-binding proteins such as human telomerase-associated protein, p23, hsp90, hsp40, hsp70 and the like.

Many research studies had indicated that the activity of human telomerase can only be detected in cells having high proliferation ability, for example, germ cells, hemopoietic cells, part of stem cells, most of immortalized cells and most of tumor cells. In the somatic cell, the telomere will be shorten gradually as the number of cell division increased, which may be considered as the mitotic clock for counting the number of cell division. When a telomere is shortened to a certain extent, cell will stop division and entering aging stage, stay at this stage for a period of time, and then goes to death. This period of time is called mortality stage 1 (M1 stage). When a tumor suppressor gene such as p53 or Rb is mutated within M1 stage, the cell might escape from aging stage and keeps on cell division in this period of time which is called mortality stage 2 (M2 stage). If a cell lacks of telomerase activity during this period, the length of a telomere will be reduced still, the telomere will not be able to protect the terminal end of the chromosome, and this might result into the instability of the chromosome, as well as the cell can not transfer genetic information completely and enters apoptosis in the end. Therefore, M2 stage is also called a crisis stage. Most of cells will die in M2 stage, except small part of cells with telomerase activity will survive. This small part of cells will continue to divide without limitation and become an immortalized cell (or a cancer cell).

In view of the foregoing, it is thought generally that the activation of telomerase can maintain the length of a telomere so as to prevent a cell from entering the ageing stage; or the inhibition of telomerase activity can be used to limit the division of a cancer cell. Both thought may become the key factors in the development of a cell toward immortalization or cancerization. In summary, using the telomerase inhibitors to treat the cancer have been considered as a novel cancer-specific therapy, as most tumor cells have high expression of telomerase, whereas most normal somatic cells express low or undetectable levels of telomerase and is therefore an attractive target for the design of anticancer agents.

Cancers arise from abnormal proliferation of DNA. Therefore, selectively destroy the DNA of cancer cells without damaging the DNA of normal cells is highly desired. However, it is difficult to differentiate the DNAs between normal cells and cancer cells. Consequently, specific 'targeted therapy' was developed following identification of the differences between normal cells and cancer cells, and when combined with other chemotherapies or radiation therapies, targeted therapy can significantly reduce side effects and provide better treatment outcomes. Thus, targeted therapy currently is a popular field in studying cancer treatments. Because topoisomerases have been found to play an indispensible role in DNA replication, they have become the objects of targeted therapy for anticancer treatments. The anticancer drug camptothecin discovered by M. E. Wall and M. C. Wani in 1966 through systematic screening of natural substances is an inhibitor for type I topoisomerases.

Unfortunately, camptothecin has numerous disadvantages and thus cannot be used for clinical treatment. For example, the lactone ring can be easily hydrolyzed to hydroxycarboxylate in vivo at the normal pH and then binds to serum albumin and lose its effect of inhibiting the function of type I topoisomerases. In addition, the structure of the tricomplex of camptothecin-Top I-DNA is not stable because the complex is not maintained by covalent bonds and water solubility of camptothecin is poor which causes lower bioavailability. The p-glycoprotein (MDR1, ABCB1) efflux transporter proteins in the cell membrane transported the drugs out of the cells and more important is that some tumor cells have slowly developed resistance and adverse drug side effects against camptothecin. As a result, a number of water-soluble semi-synthetic drugs were developed even after commercialization of camptothecin such as Topotecan (HYCAMTIN®) which is used for treating ovarian cancer and Irinotecan (CAMPTO®) which is used for treating colon cancer and both have issues when used for clinical treatment.

Hence, based on the importance of topoisomerase inhibitors in development of anticancer drugs, the inventor of this application developed a series of novel thiochromeno[2,3-c]quinolin-12-one derivatives and disclosed the preparation methods as well as relevant applications herein after a number of innovative improvements.

SUMMARY OF THE INVENTION

In one aspect, present invention provides a compound as shown in formulation (I):

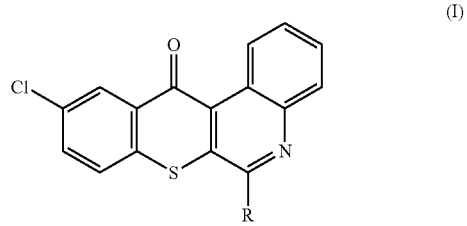

wherein the R is selected from the groups consisting of:
  i) haloformyl, amino, hydroxyl and thiol groups;
  ii) linear alkyl chains of $N(CH_2)_nH$, alkyl groups with substituted side chains, alkyl side chains with a substituted amino group and alkyl side chains with a substituted hydroxyl group, wherein $1 \leq n \leq 10$;
  iii) $O(CH_2)_nH$, $N(CH_3)_2$, $NH(CH_2)_nNH(CH_2)_nOH$, wherein $1 \leq n \leq 10$;
  iv) nitrogen-containing cycloalkyl groups and heterocyclic compounds of $C_{3-12}$ which contain 1 to 3 heteroatoms selected from O, S and N, wherein the ortho-, para- and meta-position can be further selected independently from one of the groups consisting of: hydrogen group, (CH$_2$)$_n$ alkyl groups, (CH$_2$)$_n$ hydroxyl groups, (CH$_2$)$_n$ C$_{3-12}$ cycloalkyl groups, (CH$_2$)$_n$C$_{3-12}$ nitrogen-containing cycloalkyl groups, (CH$_2$)$_n$ benzene rings, formyl group and (CH$_2$)$_n$COC$_{3-12}$ nitrogen-containing cycloalkyl groups, wherein 0≤n≤10;

v) NH(CH$_2$)$_n$R$_1$, 0≤n≤10, wherein R$_1$ is selected from the groups consisting of: N(CH$_3$)$_2$, C(NH$_2$)$_2$, linear alkyl chains of NH(CH$_2$)$_n$H, alkyl groups with substituted side chains, alkyl side chains with a substituted amino group and alkyl side chains with a substituted hydroxyl group;

vi) NH(CH$_2$)$_n$R$_2$, 0≤n≤10, wherein R$_2$ is selected from the groups consisting of: benzene rings, C$_{3-12}$ cycloalkyl groups and heterocyclic groups of which contain 1 to 3 heteroatoms selected from O, S and N, wherein the ortho-, para- and meta-position can be further selected independently from one of the groups consisting of: Methoxyl group, amino group, benzene rings, alkyl, amino, nitro, hydroxyl groups with substituted C1-C3 side chains and C$_{3-12}$ heterocyclic groups; wherein the C$_{3-12}$ heterocyclic groups which contain 1 to 3 heteroatoms selected from O, S and N;

and their pharmaceutically acceptable salts, stereoisomers and enantiomoers.

According to the invention, wherein the functional group i)~iv) are selected from the group consisting of chlorine, hydroxyl, methoxyl, dimethylamino, piperazin-1-yl, 4-methylpiperazin-1-yl, 4-ethylpiperazin-1-yl, 4-(2-hydroxyethyl)piperazin-1-yl, 4-Benzylpiperazin-1-yl, 4-phenylpiperazin-1-yl, morpholino, thiomorpholino, piperidin-1-yl, 4-hydroxypiperidin-1-yl, 4-Benzylpiperidin-1-yl, (1,4'-Bipiperidin)-1'-yl, 4-(3-(piperidin-4-yl)propyl)piperidin-1-yl, pyrrolidin-1-yl, 2-oxopiperidin-1-yl, methylamino, ethylamino, propylamino, butylamino, isobutylamino, pentan-3-ylamino, (2-(dimethylamino)ethyl)amino, (2-(diethylamino)ethyl)amino, 2-ethanolamino, 3-propanolamino, 5-pentanolamino, (1-hydroxybutan-2-yl)amino, (4-methylpentan-2-yl)amino, (2-Aminoethyl)amino, (2-((2-hydroxyethyl)amino)ethyl)amino, (2-morpholinoethyl)amino, (3-(dimethylamino)propyl)amino, (3-(diethylamino)propyl)amino, (3-((2-hydroxyethyl)amino)propyl)amino, (2,3-dihydro-1H-inden-2-yl)amino, cyclohexylamino, (1-Benzylpiperidin-4-yl)amino, (thiophen-2-ylmethyl)amino, (cyclohexylmethyl)amino, benzylamino, (pyridin-2-ylmethyl)amino, (Benzo[d][1,3]dioxol-5-ylmethyl)amino, (2-methoxybenzyl)amino, (3,4-dimethoxybenzyl)amino, phenethylamino, (4-methoxyphenethyl)amino, (4-aminophenethyl)amino, guanidine and piperidin-1-ylamino.

According to the invention, wherein the compound is selected from the group consisting of:

3-((4-Chlorophenyl)thio)-2-hydroxyquinoline-4-carboxylic acid,
6,9-Dichloro-12H-thiochromeno[2,3-c]quinolin-12-one,
10-Chloro-6-hydroxy-12H-thiochromeno[2,3-c]quinolin-12-one,
10-Chloro-6-methoxy-12H-thiochromeno[2,3-c]quinolin-12-one
10-Chloro-6-dimethylamino-12H-thiochromeno[2,3-c]quinolin-12-one,
10-Chloro-6-(piperazin-1-yl)-12H-thiochromeno[2,3-c]quinolin-12-one,
10-Chloro-6-(4-methylpiperazin-1-yl)-12H-thiochromeno[2,3-c]quinolin-12-one,
10-Chloro-6-(4-ethylpiperazin-1-yl)-12H-thiochromeno[2,3-c]quinolin-12-one,
10-Chloro-6-(4-(2-hydroxyethyl)piperazin-1-yl)-12H-thiochromeno[2,3-c]quinolin-12one,
6-(4-Benzylpiperazin-1-yl)-10-chloro-12H-thiochromeno[2,3-c]quinolin-12-one,
10-Chloro-6-(4-phenylpiperazin-1-yl)-12H-thiochromeno[2,3-c]quinolin-12-one,
10-Chloro-6-morpholino-12H-thiochromeno[2,3-c]quinolin-12-one,
10-Chloro-6-thiomorpholino-12H-thiochromeno[2,3-c]quinolin-12-one,
10-Chloro-6-(piperidin-1-yl)-12H-thiochromeno[2,3-c]quinolin-12-one,
10-Chloro-6-(4-hydroxypiperidin-1-yl)-12H-thiochromeno[2,3-c]quinolin-12-one,
6-(4-Benzylpiperidin-1-yl)-10-chloro-12H-thiochromeno[2,3-c]quinolin-12-one,
6-([1,4'-Bipiperidin]-1'-yl)-10-chloro-12H-thiochromeno[2,3-c]quinolin-12-one,
10-Chloro-6-(4-(3-(piperidin-4-yl)propyl)piperidin-1-yl)-12H-thiochromeno[2,3-c]quinolin-12-one,
10-Chloro-6-(pyrrolidin-1-yl)-12H-thiochromeno[2,3-c]quinolin-12-one,
10-Chloro-6-(2-oxopiperidin-1-yl)-12H-thiochromeno[2,3-c]quinolin-12-one,
10-Chloro-6-methylamino-12H-thiochromeno[2,3-c]quinolin-12-one,
10-Chloro-6-ethylamino-12H-thiochromeno[2,3-c]quinolin-12-one,
10-Chloro-6-propylamino-12H-thiochromeno[2,3-c]quinolin-12-one,
6-(Butylamino)-10-chloro-12H-thiochromeno[2,3-c]quinolin-12-one,
10-Chloro-6-isobutylamino-12H-thiochromeno[2,3-c]quinolin-12-one,
10-Chloro-6-(pentan-3-ylamino)-12H-thiochromeno[2,3-c]quinolin-12-one,
10-Chloro-6-((2-(dimethylamino)ethyl)amino)-12H-thiochromeno[2,3-c]quinolin-12-one,
10-Chloro-6-((2-(diethylamino)ethyl)amino)-12H-thiochromeno[2,3-c]quinolin-12-one,
10-Chloro-6-(2-ethanolamino)-12H-thiochromeno[2,3-c]quinolin-12-one,
10-Chloro-6-(3-propanolamino)-12H-thiochromeno[2,3-c]quinolin-12-one,
10-Chloro-6-(5-pentanolamino)-12H-thiochromeno[2,3-c]quinolin-12-one,
10-Chloro-6-((1-hydroxybutan-2-yl)amino)-12H-thiochromeno[2,3-c]quinolin-12-one,
10-Chloro-6-((4-methylpentan-2-yl)amino)-12H-thiochromeno[2,3-c]quinolin-12-one,
6-((2-Aminoethyl)amino)-10-chloro-12H-thiochromeno[2,3-c]quinolin-12-one,
10-Chloro-6-((2-((2-hydroxyethyl)amino)ethyl)amino)-12H-thiochromeno[2,3-c]quinolin-12-one,
10-Chloro-6-((2-morpholinoethyl)amino)-12H-thiochromeno[2,3-c]quinolin-12-one,
10-Chloro-6-((3-(dimethylamino)propyl)amino)-12H-thiochromeno[2,3-c]quinolin-12-one,
10-Chloro-6-((3-(diethylamino)propyl)amino)-12H-thiochromeno[2,3-c]quinolin-12-one,
10-Chloro-6-((3-((2-hydroxyethyl)amino)propyl)amino)-12H-thiochromeno[2,3-c]quinolin-12-one,
10-Chloro-6-((2,3-dihydro-1H-inden-2-yl)amino)-12H-thiochromeno[2,3-c]quinolin-12-one,
10-Chloro-6-(cyclohexylamino)-12H-thiochromeno[2,3-c]quinolin-12-one,
6-((1-Benzylpiperidin-4-yl)amino)-10-chloro-12H-thiochromeno[2,3-c]quinolin-12-one, 10-Chloro-6-((thiophen-2-ylmethyl)amino)-12H-thiochromeno[2,3-c]quinolin-12-one,
10-Chloro-6-((cyclohexylmethyl)amino)-12H-thiochromeno[2,3-c]quinolin-12-one,
6-(Benzylamino)-10-chloro-12H-thiochromeno[2,3-c]quinolin-12-one
10-Chloro-6-((pyridin-2-ylmethyl)amino)-12H-thiochromeno[2,3-c]quinolin-12-one,
6-((Benzo[d][1,3]dioxol-5-ylmethyl)amino)-10-chloro-12H-thiochromeno[2,3-c]quinolin-12-one,
10-Chloro-6-((2-methoxybenzyl)amino)-12H-thiochromeno[2,3-c]quinolin-12-one,
10-Chloro-6-((3,4-dimethoxybenzyl)amino)-12H-thiochromeno[2,3-c]quinolin-12-one,
10-Chloro-6-(phenethylamino)-12H-thiochromeno[2,3-c]quinolin-12-one,
10-Chloro-6-((4-methoxyphenethyl)amino)-12H-thiochromeno[2,3-c]quinolin-12-one,
6-((4-Aminophenethyl)amino)-10-chloro-12H-thiochromeno[2,3-c]quinolin-12-one,
2-(10-Chloro-12-oxo-12H-thiochromeno[2,3-c]quinolin-6-yl)guanidine,
10-Chloro-6-(piperidin-1-ylamino)-12H-thiochromeno[2,3-c]quinolin-12-one,
and their salts.

In another aspect, the invention provides a pharmaceutical composition comprising an effective amount of the abovementioned compound and at least one pharmaceutically acceptable vehicle, diluent or excipient.

In another aspect, the invention provides a method for inhibiting Topoisomerase I activity which comprises administrating an effective amount of the abovementioned compound.

In another aspect, the invention provides a method for inhibiting Topoisomerase II activity which comprises administrating an effective amount of the compound according to claim 1.

In another aspect, the invention provides a method for the treatment of cancer which comprises administrating an effective amount of the compound according to claim 1.

According to the invention, wherein the cancers are selected from the groups consisting of leukemia, non-small cell lung cancer, colorectal cancer, central nervous system (CNS) cancer, melanoma, ovarian cancer, renal cancer, prostate cancer and breast cancer.

In another aspect, the invention provides a method for preparation of thiochromeno[2,3-c]quinolin-12-one derivatives, wherein the method comprising:
(1) mix isatin, 2-((4-chlorophenyl)thio)acetic acid and sodium acetate was heated at 150° C. for 1 h, after cooling the mixture was added acetic acid, the precipitate was collected, washed with acetic acid, water and n-hexane, and obtained compound 2 (3-((4-Chlorophenyl)thio)-2-hydroxyquinoline-4-carboxylic acid);
(2) a solution of compound 2 (3-((4-Chlorophenyl)thio)-2-hydroxyquinoline-4-carboxylic acid) in phosphoryl trichloride was heated at 150° C. for 48 h, after cooling the mixture was poured into water 0° C., the precipitate was collected by filtration, then added into 10% NaHCO₃ with vigorous stirring for 1 h, the resulting precipitate was collected and washed with H₂O, the crude solid was recrystallized by dichloromethane to give compound 3 (6,9-Dichloro-12H-thiochromeno[2,3-c]quinolin-12-one);
(3) a solution of compound 3 (6,9-Dichloro-12H-thiochromeno[2,3-c]quinolin-12-one) in DMF was added conc. HCl and refluxed, after 6 hours, the conc. HCl was added dropwise and refluxed for another 12 hours, the mixture was evaporated in vacuo and treated with H₂O, after filtered the crude solid was washed with EtOH to give compound 4 (10-Chloro-6-hydroxy-12H-thiochromeno[2,3-c]quinolin-12-one);
(4) a suspension of compound 3 (6,9-Dichloro-12H-thiochromeno[2,3-c]quinolin-12-one) and sodium methoxide in methanol was refluxed for 16 h, after cooled the solvent was removed, filtrated and washed with ethanol and n-hexane to collect compound 5 (10-Chloro-6-methoxy-12H-thiochromeno[2,3-c]quinolin-12-one);
(5) a solution of compound 3 (6,9-Dichloro-12H-thiochromeno[2,3-c]quinolin-12-one), appropriate secondary amines and sodium carbonate in DMSO was refluxed for 10 hours, then the reaction was added ice-water, the precipitate was filtered, washed with water/methanol and collected to get compound 6-21:
10-Chloro-6-dimethylamino-12H-thiochromeno[2,3-c]quinolin-12-one,
10-Chloro-6-(piperazin-1-yl)-12H-thiochromeno[2,3-c]quinolin-12-one,
10-Chloro-6-(4-methylpiperazin-1-yl)-12H-thiochromeno[2,3-c]quinolin-12-one,
10-Chloro-6-(4-ethylpiperazin-1-yl)-12H-thiochromeno[2,3-c]quinolin-12-one,
10-Chloro-6-(4-(2-hydroxyethyl)piperazin-1-yl)-12H-thiochromeno[2,3-c]quinolin-12one,
6-(4-Benzylpiperazin-1-yl)-10-chloro-12H-thiochromeno[2,3-c]quinolin-12-one,
10-Chloro-6-(4-phenylpiperazin-1-yl)-12H-thiochromeno[2,3-c]quinolin-12-one,
10-Chloro-6-morpholino-12H-thiochromeno[2,3-c]quinolin-12-one,
10-Chloro-6-thiomorpholino-12H-thiochromeno[2,3-c]quinolin-12-one,
10-Chloro-6-(piperidin-1-yl)-12H-thiochromeno[2,3-c]quinolin-12-one,
10-Chloro-6-(4-hydroxypiperidin-1-yl)-12H-thiochromeno[2,3-c]quinolin-12-one,
6-(4-Benzylpiperidin-1-yl)-10-chloro-12H-thiochromeno[2,3-c]quinolin-12-one,
6-([1,4'-Bipiperidin]-1'-yl)-10-chloro-12H-thiochromeno[2,3-c]quinolin-12-one,
10-Chloro-6-(4-(3-(piperidin-4-yl)propyl)piperidin-1-yl)-12H-thiochromeno[2,3-c]quinolin-12-one,
10-Chloro-6-(pyrrolidin-1-yl)-12H-thiochromeno[2,3-c]quinolin-12-one, and
10-Chloro-6-(2-oxopiperidin-1-yl)-12H-thiochromeno[2,3-c]quinolin-12-one respectively;
(6) a solution of compound 3 (6,9-Dichloro-12H-thiochromeno[2,3-c]quinolin-12-one) in DMSO was added appropriate primary amines and refluxed for 8 hours, after cooled the reaction was added water, the precipitate was filtered and washed with water and methanol to collect compound N1~N34:
10-Chloro-6-methylamino-12H-thiochromeno[2,3-c]quinolin-12-one,
10-Chloro-6-ethylamino-12H-thiochromeno[2,3-c]quinolin-12-one,
10-Chloro-6-propylamino-12H-thiochromeno[2,3-c]quinolin-12-one,
6-(Butylamino)-10-chloro-12H-thiochromeno[2,3-c]quinolin-12-one,
10-Chloro-6-isobutylamino-12H-thiochromeno[2,3-c]quinolin-12-one,
10-Chloro-6-(pentan-3-ylamino)-12H-thiochromeno[2,3-c]quinolin-12-one, 10-Chloro-6-((2-(dimethylamino)ethyl)amino)-12H-thiochromeno[2,3-c]quinolin-12-one,
10-Chloro-6-((2-(diethylamino)ethyl)amino)-12H-thiochromeno[2,3-c]quinolin-12-one,
10-Chloro-6-(2-ethanolamino)-12H-thiochromeno[2,3-c]quinolin-12-one,
10-Chloro-6-(3-propanolamino)-12H-thiochromeno[2,3-c]quinolin-12-one,
10-Chloro-6-(5-pentanolamino)-12H-thiochromeno[2,3-c]quinolin-12-one,
10-Chloro-6-((1-hydroxybutan-2-yl)amino)-12H-thiochromeno[2,3-c]quinolin-12-one,
10-Chloro-6-((4-methylpentan-2-yl)amino)-12H-thiochromeno[2,3-c]quinolin-12-one,
6-((2-Aminoethyl)amino)-10-chloro-12H-thiochromeno[2,3-c]quinolin-12-one,
10-Chloro-6-((2-((2-hydroxyethyl)amino)ethyl)amino)-12H-thiochromeno[2,3-c]quinolin-12-one,
10-Chloro-6-((2-morpholinoethyl)amino)-12H-thiochromeno[2,3-c]quinolin-12-one,
10-Chloro-6-((3-(dimethylamino)propyl)amino)-12H-thiochromeno[2,3-c]quinolin-12-one,
10-Chloro-6-((3-(diethylamino)propyl)amino)-12H-thiochromeno[2,3-c]quinolin-12-one,
10-Chloro-6-((3-((2-hydroxyethyl)amino)propyl)amino)-12H-thiochromeno[2,3-c]quinolin-12-one,
10-Chloro-6-((2,3-dihydro-1H-inden-2-yl)amino)-12H-thiochromeno[2,3-c]quinolin-12-one,
10-Chloro-6-(cyclohexylamino)-12H-thiochromeno[2,3-c]quinolin-12-one,
6-((1-Benzylpiperidin-4-yl)amino)-10-chloro-12H-thiochromeno[2,3-c]quinolin-12-one,
10-Chloro-6-((thiophen-2-ylmethyl)amino)-12H-thiochromeno[2,3-c]quinolin-12-one,
10-Chloro-6-((cyclohexylmethyl)amino)-12H-thiochromeno[2,3-c]quinolin-12-one,
6-(Benzylamino)-10-chloro-12H-thiochromeno[2,3-c]quinolin-12-one,
10-Chloro-6-((pyridin-2-ylmethyl)amino)-12H-thiochromeno[2,3-c]quinolin-12-one,
6-((Benzo[d][1,3]dioxol-5-ylmethyl)amino)-10-chloro-12H-thiochromeno[2,3-c]quinolin-12-one,
10-Chloro-6-((2-methoxybenzyl)amino)-12H-thiochromeno[2,3-c]quinolin-12-one,
10-Chloro-6-((3,4-dimethoxybenzyl)amino)-12H-thiochromeno[2,3-c]quinolin-12-one,
10-Chloro-6-(phenethylamino)-12H-thiochromeno[2,3-c]quinolin-12-one,
10-Chloro-6-((4-methoxyphenethyl)amino)-12H-thiochromeno[2,3-c]quinolin-12-one,
6-((4-Aminophenethyl)amino)-10-chloro-12H-thiochromeno[2,3-c]quinolin-12-one,
2-(10-Chloro-12-oxo-12H-thiochromeno[2,3-c]quinolin-6-yl) guanidine, and
10-Chloro-6-(piperidin-1-ylamino)-12H-thiochromeno[2,3-c]quinolin-12-one respectively.

These features and advantages of the present invention will be fully understood and appreciated from the following detailed description of the accompanying Drawings.

DETAILED DESCRIPTION OF THE PREFERRED EMBODIMENT

Figure 1:
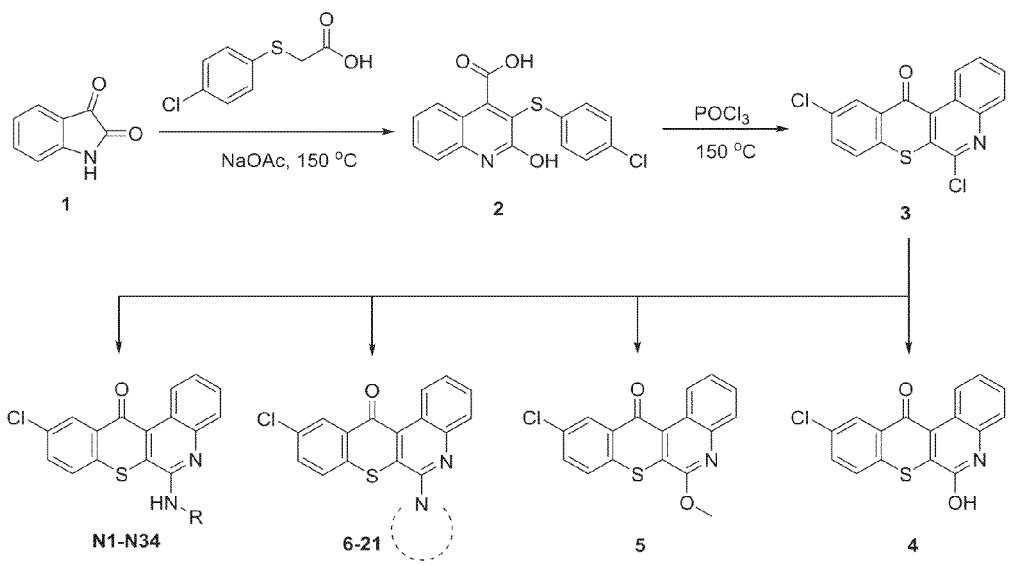
FIG. 1 depicts the general scheme for a series of thiochromeno[2,3-c]quinolin-12-one derivatives.

Unless defined otherwise, all technical and scientific terms used herein have the meaning commonly understood by a person skilled in the art to which this invention belongs. As used herein, the following terms have the meanings ascribed to them unless specified otherwise. The present invention will now be described more specifically with reference to the following embodiments, which are provided for the purpose of demonstration rather than limitation.

The term "treatment", "under treatment" and similar terms refer to the methods which ameliorate, improve, reduce or reverse the patient's disease or any relevant symptoms caused by the disease, or methods which can prevent onset of such diseases or any resulting symptoms.

The term "pharmaceutically acceptable" is used to describe substances to be used in the composition must be compatible with other ingredients in the formulation and be harmless to the subject.

The inventive composition can be prepared into a dosage form for suitable application of the inventive composition by using technology commonly understood by a person skilled in the art through formulating the abovementioned *Lactobacillus* isolated strain(s) with a pharmaceutically acceptable vehicle, wherein the excipients include, but are not limited to, solution, emulsion, suspension, powder, tablet, pill, lozenge, troche, chewing gum, slurry, and other suitable forms.

The pharmaceutically acceptable vehicle may contain one or several reagents selecting form the following list: solvents, emulsifiers, suspending agents, decomposers, binding agents, excipients, stabilizing agents, chelating agents, diluents, gelling agents, preservatives, lubricants, surfactants and other agents suitable for use in the invention.

In the abovementioned compositions, one or more dissolving aids, buffers, preservatives, colorants, fragrances, flavoring agents and the like, which are commonly used for formulation can be added as desired.

The term "pharmaceutically acceptable excipients", as used herein, refers to substances known by persons skilled in the art, which are physiologically inert, pharmacologically inactive and are compatible with the physical as well as chemical characteristics of sorafenib or GW5074. Pharmaceutically acceptable excipients include, but are not limited to, polymers, resins, plasticizers, fillers, lubricants, diluents, binders, disintegrants, solvents, co-solvents, surfactants, preservatives, sweetening agents, flavoring agents, pharmaceutical grade dyes or pigments, and viscosity agents.

The term "pharmaceutical composition" is used to describe solid or liquid compositions in a form, concentration and purity that are suitable for administration in patients (e.g.

humans or animals) and can induce desired physiological changes following administration. Pharmaceutical compositions are typically sterile and non-pyrogenic.

The present invention will now be described more specifically with reference to the following embodiments, which are provided for the purpose of demonstration rather than limitation. The drugs as well as biomaterials used in the invention are all commercially available materials and the sources disclosed below are merely examples.

All reactions were monitored by thin-layer chromatography (TLC) coated with silica gel 60 $F_{254}$. Melting points of all synthetic compounds were measured with Büchi B-545 melting point apparatus. $^1$H NMR: Varian GEMINI-300 (300 MHz) or Agilent 400 MR DD2 (400 MHz); δ values are in ppm relative to tetramethylsilane (TMS) as an internal standard (0 ppm). Multiplicities are recorded as s (singlet), d (doublet), t (triplet), q (quartet), quin (quintuplet), sext (sextet), sep (septet), m (multiplet), dd (doublet of doublet), dt (doublet of triplet), td (triplet of doublet), qd (quartet of doublet) and br (broadened). Mass spectra: High resolution electrospray ionization (HRESI): Finnigan MAT 95S (Instrumentation Center, National Taiwan University, Taipei, Taiwan). X-ray Single Crystal Diffraction: Bruker Enraf-Nonius APEX II diffractometer (Department of Chemistry, National Taiwan Normal University). Typical experiments illustrating the general procedures for the preparation of the thiochromenoquinolones are described below (FIG. 1).

General Procedures for Chemical Synthesis

General Procedure A: Preparation of Compound 2

A mixture of isatin (1) (0.44 g, 2.99 mmol), 2-((4-chlorophenyl)thio)acetic acid (0.70 g, 3.47 mmol), and sodium acetate (0.05 g) was heated at 150° C. in miniclave for 1 h (TLC monitored). After cooling, the mixture was added acetic acid 10 mL, and the gray precipitate was collected, washed with acetic acid, water and n-hexane, and obtained light purple compound.

General Procedure B: Preparation of Compound 3

A solution of compound 2 (0.55 g, 2.1 mmol) in phosphoryl trichloride (5 mL) was heated at 150° C. for 48 h. After cooling, the mixture was poured into ice (50 mL) at 0° C. The resulting green precipitate that separated was collected by filtration. The filtered cake was suspended in 10% NaHCO$_3$ solution (50 mL) with vigorous stirring for 1 h. The resulting precipitate was collected and washed with H$_2$O. The crude solid was recrystallized from dichloromethane to give yellow product.

General Procedure C: Preparation of Compound 4

To a solution of compound 3 (0.32 g, 0.96 mmol) in DMF (20 mL) was added conc. HCl (3 mL) and refluxed. After 6 h, the conc. HCl (6 mL) was added dropwise and refluxed for another 12 h. The mixture was evaporated in vacuo and treated with H$_2$O (20 mL), after filtered the crude solid was washed with EtOH to give yellow solid.

General Procedure D: Preparation of Compound 5

A suspension of compound 3 (0.33 g, 1.0 mmol) and sodium methoxide (0.55 g, 10 mmol) in methanol (20 mL) was refluxed for 16 h. After cooled, the solvent was removed by rotarvapor vacuum, filtrated and washed with ethanol and n-hexane to collect the white solid.

General Procedure E: Preparation of Compounds 6-21

Compound 3 (0.33 g, 1.0 mmol), appropriate secondary amines (1.1 mmol) and sodium carbonate (5 mmol) in DMSO (20 mL) was refluxed for 10 h (TLC monitored). After 30 min, the reaction was added ice-water (100 mL). The precipitate was filtered, washed with water/methanol and collected to get the yellow solid.

General Procedure F: Preparation of Compounds N1-N32

To a solution of compound 3 (0.33 g, 1.0 mmol) in DMSO (30 mL) was added appropriate primary amines (1.1 mmol) and refluxed for 8 h (TLC monitored). After cooled, the reaction was added water (100 mL). The precipitate was filtered and washed with water and hot methanol to collect the yellow solid.

Example 1

3-((4-Chlorophenyl)thio)-2-hydroxyquinoline-4-carboxylic acid (TC-SCl) (2)

The pure compound was obtained as a gray solid (yield 86%). ($R_f$=0.5 at EA:AcOH=20:1). Mp 306-308° C. $^1$H NMR (300 MHz, DMSO-d$_6$): δ (ppm) 7.26 (3H, t, J=7.6 Hz, Ar—H), 7.34 (2H, d, J=6.0 Hz, Ar—H), 7.39 (1H, d, J=8.0 Hz, Ar—H), 7.46 (1H, d, J=8.0 Hz, Ar—H), 7.62 (1H, t, J=8.0 Hz, Ar—H), 12.22 (1H, s, —COOH). $^{13}$C NMR (100 MHz, DMSO-d$_6$): δ (ppm) 115.58, 116.26, 120.36, 123.21, 126.21, 129.33, 130.30, 131.47, 132.54, 134.36, 140.11, 151.69, 159.37, 166.80 (CO). HRMS (ESI) calcd for $C_{16}H_{10}NO_3SCl$ [M]$^+$ 331.0070. found [M+H]$^+$332.0147 (100), [M+H+2]$^+$ 334.0122 (33). found [M−H]$^-$ 330.0002.

Example 2

6,9-Dichloro-12H-thiochromeno[2,3-c]quinolin-12-one (3)

The yellow solid material was isolated in 90% yield ($R_f$=0.50 at CH$_2$Cl$_2$:n-hexane=1:1). Mp 259-261° C. (CH$_2$Cl$_2$). $^1$H NMR (400 MHz, CDCl$_3$): δ (ppm) 7.71 (2H, m, Ar—H), 7.77-7.85 (2H, m, Ar—H), 8.10-8.13 (m, 1H, Ar—H), 8.60 (t, 1H, J=1.2 Hz, Ar—H), 9.67-9.71 (1H, m, Ar—H). $^{13}$C NMR (100 MHz, CDCl$_3$): δ (ppm) 124.87, 126.28, 127.85, 129.17, 129.39, 129.93, 130.31, 131.20, 131.90, 133.01, 133.09, 133.38, 134.43, 145.27, 146.61, 180.64 (CO). HRMS (ESI) calcd for $C_{16}H_7NOSCl_2$ [M]$^+$ 330.9625. found [M+H]$^+$ 331.9699 (100), [M+H+2]$^+$ 333.9672 (67), [M+H+4]$^+$ 335.9645 (11).

Example 3

10-Chloro-6-hydroxy-12H-thiochromeno[2,3-c]quinolin-12-one (4)

The yellow solid material was isolated in 95% yield ($R_f$=0.40 at EA). Mp>410° C. $^1$H NMR (400 MHz, DMSO-d6): δ ppm 7.35 (1H, td, J=7.2, 1.2 Hz, Ar—H), 7.47 (1H, dd, J=8.4, 1.2 Hz, Ar—H), 7.59 (1H, td, J=7.2 Hz, 1.6 Hz, Ar—H), 7.89 (1H, dd, J=8.4 Hz, 2.4 Hz, Ar—H), 8.10 (1H, d, J=8.8 Hz, Ar—H), 8.38 (1H, d, J=2.4 Hz, Ar—H), 9.35 (1H, dd, J=8.4, 2.4 Hz, Ar—H), 12.73 (br, 1H, —OH). $^{13}$C NMR (75 MHz, CDCl$_3$): δ (ppm) 116.61, 117.52, 123.65, 126.82, 128.44, 130.22, 130.49, 130.54, 132.52, 133.00, 133.42, 135.09, 136.27, 138.90, 158.70, 180.38 (CO). HRMS (ESI) m/z calcd for $C_{16}H_8NO_2SCl$ [M]$^+$: 312.9964. found, 314.0051.

Example 4

10-Chloro-6-methoxy-12H-thiochromeno[2,3-c]quinolin-12-one (5)

The gray solid material was isolated in 91% yield ($R_f$=0.52 at CH$_2$Cl$_2$:n-hexane=1:1). Mp 227-228° C. $^1$H NMR (400

MHz, CDCl$_3$): δ (ppm) 4.27 (3H, s, —OCH$_3$), 7.60 (1H, td, J=7.6, 1.2 Hz, Ar—H), 7.37 (1H, d, J=2.0 Hz, Ar—H), 7.70 (1H, td, J=7.6 Hz, 1.6 Hz, Ar—H), 7.94 (1H, dd, J=8.0 Hz, 1.2 Hz, Ar—H), 8.60 (1H, d, J=1.6 Hz, Ar—H), 9.64 (1H, dd, J=8.8 Hz, 1.2 Hz, Ar—H). $^{13}$C NMR (100 MHz, CDCl$_3$): δ (ppm) 54.83 (OCH$_3$), 122.91, 126.23, 126.54, 126.76, 127.66, 127.95, 129.23, 129.50, 130.54, 132.49, 133.48, 133.85, 143.82, 156.06, 180.47 (CO). HRMS (ESI) m/z calcd for C$_{17}$H$_{10}$NO$_2$SCl [M]$^+$ 327.0121. found [M+H]$^+$ 328.0203, [M+H+2]$^+$ 330.0172.

Example 5

10-Chloro-6-dimethylamino-12H-thiochromeno[2,3-c]quinolin-12-one (6)

Product 6 was prepared from 3 and dimethylamine. The light-yellow solid material was isolated in 85% yield (R$_f$=0.45 at CH$_2$Cl$_2$:n-hexane=1:1). Mp 194-195° C. $^1$H NMR (400 MHz, CDCl$_3$): δ (ppm) 3.06 (6H, s, —CH$_3$), 7.59-7.67 (3H, m, Ar—H), 7.71 (1H, t, J=7.2 Hz, Ar—H), 8.00 (1H, d, J=8.4 Hz, Ar—H), 8.59 (1H, d, J=1.2 Hz, Ar—H), 9.60 (1H, d, J=8.4 Hz, Ar—H). $^{13}$C NMR (100 MHz, CDCl$_3$): δ (ppm) 43.00, 123.44, 125.71, 127.22, 127.78 128.47, 129.07, 129.37, 130.59, 130.67, 132.23, 132.46, 133.61, 134.36, 144.84, 158.32, 181.52 (CO). HRMS (ESI) calcd for C$_{18}$H$_{13}$N$_2$OSCl [M]$^+$ 340.0437. found [M+H]$^+$ 341.0517 (100), [M+H+2]$^+$ 343.0501 (33).

Example 6

10-Chloro-6-(piperazin-1-yl)-12H-thiochromeno[2,3-c]quinolin-12-one (7)

Product 7 was prepared from 3 and piperazine. The dark-yellow solid material was isolated in 69% yield (R$_f$=0.12 at EA:MeOH:ammonia water=20:5:1). Mp 211-213° C. $^1$H NMR (400 MHz, CDCl$_3$): δ (ppm) 3.20 (4H, t, J=4.8 Hz, —CH$_2$—), 3.36 (4H, t, J=4.8 Hz, —CH$_2$—), 7.60-7.66 (3H, m, Ar—H), 7.70 (1H, td, J=8.0, 1.2 Hz, Ar—H), 7.99 (1H, dd, J=8.4, 0.8 Hz, Ar—H), 8.56 (1H, d, J=2.0 Hz, Ar—H), 9.60 (1H, dd, J=8.4, 0.8 Hz, Ar—H). $^{13}$C NMR (100 MHz, CDCl$_3$): δ (ppm) 45.95, 52.31, 123.62, 125.81, 127.58, 127.86, 128.72, 129.10, 129.37, 130.65, 130.99, 132.17, 132.47, 133.63, 134.33, 144.94, 157.61, 181.45 (CO). HRMS (ESI) calcd for C$_{20}$H$_{16}$N$_3$OSCl [M]$^+$381.0703. found [M+H]$^+$ 382.0783.

Example 7

10-Chloro-6-(4-methylpiperazin-1-yl)-12H-thiochromeno[2,3-c]quinolin-12-one (8)

Product 8 was prepared from 3 and 1-methylpiperazine. The green-yellow solid material was isolated in 80% yield (R$_f$=0.24 at EA:methanol=5:1). Mp 212-214° C. $^1$H NMR (400 MHz, CDCl$_3$): δ (ppm) 2.51 (3H, s, —CH$_3$), 2.84 (4H, br, —CH$_2$—), 3.50 (4H, t, J=4.5 Hz, —CH$_2$—), 7.60-7.66 (3H, m, Ar—H), 7.68-7.72 (1H, td, J=8.1, 1.5 Hz, Ar—H), 8.01 (1H, dd, J=8.1, 1.5 Hz, Ar—H), 8.56 (1H, d, J=1.5 Hz, Ar—H), 9.60 (1H, dd, J=8.4, 1.5 Hz, Ar—H). $^{13}$C NMR (100 MHz, CDCl$_3$): δ (ppm) 45.73, 50.31, 54.65, 123.70, 125.90, 127.60, 127.80, 128.82, 129.20, 129.39, 130.62, 130.84, 132.36, 132.47, 133.78, 134.24, 145.08, 157.18, 181.42 (CO). HRMS (ESI) calcd for C$_{21}$H$_{18}$N$_3$OSCl [M]$^+$395.0859. found [M+H]$^+$396.0926.

Example 8

10-Chloro-6-(4-ethylpiperazin-1-yl)-12H-thiochromeno[2,3-c]quinolin-12-one (9)

Product 9 was prepared from 3 and 1-ethylpiperazine. The yellow solid material was isolated in 74% yield (R$_f$=0.48 at EA:MeOH=10:1). Mp 196-198° C. $^1$H NMR (400 MHz, CDCl$_3$): δ (ppm) 1.19 (3H, t, J=7.2 Hz, —CH$_3$), 2.58 (2H, q, J=7.2 Hz, —CH$_2$—), 2.78 (4H, br, —CH$_2$—), 3.46 (4H, t, J=4.4 Hz, —CH$_2$—), 7.61-7.66 (3H, m, Ar—H), 7.68-7.73 (1H, td, J=8.4, 1.6 Hz, Ar—H), 8.01 (1H, dd, J=8.0, 1.2 Hz, Ar—H), 8.59 (1H, d, J=4.0 Hz, Ar—H), 9.62 (1H, dd, J=8.4, 0.8 Hz, Ar—H). $^{13}$C NMR (100 MHz, CDCl$_3$): δ (ppm) 12.07, 50.88, 52.46, 52.67, 123.55, 125.77, 127.48, 127.83, 128.78, 129.12, 129.36, 130.62, 130.76, 132.21, 132.47, 133.62, 134.34, 144.97, 157.34, 181.50 (CO). HRMS (ESI) calcd for C$_{22}$H$_{20}$N$_3$OSCl [M]$^+$409.1016. found [M+H]$^+$ 410.1069.

Example 9

10-Chloro-6-(4-(2-hydroxyethyl)piperazin-1-yl)-12H-thiochromeno[2,3-c]quinolin-12one (10)

Product 10 was prepared from 3 and 2-(piperazin-1-yl)ethanol. The green-yellow solid material was isolated in 60% yield (R$_f$=0.37 at EA:MeOH=2:1). Mp 211-213° C. $^1$H NMR (400 MHz, CDCl$_3$): δ (ppm) 2.74 (2H, t, J=5.2 Hz, —CH$_2$—), 2.87 (4H, t, J=3.6 Hz, —CH$_2$—), 3.45 (4H, t, J=3.6 Hz, —CH$_2$—), 3.72 (2H, t, J=5.2 Hz, —CH$_2$O—), 7.62-7.67 (3H, m, Ar—H), 7.72 (1H, td, J=7.2, 1.6 Hz, Ar—H), 8.01 (1H, dd, J=8.4, 1.2 Hz, Ar—H), 8.59 (1H, d, J=0.6 Hz, Ar—H), 9.62 (1H, dd, J=4.8, 1.2 Hz, Ar—H). $^{13}$C NMR (100 MHz, CDCl$_3$): δ (ppm) 50.85, 52.72, 57.74, 59.35, 123.65, 125.81, 127.66, 127.82, 128.73, 129.14, 129.44, 130.68, 130.77, 132.19, 132.51, 133.69, 134.21, 144.90, 157.26, 181.43 (CO). HRMS (ESI) calcd for C$_{22}$H$_{20}$N$_3$O$_2$SCl [M]$^+$ 425.0965. found [M+H]$^+$ 426.1024.

Example 10

6-(4-Benzylpiperazin-1-yl)-10-chloro-12H-thiochromeno[2,3-c]quinolin-12-one (11)

Product 11 was prepared from 3 and 4-benzylpiperazine. The yellow solid material was isolated in 81% yield (R$_f$=0.43 at EA:n-hexane=1:4). Mp 191-193° C. $^1$H NMR (400 MHz, CDCl$_3$): δ (ppm) 2.78 (4H, br, —CH$_2$N—), 3.43 (4H, t, J=4.85 Hz, —NCH$_2$—), 3.68 (2H, s, —CH$_2$—), 7.27-7.42 (5H, m, Ar'—H), 7.61-7.67 (3H, m, Ar—H), 7.71 (1H, td, J=7.6, 1.6 Hz, Ar—H), 8.00 (1H, dd, J=8.4, 1.2 Hz, Ar—H), 8.58 (1H, d, J=2.0 Hz, Ar—H), 9.61 (1H, dd, J=8.4, 1.2 Hz, Ar—H). $^{13}$C NMR (100 MHz, CDCl$_3$): δ (ppm) 50.94, 52.96, 63.08, 123.57, 125.78, 127.18, 127.48, 127.83, 128.33, 128.73, 129.09, 129.17, 129.34, 130.58, 130.90, 132.18, 132.44, 133.60, 134.36, 138.11, 144.95, 157.48, 181.47 (CO). HRMS (ESI) calcd for C$_{27}$H$_{22}$N$_3$OSCl [M]$^+$ 471.1172. found [M+H]$^+$ 472.1241.

Example 11

10-Chloro-6-(4-phenylpiperazin-1-yl)-12H-thiochromeno[2,3-c]quinolin-12-one (12)

Product 12 was prepared from 3 and 1-phenylpiperazine. The yellow solid material was isolated in 77% yield (R$_f$=0.73 at EA:n-hexane=1:4). Mp 236-237° C. $^1$H NMR (300 MHz, CDCl$_3$): δ (ppm) 3.50-3.60 (8H, m, —CH$_2$—), 6.94 (1H, t, J=7.2 Hz, Ar'—H), 7.04 (2H, d, J=8.4 Hz, Ar'—H), 7.33 (2H, t, J=7.5 Hz, Ar'—H), 7.63-7.67 (3H, m, Ar—H), 7.71 (1H, t, J=7.2 Hz, Ar—H), 8.02 (1H, d, J=7.2 Hz, Ar—H), 8.58 (1H, s, Ar—H), 9.63 (1H, d, J=8.1 Hz, Ar—H). $^{13}$C NMR (75 MHz, CDCl$_3$): δ (ppm) 48.60, 50.33, 115.77, 119.51, 123.21, 125.38, 127.14, 127.30, 128.27, 128.65, 128.71, 128.88, 130.23, 131.77, 131.97, 133.22, 133.70, 144.52, 150.90, 156.83, 159.91, 180.91 (CO). HRMS (ESI) calcd for C$_{26}$H$_{20}$N$_3$OSCl [M]$^+$ 457.1016. found [M+H]$^+$ 458.1095.

Example 12

10-Chloro-6-morpholino-12H-thiochromeno[2,3-c]quinolin-12-one (13)

Product 13 was prepared from 3 and morpholine. The yellow solid material was isolated in 70% yield (R$_f$=0.42 at CH$_2$Cl$_2$). Mp 217-218° C. $^1$H NMR (300 MHz, CDCl$_3$): δ (ppm) 3.41 (4H, t, J=4.5 Hz, —NCH$_2$—), 4.02 (4H, t, J=4.5 Hz, —CH$_2$O—), 7.62-7.70 (3H, m, Ar—H), 7.73 (1H, td, J=7.5, 1.5 Hz, Ar—H), 8.03 (1H, dd, J=8.4, 1.5 Hz, Ar—H), 8.59 (1H, dd, J=2.1, 0.6 Hz, Ar—H), 9.35 (1H, dd, J=8.7, 1.8 Hz, Ar—H). $^{13}$C NMR (75 MHz, CDCl$_3$): δ (ppm) 51.36, 66.88, 123.92, 126.06, 127.85, 127.91, 128.94, 129.34, 129.52, 130.71, 131.05, 132.50, 132.61, 133.95, 134.29, 145.23, 157.29, 181.51 (CO). HRMS (ESI) calcd for C$_{20}$H$_{15}$N$_2$O$_2$SCl [M]$^+$ 382.8633. found [M+H]$^+$ 383.0620.

Example 13

10-Chloro-6-thiomorpholino-12H-thiochromeno[2,3-c]quinolin-12-one (14)

Product 14 was prepared from 3 and thiomorpholine. The yellow solid material was isolated in 86% yield (R$_f$=0.77 at EA:n-hexane=1:4). Mp 219-220° C. $^1$H NMR (300 MHz, CDCl$_3$): δ (ppm) 2.98 (4H, t, J=4.8 Hz, —NCH$_2$—), 3.64 (4H, t, J=5.1 Hz, —SCH$_2$—), 7.62-7.84 (3H, m, Ar—H), 7.73 (1H, td, J=8.4, 1.8 Hz, Ar—H), 8.06 (1H, dd, J=8.1, 1.5 Hz, Ar—H), 8.57 (1H, dd, J=1.8, 0.6 Hz, Ar—H), 9.61 (1H, dd, J=7.8, 1.2 Hz, Ar—H). $^{13}$C NMR (75 MHz, CDCl$_3$): δ (ppm) 27.06, 52.64, 114.95, 123.23, 125.40, 127.27, 127.31, 128.30, 128.68, 128.87, 130.55, 131.81, 131.96, 133.29, 133.70, 144.93, 157.43, 180.86 (CO). HRMS (ESI) m/z calcd for C$_{20}$H$_{15}$N$_2$S$_2$OCl$^+$[M]$^+$ 398.0314. found [M+H]$^+$ 399.0420, [M+H+2]$^+$ 401.0394.

Example 14

10-Chloro-6-(piperidin-1-yl)-12H-thiochromeno[2,3-c]quinolin-12-one (15)

Product 15 was prepared from 3 and piperidine. The yellow solid material was isolated in 86% yield (R$_f$=0.75 at EA). Mp 187-188° C. $^1$H NMR (400 MHz, CDCl$_3$): δ (ppm) 1.71-1.74 (2H, m, —CH$_2$—), 1.88 (4H, p, J=4.5 Hz, —CH$_2$—), 3.31 (4H, t, J=4.2 Hz, —NCH$_2$—), 7.60-7.64 (2H, m, Ar—H), 7.61 (1H, d, J=6.3 Hz, Ar—H), 7.69 (1H, td, J=5.1, 1.2 Hz, Ar—H), 7.99 (1H, dd, J=5.4, 0.6 Hz, Ar—H), 8.58 (1H, d, J=1.5 Hz, Ar—H), 9.62 (1H, dd, J=6.3, 0.6 Hz, Ar—H) $^{13}$C NMR (100 MHz, CDCl$_3$): δ (ppm) 24.27, 25.89, 52.33, 123.47, 125.75, 127.28, 127.85, 128.56, 129.02, 129.23, 130.48, 131.62, 132.16, 132.33, 133.46, 134.67, 144.97, 158.50, 181.51 (CO). HRMS (ESI) calcd for C$_{21}$H$_{17}$N$_2$OSCl [M]$^+$ 380.0750. found [M+H]$^+$ 381.0816.

Example 15

10-Chloro-6-(4-hydroxypiperidin-1-yl)-12H-thiochromeno[2,3-c]quinolin-12-one (16)

Product 16 was prepared from 3 and 4-hydroxypiperidine. The gray-yellow solid material was isolated in 84% yield (R$_f$=0.4 at EA:n-hexane=1:1). Mp 224-225° C. $^1$H NMR (400 MHz, CDCl$_3$): δ (ppm) 1.89 (1H, td, J=7.2, 2.7 Hz, piperidine-CH$_a$), 1.94 (1H, td, J=6.9, 2.7 Hz, piperidine-CH$_a$), 2.15-2.21 (2H, m, piperidine-CH$_e$), 3.19 (2H, td, J=8.4, 2.1 Hz, piperidine-NCH$_a$), 3.60-3.65 (2H, m, piperidine-NCH$_e$), 4.01 (1H, sext, J=3.0 Hz, piperidine-CH), 7.61-7.67 (3H, m, Ar—H), 7.71 (1H, td, J=6.3, 1.2 Hz, Ar—H), 7.99 (1H, dd, J=6.3, 0.6 Hz, Ar—H), 8.59 (1H, dd, J=1.5, 0.6 Hz, Ar—H), 9.64 (1H, dd, J=6.3, 0.6 Hz, Ar—H). $^{13}$C NMR (100 MHz, CDCl$_3$): δ (ppm) 34.49, 48.90, 67.80, 123.62, 125.82, 127.54, 127.88, 128.64, 129.11, 129.36, 130.61, 131.29, 132.20, 132.47, 133.63, 134.43, 144.91, 157.83, 181.47 (CO). HRMS (ESI) calcd for C$_{21}$H$_{17}$N$_2$OSCl [M]$^+$ 396.0699. found [M+H]$^+$ 397.0757.

Example 16

6-(4-Benzylpiperidin-1-yl)-10-chloro-12H-thiochromeno[2,3-c]quinolin-12-one (17)

Product 17 was prepared from 3 and 4-benzylpiperidine. The yellow solid material was isolated in 90% yield (R$_f$=0.57 at CH$_2$Cl$_2$:n-hexane=2:1). Mp 184-185° C. $^1$H NMR (400 MHz, CDCl$_3$): δ (ppm) 1.67 (2H, td, J=9.3, 3.0 Hz, —CH$_2$—), 1.79-1.89 (1H, m, —CH—), 1.88 (2H, d, J=6.9 Hz, piperidine-CH$_2$), 2.71 (2H, d, J=5.1 Hz, piperidine-CH$_2$), 3.00 (2H, td, J=9.3, 1.2 Hz, —NCH$_2$—), 3.65 (2H, d, J=9.3 Hz, —NCH$_2$—), 7.20-7.25 (3H, m, Ar—H), 7.31-7.33 (2H, m, Ar—H), 7.60-7.72 (4H, m, Ar—H), 7.98 (1H, dd, J=6.3, 0.6 Hz, Ar—H), 8.59 (1H, d, J=1.8 Hz, Ar—H), 9.62 (1H, dd, J=6.6, 0.6 Hz, Ar—H). $^{13}$C NMR (100 MHz, CDCl$_3$): δ (ppm) 32.21, 37.88, 43.30, 51.64, 123.52, 125.79, 125.99, 127.36, 127.87, 128.61, 129.09, 129.17, 129.29, 130.55, 131.49, 132.22, 132.41, 133.54, 134.62, 140.46, 144.98, 147.04, 158.25, 181.55 (CO). HRMS (ESI) calcd for C$_{28}$H$_{23}$N$_2$OSCl [M]$^+$ 471.0130. found [M+H]$^+$ 471.1276.

Example 17

6-([1,4'-Bipiperidin]-1'-yl)-10-chloro-12H-thiochromeno[2,3-c]quinolin-12-one (18)

Product 18 was prepared from 3 and 1,4'-bipiperidine. The yellow solid material was isolated in 92% yield (R$_f$=0.15 at EA:MeOH=5:1). Mp 187-189° C. $^1$H NMR (400 MHz, CDCl$_3$): δ (ppm) 1.50-1.52 (2H, m, piperidine-H), 1.66-1.67 (3H, m, piperidine-H), 1.86-1.98 (2H, qd, J=12.4, 2.8 Hz, piperidine-H), 2.06 (2H, d, J=11.6 Hz, piperidine-H), 2.54 (1H, t, J=10.8 Hz, piperidine-H), 2.65 (3H, br, piperidine-H), 3.05 (2H, t, J=12 Hz, piperidine-H), 3.73 (2H, d, J=12.8 Hz, piperidine-H), 7.60-7.66 (3H, m, Ar—H), 7.70 (1H, td, J=8.0, 1.2 Hz, Ar—H), 7.98 (1H, d, J=8.0 Hz, Ar—H), 8.58 (1H, s, Ar—H), 9.62 (1H, d, J=8.8 Hz, Ar—H). $^{13}$C NMR (100 MHz, CDCl$_3$): δ (ppm) 24.79, 26.36, 28.24, 50.45, 51.16, 62.40, 123.57, 125.80, 127.42, 127.86, 128.61, 129.08, 129.30, 130.52, 131.41, 132.18, 132.43, 133.56, 134.54, 144.92, 157.92, 181.47 (CO). HRMS (ESI) calcd for $C_{26}H_{26}N_3OSCl$ [M]$^+$ 463.1485. found [M+H]$^+$ 464.1593.

Example 18

10-Chloro-6-(4-(3-(piperidin-4-yl)propyl)piperidin-1-yl)-12H-thiochromeno[2,3-c]quinolin-12-one (19)

Product 19 was prepared from 3 and 1,3-di(piperidin-4-yl)propane. The yellow solid material was isolated in 76% yield ($R_f$=0.13 at $CH_2Cl_2$). Mp 164-165° C. $^1$H NMR (400 MHz, $CDCl_3$): δ (ppm) 1.16 (2H, qd, J=11.6, 3.2 Hz, —$CH_2$—), 1.20-1.28 (2H, m, —$CH_2$—), 1.36-1.39 (4H, m, —$CH_2$—), 1.51-1.58 (4H, m, —$CH_2$—), 1.70 (2H, d, J=13.6 Hz, —$CH_2$—), 1.87 (2H, d, J=9.6 Hz, —CH2-), 2.43 (1H, br, —NH), 2.60 (2H, td, J=12.0, 2.0 Hz, —$CH_2$—), 2.99 (2H, t, J=11.2 Hz, —$CH_2$—), 3.10 (2H, d, J=12 Hz, —$CH_2$—), 3.64 (2H, d, J=12.4 Hz, —$CH_2$—), 7.59-7.65 (3H, m, Ar—H), 7.68 (1H, td, J=8.0, 1.2 Hz, Ar—H), 8.00 (1H, dd, J=11.2, 1.2 Hz, Ar—H), 8.57 (1H, d, J=1.6 Hz, Ar—H), 9.61 (1H, d, J=8.4 Hz, Ar—H). $^{13}$C NMR (100 MHz, $CDCl_3$): δ (ppm) 23.66, 32.40, 33.24, 35.73, 36.08, 36.86, 37.38, 46.58, 51.76, 123.49, 125.79, 127.30, 127.84, 128.57, 129.05, 129.26, 130.49, 131.55, 132.17, 132.36, 133.50, 134.64, 144.98, 158.34, 181.50 (CO). HRMS (ESI) calcd for $C_{29}H_{32}N_3OSCl$ [M]$^+$ 505.1955. found [M+H]$^+$ 506.2004.

Example 19

10-Chloro-6-(pyrrolidin-1-yl)-12H-thiochromeno[2,3-c]quinolin-12-one (20)

Product 20 was prepared from 3 and pyrrolidine. The solid material was isolated in 86% yield ($R_f$=0.56 at $CH_2Cl_2$:n-hexane=1:1). Mp 170-171° C. $^1$H NMR (300 MHz, $CDCl_3$): δ (ppm) 2.05 (4H, quin, J=3.6 Hz, —$CH_2$—), 3.76 (4H, t, J=6.9 Hz, —$NCH_2$—), 7.50 (1H, td, J=7.2, 1.5 Hz, Ar—H), 7.61 (1H, d, J=1.5 Hz, Ar—$H_{11}$), 7.65 (1H, td, J=7.5, 1.5 Hz, Ar—H), 7.88 (1H, dd, J=8.4, 1.5 Hz, Ar—H), 8.54 (1H, t, J=1.5 Hz, Ar—H), 9.44 (1H, dd, J=8.7, 1.5 Hz, Ar—H). $^{13}$C NMR (75 MHz, $CDCl_3$): δ (ppm) 24.89, 50.52, 121.90, 124.97, 125.17, 126.92, 127.33, 128.42, 128.84, 130.09, 131.77, 131.92, 133.10, 133.32, 144.73, 154.62, 159.91, 181.07 (CO). HRMS (ESI) calcd for $C_{20}H_{15}N_2OSCl$ [M]$^+$ 366.0594. found [M+H]$^+$ 367.0659.

Example 20

10-chloro-6-(2-oxopiperidin-1-yl)-12H-thiochromeno[2,3-c]quinolin-12-one (TC-SCl-B-18) (21)

Product 21 was a yellow solid material which was isolated in 89% yield. Mp: 258-261° C. $^1$H NMR (400 MHz, $CDCl_3$): δ ppm. 1.25 (1H, d, J=4.8 Hz, piperidone-H), 2.44 (2H, quin, —$CH_2$—), 2.61 (1H, s, piperidone-H), 2.75 (2H, t, J=8.4 Hz, —$CH_2$—), 4.11-4.14 (2H, m, —$CH_2$—), 7.60-7.67 (2H, m, Ar—H), 7.78-7.81 (2H, m, Ar—H), 8.09-8.12 (1H, m, Ar—H), 8.60 (1H, d, J=2.0 Hz, Ar—H), 9.72-9.75 (1H, m, Ar—H). $^{13}$C NMR (100 MHz, $CDCl_3$): δ ppm. 19.37, 31.47, 41.05, 49.14, 125.25, 126.08, 127.65, 129.29, 129.51, 129.80, 129.88, 130.74, 131.96, 132.26, 132.74, 133.47, 133.91, 145.05, 148.08, 176.14, 181.01.

Example 21

10-Chloro-6-methylamino-12H-thiochromeno[2,3-c]quinolin-12-one (N1)

Product N1 was prepared from 3 and methylamine. The pure compound was obtained as a yellow solid (yield 92%) ($R_f$=0.65 at $CH_2Cl_2$). Mp 237-238° C. (MeOH). $^1$H NMR (400 MHz, $CDCl_3$): δ (ppm) 3.26 (3H, d, J=4.8 Hz, —$CH_3$), 4.92 (1H, d, J=4.8 Hz, —NH—), 7.45 (1H, td, J=11.2, 1.6 Hz, Ar—H), 7.58 (1H, d, J=8.4 Hz, Ar—H), 7.69-7.65 (2H, m, Ar—H), 7.86 (1H, dd, J=8.4, 0.8 Hz, Ar—H), 8.56 (1H, d, J=1.6 Hz, Ar—H), 9.45 (1H, dd, J=8.4, 1.2 Hz, Ar—H). $^{13}$C NMR (100 MHz, $CDCl_3$): δ (ppm) 29.38, 120.73, 123.68, 124.65, 125.87, 127.18, 127.49, 129.38, 129.51, 129.62, 131.04, 132.50, 132.53, 134.14, 145.64, 151.21, 180.96 (CO). HRMS (ESI) m/z calcd for $C_{17}H_{11}N_2OSCl$ [M]$^+$: 326.0281. found [M+H]$^+$: 327.0356.

Example 22

10-Chloro-6-ethylamino-12H-thiochromeno[2,3-c]quinolin-12-one (N2)

Product N2 was prepared from 3 and ethylamine. The pure compound was obtained as a yellow solid (yield 91%) ($R_f$=0.75 at $CH_2Cl_2$). Mp 204-205° C. (MeOH). $^1$H NMR (400 MHz, $CDCl_3$): δ (ppm) 1.41 (3H, t, J=7.2 Hz, —$CH_3$), 3.75 (2H, q, J=1.6 Hz, —$CH_2$), 4.81 (1H, br, —NH—), 7.44 (1H, td, J=8.4, 1.6 Hz, Ar—H), 7.58-7.64 (3H, m, Ar—H), 7.83 (1H, d, J=8.4 Hz, Ar—H), 8.56 (1H, d, J=1.6 Hz, Ar—H), 9.44 (1H, d, J=8.4 Hz, Ar—H). $^{13}$C NMR (100 MHz, $CDCl_3$): δ (ppm) 14.79, 37.28, 120.70, 123.50, 124.58, 125.84, 127.18, 127.47, 129.39, 129.47, 129.66, 131.08, 132.50, 132.53, 134.12, 145.67, 150.55, 181.00 (CO). HRMS (ESI) m/z calcd for $C_{18}H_{13}N_2OSCl$ [M]$^+$: 340.0437. found [M+H]$^+$: 341.0493.

Example 23

10-Chloro-6-propylamino-12H-thiochromeno[2,3-c]quinolin-12-one (N3)

Product N3 was prepared from 3 and propylamine. The pure compound was obtained as a yellow solid (yield 85%) ($R_f$=0.82 at $CH_2Cl_2$). Mp 178-179° C. (MeOH). $^1$H NMR (400 MHz, $CDCl_3$): δ (ppm) 1.09 (3H, t, J=7.2 Hz, —$CH_3$), 1.81 (2H, sext, J=7.2 Hz, —$CH_2$—), 3.69 (2H, q, J=7.2 Hz, —$NCH_2$—), 4.87 (1H, br, —NH—), 7.44 (1H, td, J=8.0, 1.2 Hz, Ar—H), 7.58-7.64 (3H, m, Ar—H), 7.82 (1H, d, J=8.0 Hz, Ar—H), 8.56 (1H, d, J=1.2 Hz, Ar—H), 9.44 (1H, d, J=8.8 Hz, Ar—H). $^{13}$C NMR (100 MHz, $CDCl_3$): δ (ppm) 11.68, 22.64, 44.13, 120.67, 123.53, 124.53, 125.82, 127.15, 127.46, 129.38, 129.46, 129.65, 131.05, 132.49, 134.10, 145.66, 150.62, 181.02 (CO). HRMS (ESI) m/z calcd for $C_{19}H_{15}N_2OSCl$ [M]$^+$: 354.0594. found [M+H]$^+$: 355.0651.

Example 24

6-(Butylamino)-10-chloro-12H-thiochromeno[2,3-c]quinolin-12-one (N4)

Product N4 was prepared from 3 and butylamine. The pure compound was obtained as a yellow solid (yield 91%) ($R_f$=0.85 at $CH_2Cl_2$). Mp 147-149° C. (MeOH). $^1$H NMR (400 MHz, $CDCl_3$): δ (ppm) 1.03 (3H, t, J=7.2 Hz, —$CH_3$), 1.53 (2H, sext, J=7.2 Hz, —$CH_2$—), 1.76 (2H, quin, J=7.2

Hz, —CH$_2$—), 3.71 (2H, q, J=6.8 Hz, —NCH$_2$—), 4.83 (1H, br, —NH—), 7.43 (1H, td, J=7.6, 1.2 Hz, Ar—H), 7.57-7.64 (3H, m, Ar—H), 7.82 (1H, d, J=8.4 Hz, Ar—H), 8.55 (1H, d, J=1.6 Hz, Ar—H), 9.43 (1H, d, J=8.4 Hz, Ar—H). $^{13}$C NMR (100 MHz, CDCl$_3$): δ (ppm) 13.97, 20.36, 31.54, 42.12, 120.67, 123.53, 124.52, 125.84, 127.16, 127.46, 129.38, 129.46, 129.65, 131.05, 132.48, 132.52, 134.11, 145.68, 150.62, 181.00 (CO). HRMS (ESI) m/z calcd for C$_{20}$H$_{17}$N$_2$OSCl [M]$^+$: 368.0750. found [M+H]$^+$: 369.0846.

Example 25

10-Chloro-6-isobutylamino-12H-thiochromeno[2,3-c]quinolin-12-one (N5)

Product N5 was prepared from 3 and isobutylamine. The pure compound was obtained as a yellow crystal (yield 61%) (R$_f$=0.85 at CH$_2$Cl$_2$). Mp 159-160° C. (MeOH). $^1$H NMR (400 MHz, CDCl$_3$): δ (ppm) 1.08 (6H, d, J=6.8 Hz, —CH$_3$), 2.10 (1H, sep, J=6.8 Hz, —CH), 3.56 (2H, t, J=6.4 Hz, —CH$_2$—), 4.94 (1H, br, —NH), 7.44 (1H, t, J=7.2 Hz, Ar—H), 7.59-7.64 (3H, m, Ar—H), 7.82 (1H, d, J=8.4 Hz, Ar—H), 8.57 (1H, dd, J=2.0, 0.8 Hz, Ar—H), 9.43 (1H, d, J=8.4 Hz, Ar—H). $^{13}$C NMR (100 MHz, CDCl$_3$): δ (ppm) 20.50, 28.16, 49.72, 120.67, 123.54, 124.51, 125.82, 127.13, 127.47, 129.39, 129.47, 129.69, 131.02, 132.50, 134.11, 138.34, 145.62, 150.68, 181.02 (CO). HRMS (ESI) m/z calcd for C$_{20}$H$_{17}$N$_2$OSCl [M]$^+$: 368.0750. found [M+H]$^+$: 369.0825.

Example 26

10-Chloro-6-(pentan-3-ylamino)-12H-thiochromeno[2,3-c]quinolin-12-one (N6)

Product N6 was prepared from 3 and 3-aminopentane. The pure compound was obtained as a light yellow crystal (yield 65%) (R$_f$=0.87 at CH$_2$Cl$_2$). Mp 160-161° C. (MeOH). $^1$H NMR (400 MHz, CDCl$_3$): δ (ppm) 0.92 (6H, t, J=7.6 Hz, —CH$_3$), 1.69 (4H, quin, J=6.0 Hz, —CH$_2$—), 4.34 (1H, sext, J=7.2 Hz, —CH—), 6.58 (1H, d, J=8.0 Hz, Ar—H), 7.36 (1H, t, J=8.0 Hz, Ar—H), 7.58 (1H, t, J=8.0 Hz, Ar—H), 7.65 (1H, d, J=8.0 Hz, Ar—H), 7.90 (1H, dd, J=8.4, 2.4 Hz, Ar—H), 8.01 (1H, d, J=8.4 Hz, Ar—H), 8.40 (1H, d, J=2.4 Hz, Ar—H), 9.34 (1H, d, J=8.8 Hz, Ar—H). $^{13}$C NMR (100 MHz, CDCl$_3$): δ (ppm) 11.21, 26.86, 54.41, 120.16, 123.92, 125.13, 125.81, 127.05, 128.49, 129.02, 129.37, 129.73, 132.17, 132.55, 133.22, 133.29, 145.69, 151.64, 180.85 (CO). HRMS (ESI) m/z calcd for C$_{21}$H$_{19}$N$_2$OSCl [M]$^+$: 382.0907. found [M+H]$^+$: 383.0994, [M–H]$^–$: 381.0851.

Example 27

10-Chloro-6-((2-(dimethylamino)ethyl)amino)-12H-thiochromeno[2,3-c]quinolin-12-one (N7)

Product N7 was prepared from 3 and N,N-dimethylethylenediamine. The pure compound was obtained as a yellow crystal (yield 76%) (R$_f$=0.82 at EA:MeOH:ammonia water=10:5:1). Mp 156-157° C. (MeOH). $^1$H NMR (400 MHz, CDCl$_3$): δ (ppm) 2.36 (6H, s, —N(CH$_3$)$_2$), 2.69 (2H, t, J=6.0 Hz, —CH$_2$N—), 3.57 (2H, q, J=5.6 Hz, —NCH$_2$—), 5.86 (1H, br, —NH), 7.44 (1H, td, J=8.0, 1.6 Hz, Ar—H), 7.62 (2H, td, J=7.6, 1.6 Hz, Ar—H), 7.65 (1H, dd, J=8.0, 0.8 Hz, Ar—H), 7.82 (1H, dd, J=8.4, 1.2 Hz, Ar—H), 8.58 (1H, dd, J=1.6, 0.4 Hz, Ar—H), 9.46 (1H, dd, J=8.8, 1.2 Hz, Ar—H). $^{13}$C NMR (100 MHz, CDCl$_3$): δ (ppm) 39.53, 45.28, 57.57, 120.71, 123.46, 125.90, 127.02, 127.27, 127.57, 129.35, 129.43, 129.56, 131.46, 132.43, 132.56, 134.02, 145.72, 150.90, 181.05 (CO). HRMS (ESI) m/z calcd for C$_{20}$H$_{18}$N$_3$OSCl [M]$^+$: 383.0859. found [M+H]$^+$: 384.0925.

Example 28

10-Chloro-6-((2-(diethylamino)ethyl)amino)-12H-thiochromeno[2,3-c]quinolin-12-one (N8)

Product N8 was prepared from 3 and N,N-diethylethylenediamine. The pure compound was obtained as a yellow crystal (yield 86%) (R$_f$=0.8 at EA:MeOH:ammonia water=10:5:1). Mp 152-153° C. (MeOH). $^1$H NMR (400 MHz, CDCl$_3$): δ (ppm) 1.13 (6H, t, J=7.2 Hz, —CH$_3$), 2.64 (4H, q, J=6.8 Hz, —NCH$_2$—), 2.82 (2H, t, J=6.0 Hz, —CH$_2$N—), 3.70 (2H, q, J=5.2 Hz, —NCH$_2$—), 6.08 (1H, br, —NH—), 7.43 (1H, t, J=7.2 Hz, Ar—H), 7.59-7.64 (3H, m, Ar—H), 7.81 (1H, d, J=8.4 Hz, Ar—H), 8.57 (1H, d, J=1.2 Hz, Ar—H), 9.45 (1H, d, J=8.4 Hz, Ar—H). $^{13}$C NMR (100 MHz, CDCl$_3$): δ (ppm) 12.34, 39.52, 46.81, 50.89, 120.64, 124.25, 124.34, 125.89, 126.96, 127.63, 129.32, 129.41, 129.53, 131.49, 132.37, 132.55, 133.98, 145.79, 150.96, 181.06 (CO). HRMS (ESI) m/z calcd for C$_{22}$H$_{22}$N$_3$OSCl [M]$^+$: 411.1172. found [M+H]$^+$: 412.1262.

Example 29

10-Chloro-6-(2-ethanolamino)-12H-thiochromeno[2,3-c]quinolin-12-one (N9)

Product N9 was prepared from 3 and ethanolamine. The pure compound was obtained as a yellow crystal (yield 77%) (R$_f$=0.65 at EA). Mp 190-192° C. (MeOH). $^1$H NMR (400 MHz, CDCl$_3$): δ (ppm) 3.93 (2H, q, J=4.4 Hz, —NCH$_2$—), 4.00 (2H, t, J=4.4 Hz, —CH$_2$O—), 4.23 (1H, br, —OH), 5.45 (1H, br, —NH), 7.48 (1H, td, J=8.0, 1.6 Hz, Ar—H), 7.62-7.68 (3H, m, Ar—H), 7.81 (1H, dd, J=7.6, 0.8 Hz, Ar—H), 8.58 (1H, dd, J=1.6, 0.4 Hz, Ar—H), 9.45 (1H, dd, J=8.4, 0.8 Hz, Ar—H). $^{13}$C NMR (100 MHz, CDCl$_3$): δ (ppm) 45.88, 63.59, 120.97, 123.67, 125.12, 125.92, 126.60, 127.50, 129.48, 129.83, 130.15, 130.91, 132.55, 132.69, 134.35, 144.65, 151.32, 180.87 (CO). HRMS (ESI) m/z calcd for C$_{18}$H$_{13}$N$_2$O$_2$SCl [M]$^+$: 356.8260. found [M+H]$^+$: 357.0476, [M+H+2]$^+$: 359.0455.

Example 30

10-Chloro-6-(3-propanolamino)-12H-thiochromeno[2,3-c]quinolin-12-one (N10)

Product N10 was prepared from 3 and 3-amino-1-propanol. The pure compound was obtained as a yellow solid (yield 94%) (R$_f$=0.66 at EA). Mp 201-202° C. (MeOH). $^1$H NMR (400 MHz, CDCl$_3$): δ (ppm) 1.94 (2H, p, J=6.0 Hz, —CH$_2$—), 3.72 (2H, t, J=5.2 Hz, —NCH$_2$—), 3.93 (2H, q, J=6.0 Hz, —CH$_2$O—), 4.41 (1H, br, —OH), 5.38 (1H, t, J=5.2 Hz, —NH—), 7.45 (1H, td, J=7.6, 1.2 Hz, Ar—H), 7.58-7.65 (3H, m, Ar—H), 7.78 (1H, dd, J=8.4, 0.8 Hz, Ar—H), 8.56 (1H, dd, J=2.0, 0.4 Hz, Ar—H), 9.42 (1H, dd, J=8.4, 1.2 Hz, Ar—H). $^{13}$C NMR (100 MHz, CDCl$_3$): δ (ppm) 33.23, 38.94, 59.25, 120.72, 123.44, 124.84, 125.94, 126.32, 127.45, 129.44, 129.92, 130.11, 130.84, 132.49, 132.64, 134.31, 144.83, 151.33, 180.88 (CO). HRMS (ESI) m/z calcd for C$_{19}$H$_{15}$N$_2$O$_2$SCl [M]$^+$: 370.0543. found [M+H]$^+$: 371.0622.

Example 31

10-Chloro-6-(5-pentanolamino)-12H-thiochromeno[2,3-c]quinolin-12-one (N11)

Product N11 was prepared from 3 and 5-amino-1-pentanol. The pure compound was obtained as a yellow solid (yield 91%) ($R_f$=0.7 at EA). Mp 158-160° C. (MeOH). $^1$H NMR (400 MHz, CDCl$_3$): δ (ppm) 1.40 (1H, br, —OH), 1.49-1.62 (2H, m, —CH$_2$—), 1.71 (2H, quin, —CH$_2$—), 1.83 (2H, quin, —CH$_2$—), 3.74 (4H, quin, —CH$_2$—), 4.91 (1H, br, —NH), 7.45 (1H, td, J=7.6, 1.2 Hz, Ar—H), 7.59 (3H, m, Ar—H), 7.83 (1H, d, J=8.4 Hz, Ar—H), 8.57 (1H, d, J=1.2 Hz, Ar—H), 9.44 (1H, d, J=8.4 Hz, Ar—H). $^{13}$C NMR (100 MHz, CDCl$_3$): δ (ppm) 23.39, 29.17, 32.40, 42.24, 62.83, 120.69, 123.53, 124.60, 125.84, 127.11, 127.48, 129.40, 129.51, 129.71, 131.02, 131.79, 132.53, 134.14, 145.60, 150.58, 181.02 (CO). HRMS (ESI) m/z calcd for C$_{21}$H$_{19}$N$_2$O$_2$SCl [M]$^+$: 398.0856. found [M+H]$^+$: 399.0914.

Example 32

10-Chloro-6-((1-hydroxybutan-2-yl)amino)-12H-thiochromeno[2,3-c]quinolin-12-one (N12)

Product N12 was prepared from 3 and 2-amino-1-butanol. The pure compound was obtained as a yellow solid (yield 94%) ($R_f$=0.8 at EA). Mp 203-204° C. (MeOH). $^1$H NMR (400 MHz, CDCl$_3$): δ (ppm) 1.21 (3H, t, J=7.6 Hz, —CH$_3$), 1.71-1.88 (2H, m, —CH$_2$—), 3.79 (1H, dd, J=11.2, 1.6 Hz, —CH$_2$—), 3.99 (1H, dd, J=11.2, 2.8 Hz, —CH$_2$—), 4.34 (1H, quin, J=11.2 Hz, —NCH—), 4.59 (1H, br, —OH), 5.02 (1H, d, J=6.0 Hz, —NH—), 7.44 (1H, td, J=8.0, 1.2 Hz, Ar—H), 7.56 (1H, d, J=8.4 Hz, Ar—H), 7.59 (1H, td, J=7.6, 1.2 Hz, Ar—H), 7.61 (1H, d, J=8.4 Hz, Ar—H), 7.74 (1H, d, J=8.4 Hz, Ar—H), 8.52 (1H, d, J=2.0 Hz, Ar—H), 9.40 (1H, dd, J=7.6, 1.2 Hz, Ar—H). $^{13}$C NMR (100 MHz, CDCl$_3$): δ (ppm) 10.95, 24.95, 56.89, 67.08, 120.83, 123.68, 124.98, 125.88, 126.51, 127.40, 129.39, 129.75, 130.02, 130.81, 132.38, 132.62, 134.28, 144.53, 151.09, 180.75 (CO). HRMS (ESI) m/z calcd for C$_{20}$H$_{17}$N$_2$O$_2$SCl [M]$^+$: 384.0699. found [M+H]$^+$: 385.0790.

Example 33

10-Chloro-6-((4-methylpentan-2-yl)amino)-12H-thiochromeno[2,3-c]quinolin-12-one (N13)

Product N13 was prepared from 3 and 4-methylpentan-2-amine. The pure compound was obtained as a yellow solid (yield 94%) ($R_f$=0.9 at CH$_2$Cl$_2$). Mp 176-177° C. (MeOH). $^1$H NMR (400 MHz, CDCl$_3$): δ (ppm) 0.98 (3H, d, J=6.8 Hz, —CH$_3$), 1.03 (3H, d, J=6.8 Hz, —CH$_3$), 1.35 (3H, d, J=6.4 Hz, —CH$_3$), 1.45 (1H, quin, J=6.4 Hz, —CH$_2$—), 1.66 (1H, quin, J=6.8 Hz, —CH$_2$—), 1.80 (1H, sep, J=6.8 Hz, —CH—), 4.63 (1H, br, —NH), 4.63-4.66 (1H, m, —CH—), 7.43 (1H, td, J=7.6, 1.2 Hz, Ar—H), 7.58-7.63 (3H, m, Ar—H), 7.81 (1H, d, J=8.4 Hz, Ar—H), 8.56 (1H, d, J=1.2 Hz, Ar—H), 9.43 (1H, d, J=8.4 Hz, Ar—H). $^{13}$C NMR (100 MHz, CDCl$_3$): δ (ppm) 21.38, 22.87, 22.92, 25.40, 45.73, 46.80, 120.55, 123.42, 124.36, 125.80, 127.21, 127.44, 129.38, 129.71, 131.08, 132.47, 132.52, 134.07, 145.76, 150.01, 181.05 (CO). HRMS (ESI) m/z calcd for C$_{22}$H$_{19}$N$_2$OSCl [M]$^+$: 396.1063. found [M+H]$^+$: 397.1142.

Example 34

6-((2-Aminoethyl)amino)-10-chloro-12H-thiochromeno[2,3-c]quinolin-12-one (N14)

Product N14 was prepared from 3 and 1,2-diaminoethane. The pure compound was obtained as a yellow solid (yield 90%) ($R_f$=0.6 at EA:MeOH:ammonia water=10:5:1). Mp 193-194° C. (MeOH). $^1$H NMR (400 MHz, DMSO-d$_6$): δ (ppm) 2.90 (2H, t, J=6.0 Hz, —CH$_2$—), 3.59 (2H, t, J=6.0 Hz, —CH$_2$—), 7.36 (1H, t, J=8.0 Hz, Ar—H), 7.59 (1H, t, J=8.0 Hz, Ar—H), 7.66 (1H, d, J=8.0 Hz, Ar—H), 7.85 (1H, d, J=7.2 Hz, Ar—H), 7.96 (1H, d, J=8.8 Hz, Ar—H), 8.35 (1H, br, Ar—H), 9.32 (1H, d, J=8.4 Hz, Ar—H). $^{13}$C NMR (100 MHz, DMSO-d$_6$): δ (ppm) 40.79, 45.06, 120.24, 124.08, 125.31, 125.84, 127.00, 128.39, 128.83, 129.32, 129.69, 132.06, 132.33, 133.12, 133.26, 145.58, 151.52, 180.65 (CO). HRMS (ESI) m/z calcd for C$_{18}$H$_{14}$N$_3$OSCl [M]$^+$: 355.0546. found [M+H]$^+$: 356.0641.

Example 35

10-Chloro-6-((2-((2-hydroxyethyl)amino)ethyl)amino)-12H-thiochromeno[2,3-c]quinolin-12-one (N15)

Product N15 was prepared from 3 and N-(2-hydroxyethyl)ethylenediamine. The pure compound was obtained as a yellow solid (yield 58%) ($R_f$=0.63 at EA:MeOH:ammonia water=10:5:1). Mp 141-143° C. (MeOH). $^1$H NMR (400 MHz, DMSO-d$_6$): δ (ppm) 2.69 (2H, t, J=5.6 Hz, —CH$_2$—), 2.90 (2H, t, J=6.0 Hz, —CH$_2$—), 3.51 (2H, t, J=5.6 Hz, —CH$_2$—), 3.65 (2H, t, J=6.0 Hz, —CH$_2$—), 7.10 (1H, br, —NH—), 7.32 (1H, t, J=7.2 Hz, Ar—H), 7.55 (1H, t, J=7.2 Hz, Ar—H), 7.62 (1H, d, J=8.4 Hz, Ar—H), 7.76 (1H, t, J=7.2 Hz, Ar—H), 7.86 (1H, d, J=8.4 Hz, Ar—H), 8.25 (1H, d, J=2.0 Hz, Ar—H), 9.26 (1H, d, J=8.4 Hz, Ar—H). $^{13}$C NMR (100 MHz, DMSO-d$_6$): δ (ppm) 41.90, 48.16, 51.80, 60.72, 120.13, 123.96, 125.14, 125.81, 126.94, 128.26, 128.65, 129.16, 129.60, 131.82, 132.11, 132.96, 133.19, 145.50, 151.35, 180.45 (CO). HRMS (ESI) m/z calcd for C$_{20}$H$_{18}$N$_3$O$_2$SCl [M]$^+$: 399.8938. found [M+H]$^+$: 400.0880.

Example 36

10-Chloro-6-((2-morpholinoethyl)amino)-12H-thiochromeno[2,3-c]quinolin-12-one (N16)

Product N16 was prepared from 3 and 4-(2-aminoethyl)morpholine. The pure compound was obtained as a yellow solid (yield 87%) ($R_f$=0.48 at EA). Mp 189-190° C. (MeOH). $^1$H NMR (400 MHz, CDCl$_3$): δ (ppm) 2.63 (4H, br, —CH$_2$—), 2.81 (2H, br, —CH$_2$—), 3.81 (6H, br, —CH$_2$—), 5.92 (1H, br, —NH—), 6.70 (2H, d, J=8.4 Hz, Ar'—H), 7.45 (1H, td, J=7.8, 1.6 Hz, Ar—H), 7.60-7.64 (3H, m, Ar—H), 7.81 (1H, d, J=8.4 Hz, Ar—H), 8.57 (1H, s, Ar—H), 9.46 (1H, dd, J=8.8, 1.2 Hz, Ar—H). $^{13}$C NMR (100 MHz, CDCl$_3$): δ (ppm) 38.28, 53.31, 56.52, 67.13, 120.73, 123.94, 124.58, 125.91, 127.01, 127.56, 129.37, 129.49, 129.64, 131.27, 132.47, 132.54, 134.10, 145.66, 150.76, 180.99 (CO). HRMS (ESI) m/z calcd for C$_{22}$H$_{20}$N$_3$O$_2$SCl [M]$^+$: 425.0965. found [M+H]$^+$: 426.1058, [M−H]$^-$: 424.0885.

Example 37

10-Chloro-6-((3-(dimethylamino)propyl)amino)-12H-thiochromeno[2,3-c]quinolin-12-one (N17)

Product N17 was prepared from 3 and 3-(dimethylamino)-1-propylamine. The pure compound was obtained as a yellow crystal (yield 43%) (R$_f$=0.71 at EA:MeOH:ammonia water=10:5:1). Mp 194-195° C. (MeOH). $^1$H NMR (400 MHz, CDCl$_3$): δ (ppm) 1.92 (2H, quin, J=6.0 Hz, —CH$_2$—), 2.41 (6H, s, —N(CH$_3$)$_2$), 2.60 (2H, t, J=5.6 Hz, —CH$_2$N—), 3.81 (2H, q, J=5.6 Hz, —NCH$_2$—), 7.95 (1H, br, —NH), 7.40 (1H, td, J=7.6, 1.6 Hz, Ar—H), 7.56-7.63 (4H, m, Ar—H), 7.80 (1H, d, J=8.4 Hz, Ar—H), 8.57 (1H, d, J=2.4 Hz, Ar—H), 9.44 (1H, dd, J=7.6, 0.8 Hz, Ar—H). $^{13}$C NMR (100 MHz, CDCl$_3$): δ (ppm) 24.83, 43.64, 45.68, 59.72, 120.46, 123.97, 124.56, 125.84, 126.83, 127.54, 129.32, 129.48, 131.84, 132.29, 132.56, 133.86, 146.01, 151.27, 181.14 (CO). HRMS (ESI) m/z calcd for C$_{21}$H$_{20}$N$_3$OSCl [M]$^+$: 397.1016. found [M+H]$^+$: 398.1072.

Example 38

10-Chloro-6-((3-(diethylamino)propyl)amino)-12H-thiochromeno[2,3-c]quinolin-12-one (N18)

Product N18 was prepared from 3 and 3-(diethylamino)-1-propylamine. The pure compound was obtained as a yellow acicular crystal (yield 70%) (R$_f$=0.68 at EA:MeOH:ammonia water=10:5:1). Mp 142-143° C. (MeOH). $^1$H NMR (400 MHz, CDCl$_3$): δ (ppm) 1.15 (6H, t, J=6.8 Hz, —CH$_3$), 1.91 (2H, quin, J=6.0 Hz, —CH$_2$—), 2.66-2.72 (6H, m, —NCH$_2$—), 3.81 (2H, q, J=4.8 Hz, —NCH$_2$—), 7.40 (1H, td, J=7.2, 1.2 Hz, Ar—H), 7.55-7.58 (1H, dd, J=8.4, 3.6 Hz, Ar—H), 7.60-7.64 (2H, m, Ar—H), 7.81 (1H, d, J=8.0 Hz, Ar—H), 7.93 (1H, br, Ar—H), 8.58 (1H, t, J=2.0 Hz, Ar—H), 9.45 (1H, dd, J=8.4, 0.8 Hz, Ar—H). $^{13}$C NMR (100 MHz, CDCl$_3$): δ (ppm) 11.44, 24.71, 44.25, 47.09, 53.57, 120.45, 123.99, 124.50, 125.86, 126.87, 127.46, 129.34, 129.43, 131.85, 132.32, 132.57, 133.88, 146.04, 151.30, 181.15 (CO). HRMS (ESI) m/z calcd for C$_{23}$H$_{24}$N$_3$SOCl [M]$^+$: 425.1329. found [M+H]$^+$: 426.1396, [M−H]$^−$: 424.1284.

Example 39

10-Chloro-6-((3-((2-hydroxyethyl)amino)propyl)amino)-12H-thiochromeno[2,3-c]quinolin-12-one (N19)

Product N19 was prepared from 3 and N-(2-Hydroxyethyl)-1,3-diaminopropane. The pure compound was obtained as a brown solid (yield 75%) (R$_f$=0.65 at EA:MeOH:ammonia water=10:5:1). Mp 65-67° C. (MeOH). $^1$H NMR (400 MHz, CDCl$_3$): δ (ppm) 1.89 (2H, quin, J=6.0 Hz, —CH$_2$—), 2.15 (2H, br, —OH & —NH—), 2.85 (4H, quin, —CH$_2$—), 3.74 (2H, t, J=6.0 Hz, —CH$_2$—), 3.80 (2H, t, J=5.2 Hz, —CH$_2$—), 6.53 (1H, br, —NH—), 7.39 (1H, td, J=7.6, 0.8 Hz, Ar—H), 7.44 (1H, d, J=8.8 Hz, Ar—H), 7.50 (1H, dd, J=8.4, 2.4 Hz, Ar—H), 7.58 (1H, td, J=7.2, 1.2 Hz, Ar—H), 7.76 (1H, d, J=8.0 Hz, Ar—H), 8.46 (1H, d, J=2.0 Hz, Ar—H), 9.39 (1H, d, J=8.4 Hz, Ar—H). $^{13}$C NMR (100 MHz, CDCl$_3$): δ (ppm) 28.37, 42.23, 48.74, 51.65, 61.42, 120.48, 123.99, 124.22, 125.85, 126.88, 127.42, 129.13, 129.33, 129.38, 131.23, 132.21, 132.33, 133.95, 145.69, 150.82, 180.92 (CO). HRMS (ESI) m/z calcd for C$_{21}$H$_{20}$N$_3$O$_2$SCl [M]$^+$: 413.0965. found [M+H]$^+$: 414.1053, [M+H+2]$^+$: 416.1037.

Example 40

10-Chloro-6-((2,3-dihydro-1H-inden-2-yl)amino)-12H-thiochromeno[2,3-c]quinolin-12-one (N20)

Product N20 was prepared from 3 and 2-aminoindane. The pure compound was obtained as a brown solid (yield 65%) (R$_f$=0.7 at CH$_2$Cl$_2$:n-hexane=2:1). Mp 251-252° C. (MeOH). $^1$H NMR (400 MHz, CDCl$_3$): δ (ppm) 3.02 (1H, d, J=5.2 Hz, indane-H), 3.06 (1H, d, J=5.2 Hz, indane-H), 3.59 (1H, d, J=7.2 Hz, indane-H), 3.63 (1H, d, J=7.2 Hz, indane-H), 5.10 (1H, d, J=6.8 Hz, —NH), 5.23 (1H, q, J=5.2 Hz, indane-H), 7.21-7.25 (2H, m, Ar'—H), 7.28-7.31 (2H, m, Ar'—H), 7.47 (1H, td, J=6.8, 1.2 Hz, Ar—H), 7.58 (1H, d, J=8.4 Hz, Ar—H), 7.61-7.67 (1H, td, J=6.8, 1.2 Hz, Ar—H), 7.87 (1H, d, J=7.6 Hz, Ar—H), 8.57 (1H, d, J=2.0 Hz, Ar—H), 9.46 (1H, dd, J=8.8, 0.8 Hz, Ar—H). $^{13}$C NMR (100 MHz, CDCl$_3$): δ (ppm) 40.41, 53.27, 120.79, 123.60, 124.81, 124.93, 125.84, 126.76, 127.37, 127.46, 129.38, 129.51, 129.71, 131.02, 132.50, 132.54, 134.12, 141.29, 145.56, 150.20, 181.00 (CO). HRMS (ESI) m/z calcd for C$_{25}$H$_{17}$N$_2$OSCl [M]$^+$: 428.0750. found [M+H]$^+$: 429.0822.

Example 41

10-Chloro-6-(cyclohexylamino)-12H-thiochromeno[2,3-c]quinolin-12-one (N21)

Product N21 was prepared from 3 and cyclohexylamine. The pure compound was obtained as a brown solid (yield 91%) (R$_f$=0.7 at CH$_2$Cl$_2$:n-hexane=2:1). Mp 196-197° C. (MeOH). $^1$H NMR (400 MHz, CDCl$_3$): δ (ppm) 1.25-1.40 (4H, m, cyclohexylamine-CH$_2$), 1.49-1.60 (2H, m, cyclohexylamine-CH$_2$), 1.70-1.74 (2H, m, cyclohexylamine-CH$_2$), 1.79-1.84 (2H, m, cyclohexylamine-CH$_2$), 2.21 (2H, dd, J=8.8, 3.2 Hz, cyclohexylamine-CH$_2$), 4.30 (1H, sep, J=3.6 Hz, cyclohexylamine-CH), 4.72 (1H, d, J=6.8 Hz, —NH—), 7.41 (1H, t, J=8.0 Hz, Ar—H), 7.51-62 (3H, m, Ar—H), 7.79 (1H, d, J=8.0 Hz, Ar—H), 8.51 (1H, d, J=1.6 Hz, Ar—H), 9.41 (1H, d, J=8.4 Hz, Ar—H). $^{13}$C NMR (100 MHz, CDCl$_3$): δ (ppm) 24.94, 25.92, 33.10, 50.26, 120.51, 123.50, 124.34, 125.77, 127.11, 127.37, 129.27, 129.35, 129.60, 131.01, 132.37, 132.41, 134.00, 145.66, 149.75, 180.95 (CO). HRMS (ESI) m/z calcd for C$_{22}$H$_{19}$N$_2$OSCl [M]$^+$: 394.0907. found [M+H]$^+$: 395.0991.

Example 42

6-((1-Benzylpiperidin-4-yl)amino)-10-chloro-12H-thiochromeno[2,3-c]quinolin-12-one (N22)

Product N22 was prepared from 3 and 1-benzylpiperidin-4-amine. The pure compound was obtained as a brown solid (yield 62%) (R$_f$=0.77 at EA). Mp 194-196° C. (MeOH). $^1$H NMR (400 MHz, CDCl$_3$): δ (ppm) 1.62-1.72 (2H, m, piperidine-H), 2.24 (2H, d, J=13.2 Hz, piperidine-H), 2.32 (2H, t, J=11.2 Hz, piperidine-H), 2.92 (2H, d, J=11.6 Hz, piperidine-H), 3.59 (2H, s, —CH$_2$—), 4.35 (1H, sext, J=6.4 Hz, piperidine-CH), 4.75 (1H, d, J=7.2 Hz, —NH), 7.26-7.30 (1H, m, Ar'—H), 7.36-7.38 (4H, m, Ar'—H), 7.44 (1H, td, J=7.6, 0.8 Hz, Ar—H), 7.59-7.64 (3H, m, Ar—H), 7.80 (1H, d, J=7.6 Hz, Ar—H), 8.56 (1H, d, J=1.6 Hz, Ar—H), 9.43 (1H, d, J=8.8 Hz, Ar—H). $^{13}$C NMR (100 MHz, CDCl$_3$): δ (ppm) 32.26, 48.63, 52.35, 63.22, 120.63, 123.47, 124.57, 125.81, 127.07, 127.12, 127.47, 128.25, 129.21, 129.35, 129.44, 129.74, 130.99, 132.46, 132.52, 134.10, 138.37, 145.57, 149.76, 181.00 (CO). HRMS (ESI) m/z calcd for C$_{28}$H$_{24}$N$_3$OSCl [M]$^+$: 485.1329. found [M+H]$^+$: 486.1379.

Example 43

10-Chloro-6-((thiophen-2-ylmethyl)amino)-12H-thiochromeno[2,3-c]quinolin-12-one (N23)

Product N23 was prepared from 3 and 2-thiophenemethylamine. The pure compound was obtained as a brown solid (yield 78%) ($R_f$=0.7 at $CH_2Cl_2$:n-hexane=2:1). Mp 178-180° C. (MeOH). $^1$H NMR (400 MHz, $CDCl_3$): δ (ppm) 5.07 (1H, d, J=5.2 Hz, —$NCH_2$—), 5.17 (1H, br, —NH—), 7.00 (1H, t, J=4.4 Hz, thiophene-H), 7.16 (1H, d, J=3.2 Hz, thiophene-H), 7.25 (1H, d, J=0.8 Hz, thiophene-H), 7.47 (1H, t, J=8.0 Hz, Ar—H), 7.52 (1H, d, J=8.4 Hz, Ar—H), 7.58 (1H, d, J=8.4 Hz, Ar—H), 7.65 (1H, t, J=7.6 Hz, Ar—H), 7.89 (1H, d, J=8.0 Hz, Ar—H), 8.53 (1H, s, Ar—H), 9.46 (1H, d, J=8.4 Hz, Ar—H). $^{13}$C NMR (100 MHz, $CDCl_3$): δ (ppm) 41.14, 121.06, 123.58, 125.05, 125.47, 125.89, 126.47, 126.73, 127.29, 127.45, 129.33, 129.57, 129.71, 130.94, 132.39, 132.51, 134.12, 141.36, 145.20, 149.82, 180.80 ($\underline{C}$O). HRMS (ESI) m/z calcd for $C_{21}H_{13}N_2OS_2Cl$ [M]$^+$: 408.0158. found [M+H]$^+$: 409.0251, [M–H]$^-$: 407.0085.

Example 44

10-Chloro-6-((cyclohexylmethyl)amino)-12H-thiochromeno[2,3-c]quinolin-12-one (N24)

Product N24 was prepared from 3 and cyclohexylmethanamine. The pure compound was obtained as a brown solid (yield 79%) ($R_f$=0.7 at $CH_2Cl_2$:n-hexane=2:1). Mp 165-166° C. (MeOH). $^1$H NMR (400 MHz, $CDCl_3$): δ (ppm) 1.07 (1H, d, J=11.2 Hz, cyclohexyl-$CH_2$), 1.30 (1H, d, J=11.2 Hz, cyclohexyl-$CH_2$), 1.23 (2H, q, J=11.6 Hz, cyclohexyl-$CH_2$), 1.31 (2H, q, J=11.6 Hz, cyclohexyl-$CH_2$), 1.78-1.81 (4H, m, cyclohexyl-$CH_2$), 1.90 (2H, d, J=12.4 Hz, cyclohexyl-$CH_2$), 3.53 (2H, t, J=6.0 Hz, —$NCH_2$—), 4.85 (1H, br, —NH—), 7.40 (1H, t, J=7.2 Hz, Ar—H), 7.51 (1H, d, J=8.8 Hz, Ar—H), 7.55 (1H, d, J=1.6 Hz, Ar—H), 7.60 (1H, t, J=8.0 Hz, Ar—H), 7.79 (1H, d, J=8.0 Hz, Ar—H), 8.50 (1H, d, J=1.2 Hz, Ar—H), 9.41 (1H, d, J=8.4 Hz, Ar—H). $^{13}$C NMR (100 MHz, $CDCl_3$): δ (ppm) 25.97, 26.52, 31.23, 37.63, 48.50, 120.59, 123.57, 124.41, 125.80, 127.10, 127.38, 129.26, 129.38, 129.45, 130.95, 132.33, 132.41, 134.02, 145.58, 150.64, 180.87 ($\underline{C}$O). HRMS (ESI) m/z calcd for $C_{23}H_{21}N_2OCl$ [M]$^+$: 408.1063. found [M+H]$^+$: 409.1115.

Example 45

6-(Benzylamino)-10-chloro-12H-thiochromeno[2,3-c]quinolin-12-one (N25)

Product N25 was prepared from 3 and benzylamine. The pure compound was obtained as a brown solid (yield 93%) ($R_f$=0.67 at $CH_2Cl_2$:n-hexane=2:1). Mp 194-195° C. (MeOH). $^1$H NMR (400 MHz, $CDCl_3$): δ (ppm) 4.94 (2H, d, J=5.2 Hz, —$CH_2$—), 5.16 (1H, br, —NH—), 7.33-7.51 (6H, m, Ar—H), 7.58-7.67 (3H, m, Ar—H), 7.87 (1H, d, J=8.0 Hz, Ar—H), 8.59 (1H, d, J=2.0 Hz, Ar—H), 9.47 (1H, d, J=8.0 Hz, Ar—H). $^{13}$C NMR (100 MHz, $CDCl_3$): δ (ppm) 37.63, 120.98, 123.54, 124.89, 125.87, 127.26, 127.50, 127.63, 128.24, 128.79, 129.43, 129.57, 129.85, 131.02, 132.58, 134.18, 138.82, 145.48, 150.33, 181.00 ($\underline{C}$O). HRMS (ESI) m/z calcd for $C_{23}H_{15}N_2OSCl$ [M]$^+$: 402.0594. found [M+H]$^+$: 403.0692.

Example 46

10-Chloro-6-((pyridin-2-ylmethyl)amino)-12H-thiochromeno[2,3-c]quinolin-12-one (N26)

Product N26 was prepared from 3 and 2-picolylamine. The pure compound was obtained as a brown solid (yield 93%) ($R_f$=0.25 at EA). Mp 187-189° C. (MeOH). $^1$H NMR (400 MHz, $CDCl_3$): δ (ppm) 5.01 (2H, d, J=4.0 Hz, —$CH_2$—), 6.79 (1H, br, —NH—), 7.24-7.28 (1H, m, Ar'—H), 7.45 (2H, t, J=7.2 Hz, Ar'—H & Ar—H), 7.61-7.67 (3H, m, Ar—H), 7.73 (1H, td, J=7.6, 1.6 Hz, Ar—H), 7.86 (1H, d, J=8.4 Hz, Ar—H), 8.58 (1H, d, J=2.0 Hz, Ar—H), 8.67 (1H, d, J=4.8 Hz, Ar'—H), 9.47 (1H, d, J=8.4 Hz, Ar—H). $^{13}$C NMR (100 MHz, $CDCl_3$): δ (ppm) 46.74, 120.81, 122.37, 124.19, 124.61, 125.93, 127.04, 127.60, 129.33, 129.44, 129.60, 131.40, 132.46, 132.52, 134.03, 136.94, 145.62, 148.94, 150.43, 156.58, 181.00 ($\underline{C}$O). HRMS (ESI) m/z calcd for $C_{22}H_{14}N_3OSCl$ [M]$^+$: 403.0546. found [M+H]$^+$: 404.0615.

Example 47

6-((Benzo[d][1,3]dioxol-5-ylmethyl)amino)-10-chloro-12H-thiochromeno[2,3-c]quinolin-12-one (N27)

Product N27 was prepared from 3 and piperonylamine. The pure compound was obtained as a brown solid (yield 90%) ($R_f$=0.88 at EA). Mp 205-206° C. (MeOH). $^1$H NMR (400 MHz, $CDCl_3$): δ (ppm) 4.82 (2H, t, J=5.2 Hz, —$NCH_2$—), 5.08 (1H, br, —NH—), 5.97 (2H, s, —$OCH_2O$—), 6.82 (1H, d, J=8.0 Hz, Ar'—H), 6.96 (1H, d, J=8.0 Hz, Ar'—H), 7.00 (1H, d, J=1.2 Hz, Ar'—H), 7.47 (1H, td, J=8.0, 1.2 Hz, Ar—H), 7.57 (1H, d, J=8.8 Hz, Ar—H), 7.60-7.66 (2H, m, Ar—H), 7.86 (1H, d, J=8.0 Hz, Ar—H), 8.62 (1H, d, J=2.0 Hz, Ar—H), 9.46 (1H, d, J=8.8 Hz, Ar—H). $^{13}$C NMR (100 MHz, $CDCl_3$): δ (ppm) 46.30, 101.10, 108.40, 108.85, 120.95, 121.58, 123.52, 124.88, 125.86, 127.23, 127.46, 129.39, 129.56, 129.76, 130.98, 132.48, 132.55, 132.61, 134.15, 145.42, 147.07, 147.92, 150.21, 180.93 ($\underline{C}$O). HRMS (ESI) m/z calcd for $C_{24}H_{15}N_2O_3SCl$ [M]$^+$: 446.0492. found [M+H]$^+$: 447.0586, [M–H]$^-$: 445.0440.

Example 48

10-Chloro-6-((2-methoxybenzyl)amino)-12H-thiochromeno[2,3-c]quinolin-12-one (N28)

Product N28 was prepared from 3 and 2-methoxybenzylamine. The pure compound was obtained as a brown solid (yield 82%) ($R_f$=0.65 at $CH_2Cl_2$:n-hexane=2:1). Mp 223-224° C. (MeOH). $^1$H NMR (400 MHz, $CDCl_3$): δ (ppm) 3.95 (3H, s, —$OCH_3$), 4.93 (2H, d, J=5.6 Hz, —$NCH_2$—), 5.57 (1H, t, J=5.6 Hz, —NH—), 5.97 (2H, s, —$OCH_2O$—), 6.94-7.00 (2H, m, Ar'—H), 7.30 (1H, td, J=8.0, 2.0 Hz, Ar'—H), 7.45 (1H, td, J=8.0, 1.6 Hz, Ar'—H), 7.51 (1H, d, J=7.2 Hz, Ar'—H), 7.59-7.66 (3H, m, Ar—H), 7.89 (1H, dd, J=8.4, 1.2 Hz, Ar—H), 8.57 (1H, dd, J=2.0, 0.8 Hz, Ar—H), 9.45 (1H, dd, J=8.4, 0.8 Hz, Ar—H). $^{13}$C NMR (100 MHz, $CDCl_3$): δ (ppm) 42.33, 55.49, 110.47, 120.68, 120.81, 123.90, 124.59, 125.82, 126.68, 127.20, 127.52, 128.88, 129.38, 129.44, 129.71, 130.49, 131.23, 132.46, 132.54, 134.04, 145.59, 150.62, 157.89, 181.04 ($\underline{C}$O). HRMS (ESI) m/z calcd for $C_{24}H_{17}N_2O_2SCl$ [M]$^+$: 432.0699. found [M+H]$^+$: 433.0783.

Example 49

10-Chloro-6-((3,4-dimethoxybenzyl)amino)-12H-thiochromeno[2,3-c]quinolin-12-one (N29)

Product N29 was prepared from 3 and 3,4-dimethoxybenzylamine. The pure compound was obtained as a brown solid (yield 84%) ($R_f$=0.66 at $CH_2Cl_2$:n-hexane=2:1). Mp 251-252° C. (MeOH). $^1$H NMR (400 MHz, $CDCl_3$): δ (ppm) 3.89 (3H, s, —$OCH_3$), 3.90 (3H, s, —$OCH_3$), 4.86 (2H, d, J=4.8

Hz, —NCH$_2$—), 5.11 (1H, t, J=5.2 Hz, —NH—), 6.89 (1H, d, J=8.0 Hz, Ar'—H), 7.05 (1H, dd, J=8.0, 2.0 Hz, Ar'—H), 7.08 (1H, d, J=2.0 Hz, Ar'—H), 7.48 (1H, td, J=7.6, 1.2 Hz, Ar—H), 7.60 (1H, dd, J=8.4, 0.4 Hz, Ar—H), 7.65 (1H, dd, J=8.4, 1.5 Hz, Ar—H), 7.66 (1H, td, J=8.0, 1.2 Hz, Ar—H), 7.88 (1H, dd, J=8.4, 0.8 Hz, Ar—H), 8.59 (1H, dd, J=1.5, 0.4 Hz, Ar—H), 9.48 (1H, dd, J=8.4, 1.2 Hz, Ar—H). $^{13}$C NMR (100 MHz, CDCl$_3$): δ (ppm) 46.45, 55.96, 55.99, 111.31, 111.82, 120.59, 120.99, 123.56, 124.88, 125.91, 127.20, 127.50, 129.45, 129.60, 129.88, 131.04, 131.34, 132.59, 134.21, 145.52, 148.63, 149.20, 150.34, 181.01 (<u>C</u>O). HRMS (ESI) n/z calcd for C$_{25}$H$_{19}$N$_2$O$_3$SCl [M]$^+$: 462.0805. found [M+H]$^+$: 463.0900, [M–H]$^-$: 461.0754.

Example 50

10-Chloro-6-(phenethylamino)-12H-thiochromeno[2,3-c]quinolin-12-one (N30)

Product N30 was prepared from 3 and phenethylamine. The pure compound was obtained as a brown solid (yield 94%) (R$_f$=0.52 at CH$_2$Cl$_2$:n-hexane=2:1). Mp 151-152° C. (MeOH). $^1$H NMR (400 MHz, CDCl$_3$): δ (ppm) 3.10 (2H, t, J=6.8 Hz, —CH$_2$—), 3.98 (2H, q, J=6.4 Hz, —NCH$_2$—), 4.91 (1H, t, J=4.8 Hz, —NH—), 7.27-7.39 (5H, m, Ar'—H), 7.45 (1H, t, J=8.0 Hz, Ar—H), 7.54 (1H, d, J=8.4 Hz, Ar—H), 7.59 (1H, d, J=1.2 Hz, Ar—H), 7.63 (1H, t, J=7.6 Hz, Ar—H), 7.85 (1H, d, J=8.4 Hz, Ar—H), 8.54 (1H, d, J=1.6 Hz, Ar—H), 9.44 (1H, d, J=8.4 Hz, Ar—H). $^{13}$C NMR (100 MHz, CDCl$_3$): δ (ppm) 35.33, 43.52, 120.77, 123.66, 124.69, 125.85, 126.56, 127.23, 127.50, 128.73, 128.94, 129.33, 129.48, 129.50, 131.03, 132.54, 134.08, 139.30, 145.57, 150.36, 180.94 (<u>C</u>O). HRMS (ESI) m/z calcd for C$_{24}$H$_{17}$N$_2$OSCl [M]$^+$: 416.9226. found [M+H]$^+$: 417.0857, [M+H+2]$^+$: 419.0834.

Example 51

10-Chloro-6-((4-methoxyphenethyl)amino)-12H-thiochromeno[2,3-c]quinolin-12-one (N31)

Product N31 was prepared from 3 and 2-(4-methoxyphenyl)ethylamine. The pure compound was obtained as a yellow solid (yield 95%) (R$_f$=0.89 at CH$_2$Cl$_2$). Mp 214-215° C. (MeOH). $^1$H NMR (400 MHz, CDCl$_3$): δ (ppm) 3.03 (2H, t, J=6.8 Hz, —CH$_2$—), 3.81 (3H, s, —OCH$_3$), 3.94 (2H, q, J=6.4 Hz, —NCH$_2$—), 4.90 (1H, t, J=4.8 Hz, —NH—), 6.90 (2H, d, J=8.4 Hz, Ar'—H), 7.23 (2H, d, J=8.4 Hz, Ar'—H), 7.45 (1H, t, J=7.6 Hz, Ar—H), 7.55 (1H, d, J=8.8 Hz, Ar—H), 7.59 (1H, d, J=2.0 Hz, Ar—H), 7.63 (1H, t, J=7.6 Hz, Ar—H), 7.85 (1H, d, J=8.0 Hz, Ar—H), 8.54 (1H, d, J=2.0 Hz, Ar—H), 9.44 (1H, d, J=8.8 Hz, Ar—H). $^{13}$C NMR (100 MHz, CDCl$_3$): δ (ppm) 34.39, 43.68, 55.31, 114.13, 120.76, 123.67, 124.67, 125.85, 127.22, 127.52, 129.36, 129.49, 129.68, 129.87, 131.05, 131.24, 132.48, 134.09, 145.59, 150.41, 158.31, 180.99 (<u>C</u>O). HRMS (ESI) m/z calcd for C$_{25}$H$_{19}$N$_2$O$_2$SCl [M]$^+$: 446.0856. found [M+H]$^+$: 447.0938.

Example 52

6-((4-Aminophenethyl)amino)-10-chloro-12H-thiochromeno[2,3c]quinolin-12-one (N32)

Product N32 was prepared from 3 and 2-(4-aminophenyl)ethylamine. The pure compound was obtained as a yellow solid (yield 82%) (R$_f$=0.52 at CH$_2$Cl$_2$). Mp 208-210° C. (MeOH). $^1$H NMR (400 MHz, CDCl$_3$): δ (ppm) 2.97 (2H, t, J=6.8 Hz, —CH$_2$—), 3.63 (2H, br, —NH$_2$), 3.91 (2H, q, J=6.4 Hz, —NCH$_2$—), 4.91 (1H, t, J=4.8 Hz, —NH—), 6.70 (2H, d, J=8.4 Hz, Ar'—H), 7.09 (2H, d, J=8.0 Hz, Ar'—H), 7.44 (1H, t, J=7.6 Hz, Ar—H), 7.55 (1H, d, J=8.0 Hz, Ar—H), 7.60 (1H, d, J=8.4 Hz, Ar—H), 7.63 (1H, t, J=7.6 Hz, Ar—H), 7.84 (1H, d, J=8.0 Hz, Ar—H), 8.54 (1H, d, J=2.0 Hz, Ar—H), 9.44 (1H, d, J=8.4 Hz, Ar—H). $^{13}$C NMR (100 MHz, CDCl$_3$): δ (ppm) 34.37, 43.70, 115.52, 120.72, 123.73, 124.59, 125.83, 127.19, 127.51, 129.06, 129.31, 129.45, 129.59, 129.75, 131.09, 132.42, 134.04, 144.89, 145.60, 150.45, 180.96 (<u>C</u>O). HRMS (ESI) m/z calcd for C$_{24}$H$_{16}$N$_3$OSCl [M]$^+$: 431.0859. found [M+H]$^+$: 432.0950.

Example 53

2-(10-Chloro-12-oxo-12H-thiochromeno[2,3-c]quinolin-6-yl)guanidine (TC-SCl-A-41) (N33)

Product N33 was a yellow solid (yield 85%). Mp: 370° C. (dec.) $^1$H NMR (400 MHz, DMSO-d$_6$): δ ppm. 7.40 (3H, td, J=8.4, 1.2 Hz, Ar—H & —NH$_2$), 7.59 (1H, td, J=8.7, 1.2 Hz, Ar—H), 7.59 (1H, dd, J=8.4, 0.8 Hz, Ar—H), 7.83 (1H, dd, J=8.4, 2.0 Hz, Ar—H), 7.95 (1H, d, J=8.8 Hz, Ar—H), 8.40 (1H, d, J=2.4 Hz, Ar—H), 9.49 (1H, dd, J=8.4, 0.8 Hz, Ar—H). $^{13}$C NMR (100 MHz, DMSO-d$_6$): δ ppm. 120.77, 124.49, 125.86, 126.82, 128.11, 128.60, 129.21, 129.85, 132.13, 132.52, 132.68, 136.17, 136.80, 144.49, 159.19, 181.16. HRMS (ESI) calcd for C$_{17}$H$_{11}$N$_4$OSCl [M]$^+$354.0342. found [M+H]$^+$ 355.0438.

Example 54

10-Chloro-6-(piperidin-1-ylamino)-12H-thiochromeno[2,3-c]quinolin-12-one (TC-SCl-A-26) (N34)

Product N34 was a yellow solid (yield 60%). Mp: 180-181° C. $^1$H NMR (400 MHz, CDCl$_3$): δ ppm. 1.72-1.74 (2H, m, —CH$_2$—), 1.89 (4H, quin, J=5.2 Hz, —CH$_2$—), 3.32 (4H, J=4.8 Hz, —CH$_2$—), 7.36 (1H, tt, J=8.7, 2.1 Hz, Ar—H$_{10}$), 7.47 (1H, dd, J=8.4, 2.7 Hz, Ar—H$_8$), 7.61-7.73 (3H, m, Ar—H), 8.00 (1H, d, J=8.0 Hz, Ar—H), 8.59 (1H, d, J=2.0 Hz, Ar—H), 9.63 (1H, d, J=8.8 Hz, Ar—H). $^{13}$C NMR (100 MHz, CDCl$_3$): δ ppm. 24.28, 25.91, 52.36, 123.49, 125.77, 127.32, 127.90, 128.59, 129.06, 129.27, 130.51, 131.66, 132.18, 132.39, 133.49, 134.70, 144.98, 158.53, 181.58.

Pharmacological Activity Assay

In pharmacological tests, compounds synthesized chemically including 2-21, N-1 to N-34 (a total of 54 drugs) are subjected to the following pharmacological activity tests: (1) MTT assay; (2) Topoisomerase I and II activities assay; (3) cytotoxicity assays conducted by NCI on the 26 screened compounds in 60 cancer cell lines.

Example 55

MTT Assay for Cell Cytotoxicity

All of synthesis compounds were evaluated cell cytotoxicity by using MTT colorimetric assay on PC-3 and DU-145 cell lines. DU-145 and PC-3 are human hormone-refractory (androgen-independent) prostatic cancer cell lines from American Type Culture Collection (HTB-81™, ATCC, Rockville, Md.)[125] and Bioresource Collection and Research Center (60122, BCRC, Taiwan)[126], respectively. Two of the "classical" cell lines were cultivated in RPMI-1640 medium supplemented with 5% fetal bovine serum (v/v), 100 U/mL penicillin, and 50 mg/mL streptomycin. Approximately 2×10³ cells were seeded into each well of a 96-well plate and incubated in 5% $CO_2$ at 37° C. for 24 h. To evaluate the in vitro cytotoxicity, all the synthetic compounds were dissolved in DMSO, prepared immediately before the experiments and diluted into the complete medium before being added to each well of a 96-well plate. Each compound was then added to the culture medium for designated various concentrations (0.15, 0.5, 1.5, 5, 15 μM). After 72 h, an amount of 100 μL of MTT (1 mg/mL) was added to each well, and the samples were incubated at 37° C. for 4 h. After removing the MTT solution, 100 μL of DMSO was added to each well and incubated at 37° C. for another 20 mins. The absorbency at 560 nm was measured by using an ELISA reader.

Results are expressed as mean values of at least three independent experiments. The $IC_{50}$ values of testing compounds were described in Table 1.

TABLE 1

Effects of 10-Chloro-12H-thiochromeno[2,3-c]quinolin-12-one derivatives on cytotoxicity by MTT assay.

| No. | R substitutions | MTT assay ($IC_{50}$ ± SD)[a] | |
|-----|-----------------|----------------|----------------|
| | | DU-145 (μM) | PC-3 (μM) |
| 2 | (structure: quinoline-COOH with S-phenyl-Cl) | >15 | >15 |
| 3 | —Cl | >15 | >15 |
| 4 | —OH | >15 | 10.10 ± 1.81 |
| 5 | —OCH₃ | 10.84 ± 6.55 | 3.89 ± 0.54 |
| 6 | —N(CH₃)₂ | >15 | >15 |
| 7 | —N(piperazine)NH | 5.01 ± 1.68 | 2.84 ± 0.64 |
| 8 | —N(piperazine)N—CH₃ | 12.94 ± 0.26 | 7.18 ± 2.45 |
| 9 | —N(piperazine)N—CH₂CH₃ | >15 | 12.04 ± 3.41 |
| 10 | —N(piperazine)N—CH₂CH₂OH | >15 | >15 |
| 11 | —N(piperazine)N—CH₂-phenyl | >15 | >15 |

TABLE 1-continued
Effects of 10-Chloro-12H-thiochromeno[2,3-c]quinolin-12-one derivatives on cytotoxicity by MTT assay.
| No. | R substitutions | MTT assay (IC$_{50}$ ± SD) [a] | |
|---|---|---|---|
| | | DU-145 (μM) | PC-3 (μM) |
| 12 | 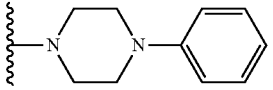 | >15 | >15 |
| 13 | 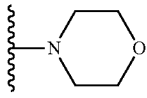 | >15 | >15 |
| 14 | 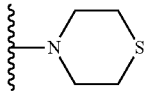 | >15 | >15 |
| 15 | 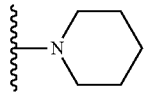 | 13.38 ± 2.87 | >15 |
| 16 | 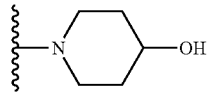 | 11.12 ± 4.18 | 9.55 ± 2.42 |
| 17 | 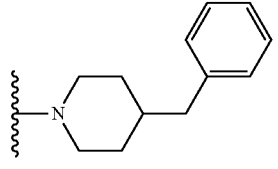 [SMILES: *N1CCN(Cc2ccccc2)CC1] | >15 | >15 |
| 18 | 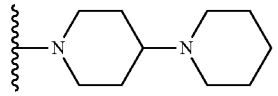 | 10.23 ± 2.03 | 14.16 ± 1.41 |
| 19 | 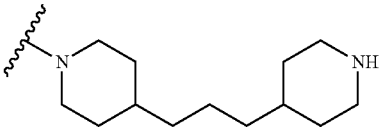 [SMILES: *N1CCC(CCCC2CCNCC2)CC1] | 9.02 ± 1.20 | 6.36 ± 0.17 |
| 20 | 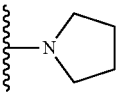 | >15 | >15 |
| 21 | 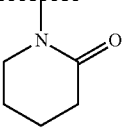 | 11.12 ± 4.18 | 9.55 ± 2.42 |
| N1 | 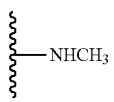 | 11.65 ± 5.15 | 14.48 ± 2.70 |
| N2 | 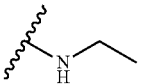 [SMILES: *NCC] | 6.70 ± 1.62 | 5.18 ± 2.20 |

TABLE 1-continued
Effects of 10-Chloro-12H-thiochromeno[2,3-c]quinolin-12-one derivatives on cytotoxicity by MTT assay.
| No. | R substitutions | MTT assay (IC$_{50}$ ± SD)[a] | |
| --- | --- | --- | --- |
| | | DU-145 (μM) | PC-3 (μM) |
| N3 | 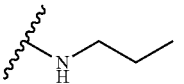 [SMILES: *NCCC] | 7.64 ± 2.74 | 7.41 ± 3.43 |
| N4 | 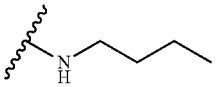 [SMILES: *NCCCC] | 10.35 ± 2.46 | 10.11 ± 1.32 |
| N5 | 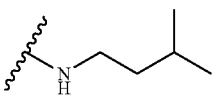 [SMILES: *NCCC(C)C] | >15 | >15 |
| N6 | 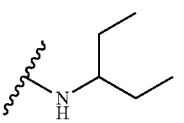 [SMILES: *NC(CC)CC] | >15 | >15 |
| N7 | 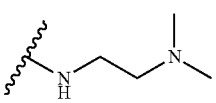 [SMILES: *NCCN(C)C] | 5.94 ± 3.45 | 2.25 ± 0.61 |
| N8 | 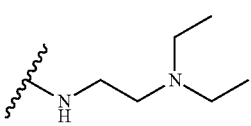 [SMILES: *NCCN(CC)CC] | 1.73 ± 0.72 | 1.11 ± 0.69 |
| N9 | 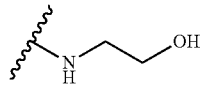 | 11.55 ± 7.23 | 7.48 ± 3.35 |
| N10 | 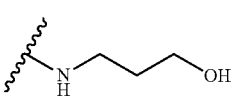 [SMILES: *NCCCO] | 5.94 ± 2.03 | 6.31 ± 4.11 |
| N11 | 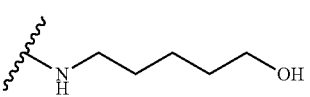 [SMILES: *NCCCCCO] | 4.95 ± 0.58 | 8.38 ± 3.39 |
| N12 | 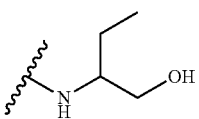 | 6.74 ± 2.14 | 7.05 ± 2.48 |
| N13 | 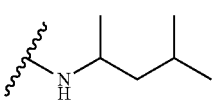 [SMILES: *NC(C)CC(C)C] | 14.16 ± 1.18 | 10.38 ± 2.30 |
| N14 | 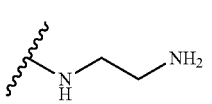 | 1.80 ± 0.40 | 1.64 ± 0.55 |
| N15 | 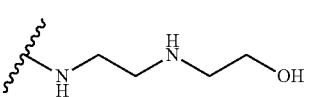 [SMILES: *NCCNCCO] | 3.81 ± 1.88 | 3.44 ± 1.81 |

TABLE 1-continued
Effects of 10-Chloro-12H-thiochromeno[2,3-c]quinolin-12-one derivatives on cytotoxicity by MTT assay.
| No. | R substitutions | MTT assay (IC$_{50}$ ± SD)[a] | |
|---|---|---|---|
| | | DU-145 (μM) | PC-3 (μM) |
| N16 | 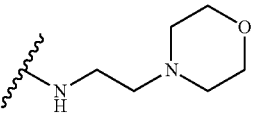 [SMILES: *NCCN1CCOCC1] | >15 | >15 |
| N17 | 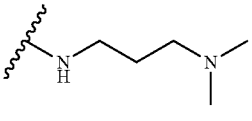 [SMILES: *NCCCN(C)C] | 2.70 ± 0.16 | 2.27 ± 0.09 |
| N18 | 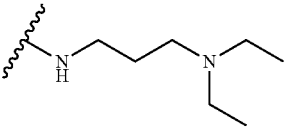 [SMILES: *NCCCN(CC)CC] | 3.53 ± 1.05 | 2.22 ± 0.21 |
| N19 | 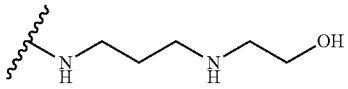 [SMILES: *NCCCNCCO] | 1.50 ± 1.32 | 1.98 ± 0.72 |
| N20 | 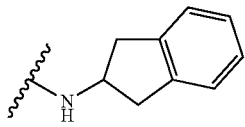 [SMILES: *NC1Cc2ccccc2C1] | 4.86 ± 0.99 | 6.20 ± 2.52 |
| N21 | 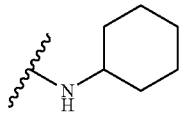 | 8.06 ± 2.08 | 7.51 ± 0.22 |
| N22 | 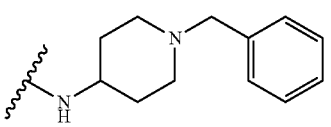 [SMILES: *NC1CCN(Cc2ccccc2)CC1] | 8.39 ± 1.84 | 6.47 ± 0.30 |
| N23 | 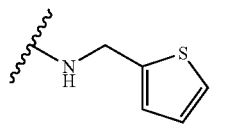 | 14.65 ± 3.84 | >15 |
| N24 | 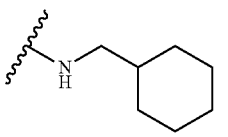 | 13.55 ± 3.88 | 14.80 ± 3.26 |
| N25 | 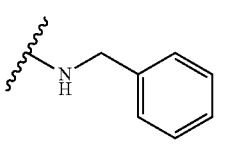 [SMILES: *NCc1ccccc1] | 13.49 ± 0.69 | 11.16 ± 1.55 |
| N26 | 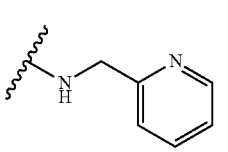 [SMILES: *NCc1ccccn1] | 14.75 ± 1.99 | 14.20 ± 2.22 |

TABLE 1-continued

Effects of 10-Chloro-12H-thiochromeno[2,3-c]quinolin-12-one derivatives on cytotoxicity by MTT assay.

| No. | R substitutions | MTT assay (IC$_{50}$ ± SD)[a] | |
|---|---|---|---|
| | | DU-145 (μM) | PC-3 (μM) |
| N27 | (3,4-methylenedioxybenzyl)amino | 11.82 ± 5.83 | >15 |
| N28 | (2-methoxybenzyl)amino | 9.61 ± 4.88 | 6.01 ± 3.31 |
| N29 | (3,4-dimethoxybenzyl)amino | 4.86 ± 0.99 | 6.20 ± 2.52 |
| N30 | (2-phenylethyl)amino | >15 | >15 |
| N31 | (2-(4-methoxyphenyl)ethyl)amino | >15 | >15 |
| N32 | (2-(4-aminophenyl)ethyl)amino | 13.59 ± 1.39 | 10.11 ± 0.94 |
| N33 | guanidino | 8.11 ± 1.37 | 6.13 ± 6.98 |
| N34 | piperidin-1-ylamino | 9.06 ± 1.95 | 8.22 ± 1.02 |
| — | Mitoxantrone | 0.10 ± 0.01 | 0.39 ± 0.02 |
| — | Doxorubicin | 0.12 ± 0.03 | 0.63 ± 0.26 |
| — | Camptothecin | 0.10 ± 0.01 | 0.10 ± 0.01 |
| — | Etoposide (VP-16) | 0.40 ± 0.01 | 4.33 ± 0.86 |

[a] SD: standard derivatives, all experiments were independently performed at least three times.

Besides, compounds N7, N8, N14, N15, N17, and N18 containing more than one nitrogen atom in the side chains showed the outstanding cytotoxic activities than having a hydroxyl group, alkyl group, or aromatic rings. Compounds 5, 7, 8, 16, 19, N2, N7, N8, N9, N14, N15, N16, N17, N18, N19, and N25 were selected for TOPs activities assay.

Example 56

Topoisomerase I and II Activities Assay

Figure 2:
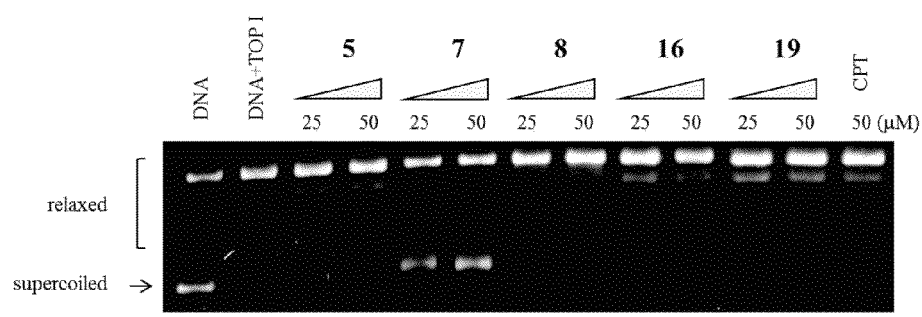
FIG. 2 is the effect of compounds 5, 7, 8, 16, 19 and CPT on DNA relaxation catalyzed by TOP I at a concentration of 25 µM and 50 µM.
Figure 3:
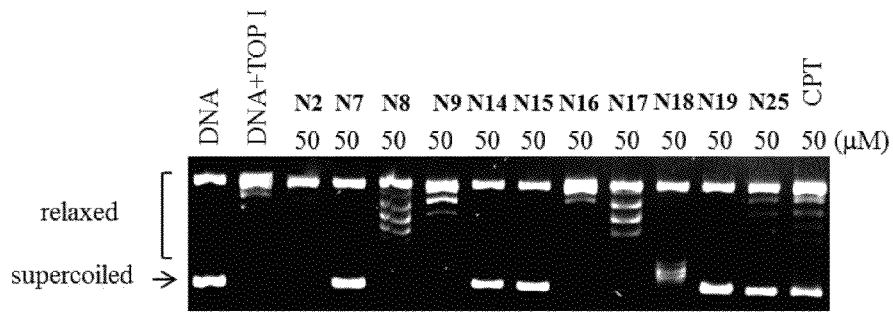
FIG. 3 is the effect of compounds N2, N7, N8, N9, N14-N19, N25, and CPT on DNA relaxation catalyzed by TOP I at a concentration of 50 µM.
Figure 4A:
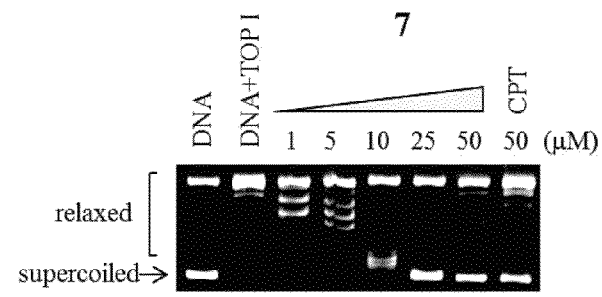
FIG. 4a-d are the effects of compounds 7, N7, N14, N15, N18, N19 and N25 on TOP I mediated supercoiled DNA relaxation.
Figure 4B:
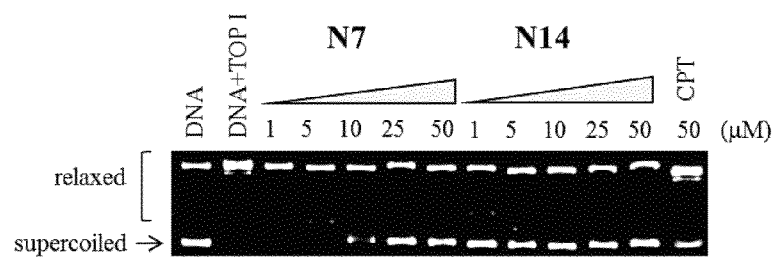
Figure 4C:
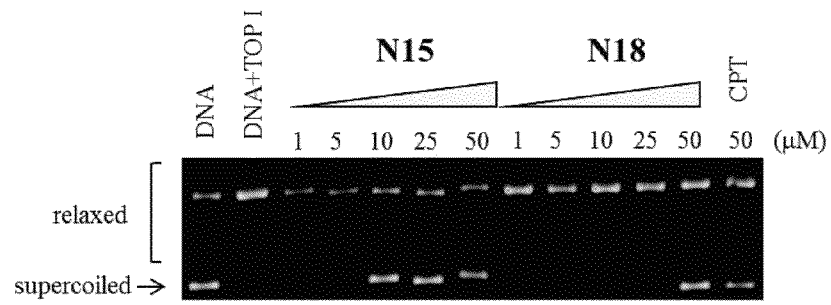
Figure 4D:
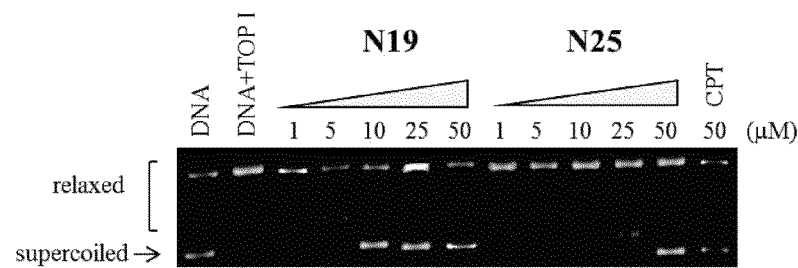

According to the cell cytotoxicity, compounds 5, 7, 8, 16, 19, N2, N7, N8, N9, N14-N19, and N25 were also selected for primary TOP I and II activities assays at 25 and/or 50 μM (FIG. 2-4). In TOP I activity assay, compounds 7, N7, N14, N15, N17, N18, and N25 were showed more potent inhibitory effects than CPT and selected for further evaluation by using five different concentrations (FIG. 4). The $IC_{50}$ value of compounds 7, N7, N14, N15, N18, N19, and N25 were about 10, 10, 1, 5, 25, 5, and 25 μM, respectively (detect by TopoGEN TG2005H, TG-2000H-1).

Figure 5:
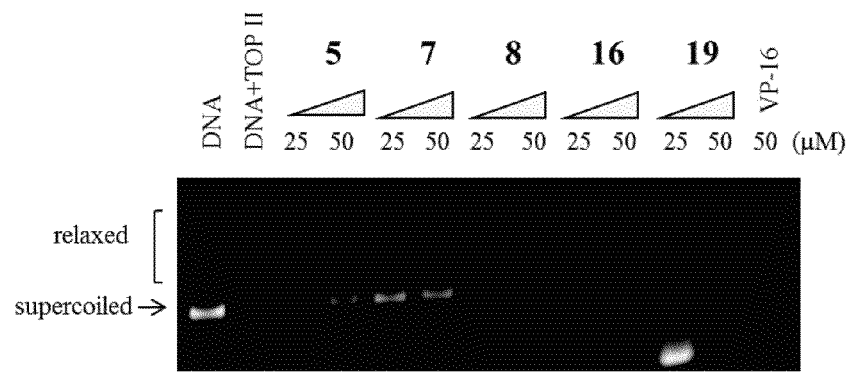
FIG. 5 is the effect of compounds 5, 7, 8, 16, 19 and VP-16 on DNA relaxation catalyzed by TOP II at a concentration of 25 µM and 50 µM.
Figure 6:
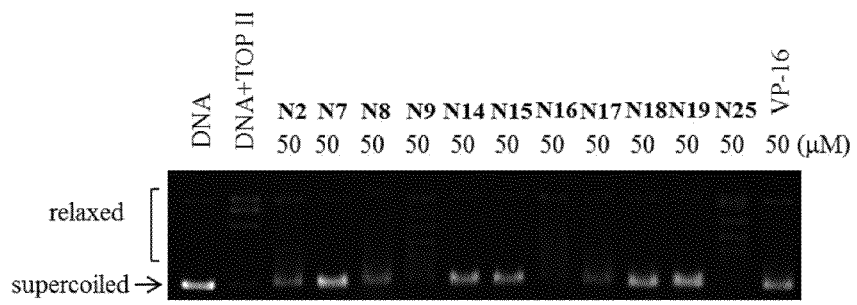
FIG. 6 is the effect of compounds N2, N7, N8, N9, N14-N19, N25, and VP-16 on DNA relaxation catalyzed by TOP II at a concentration of 50 µM.
Figure 7A:
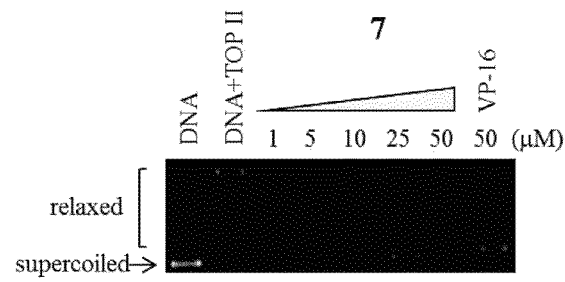
FIG. 7a-d are the effects of compounds 7, N7, N8, N14, N15, N18, and N19 on TOP II mediated supercoiled DNA relaxation.
Figure 7B:
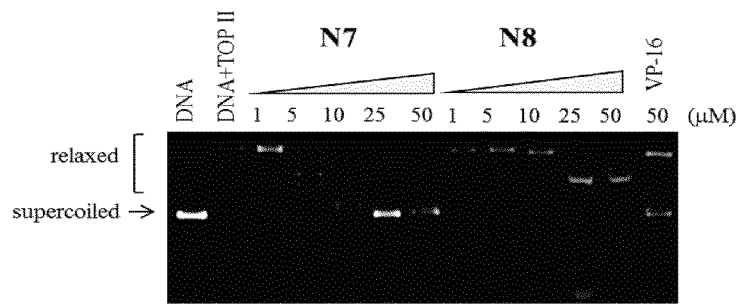
Figure 7C:
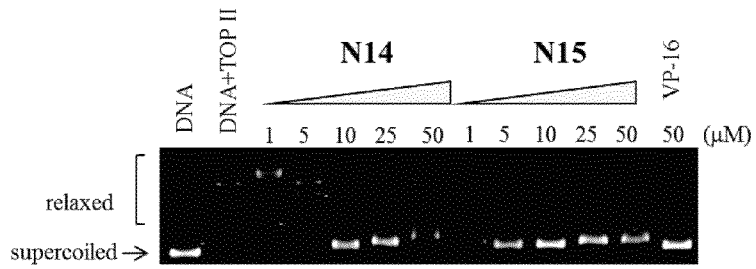
Figure 7D:
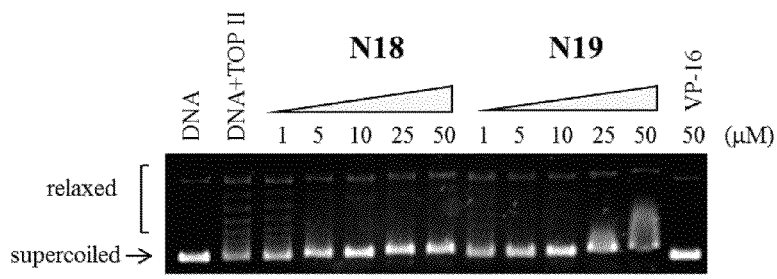

We also performed TOP II-catalyzed relaxation of plasmid DNA assays (FIG. 5-7) to evaluate if compounds could inhibit TOP II. Respond to our drug design, compounds 7, N7, N8, N14, N15, N18, and N19 were showed more potent inhibitory effects than the positive agent VP-16 and selected for further evaluation by using five different concentrations (FIG. 7). The $IC_{50}$ value of compounds 7, N7, N8, N14, N15, N18, and N19 were about 10, 10, 1, 10, 5, 1, and 1 μM, respectively (detect by TopoGEN TG2005H, TG-2000H-1).

Example 57
National Cancer Institute Cancer Cell Cytotoxicity Assay

The test results shown in this section are the compound cytotoxicities in vitro against cancer cell lines National Cancer Institute (NCI)'s anticancer drug screen and 26 compounds (2, 3, 4, 5, 6, 8, 10, 11, 12, 13, N1, N2, N6, N7, N9, N12, N13, N14, N16, N17, N19, N21, N25, N27, N30, N31) screened. In the first stage, cytotoxicity of the 26 compounds at the concentration of 10 μM was conducted on 60 cell lines and SRB assay was performed after 48 hours of incubation. The results are shown in Tables 2 to 4 and are represented by growth percentage.

Furthermore, among five compounds were active drugs for further their cytostatic and cytotoxic activities against the 60 cell panel by using five dose studies (0.01, 0.1, 1, 10 and 100 μM) (Table 5).

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

TABLE 2

In-vitro anticancer activity of compounds 2, 3, 4, 5, 6, 8, 10, 11, 12, and 13 in NCI's drug screen program.

| Panel/Cell line | Compounds/Growth percent[a] | | | | | | | | | |
|---|---|---|---|---|---|---|---|---|---|---|
| | 2 NSC-763977 | 3 NSC-771780 | 4 NSC-777199 | 5 NSC-777200 | 6 NSC-777202 | 8 NSC-771775 | 10 NSC-771776 | 11 NSC-771777 | 12 NSC-771778 | 13 NSC-771779 |
| Leukemia | | | | | | | | | | |
| CCRF-CEM | 98.31 | 93.12 | 107.78 | 106.56 | 99.42 | 91.60 | 83.46 | 95.42 | 98.41 | 88.02 |
| HL-60(TB) | 105.63 | 99.34 | 109.82 | 89.47 | 107.16 | 96.19 | 93.81 | 100.96 | 113.79 | 93.38 |
| K-562 | 112.29 | 101.04 | 107.08 | 95.83 | 99.71 | 72.98 | 35.47 | 87.84 | 112.37 | 81.18 |
| MOLT-4 | 97.25 | 98.04 | 100.41 | 80.62 | 97.52 | 87.97 | 70.01 | 90.91 | 107.23 | 89.31 |
| RPMI-8226 | 98.10 | 100.19 | 100.99 | 102.86 | 98.20 | 91.11 | 84.87 | 96.63 | 99.93 | 89.54 |
| SR | 106.33 | 89.02 | 96.00 | 88.18 | 95.68 | 86.41 | 79.07 | 85.15 | 103.11 | 88.91 |
| Non-small cell lung cancer | | | | | | | | | | |
| A549/ATCC | 107.34 | 104.74 | 95.25 | 100.46 | 94.16 | 99.80 | 95.49 | 106.37 | 98.54 | 92.97 |
| EKVX | 89.47 | N.T. | N.T. | N.T. | N.T. | N.T. | N.T. | N.T. | N.T. | N.T. |
| HOP-62 | 116.47 | 82.02 | 90.80 | 96.64 | 43.62 | 49.41 | 67.83 | 87.72 | 86.00 | 70.77 |
| HOP-92 | 72.97 | 90.83 | 93.13 | 80.11 | 58.65 | 17.97 | 39.64 | 70.17 | 81.27 | 60.43 |
| NCI-H226 | 105.64 | 83.41 | 99.58 | 98.57 | 96.20 | 85.67 | 89.29 | 88.98 | 87.10 | 88.01 |
| NCI-H23 | 92.61 | 85.12 | 88.96 | 80.14 | 77.00 | 81.11 | 84.75 | 89.94 | 93.80 | 95.21 |
| NCI-H322M | 101.10 | 100.12 | 90.87 | 90.77 | 83.74 | 77.04 | 82.85 | 88.92 | 84.41 | 88.41 |
| NCI-H460 | 104.20 | 103.14 | 96.92 | 101.23 | 88.86 | 96.05 | 93.71 | 95.57 | 103.24 | 99.28 |
| NCI-H522 | 81.64 | 96.81 | 86.60 | 92.71 | 70.42 | 98.78 | 94.76 | 96.69 | 93.50 | 89.60 |
| Colon cancer | | | | | | | | | | |
| COLO 205 | 108.65 | 112.15 | 93.69 | 97.94 | 89.67 | 90.06 | 88.90 | 105.64 | 111.67 | 99.24 |
| HCC-2998 | 100.97 | 123.28 | 101.48 | 104.67 | 97.20 | 96.87 | 103.49 | 99.32 | 105.23 | 108.75 |
| HCT-116 | 103.87 | 102.27 | 86.20 | 89.48 | 74.26 | 80.94 | 69.33 | 98.59 | 105.36 | 85.71 |
| HCT-15 | 107.80 | 102.28 | 98.11 | 107.99 | 89.27 | 93.94 | 82.92 | 94.51 | 99.81 | 93.81 |
| HT29 | 101.41 | 99.73 | 96.78 | 102.69 | 87.73 | 78.65 | 63.19 | 102.71 | 99.94 | 83.73 |
| KM12 | 112.61 | 111.27 | 102.45 | 98.03 | 96.40 | 110.71 | 101.86 | 107.75 | 113.15 | 88.68 |
| SW-620 | 96.92 | 99.06 | 101.39 | 103.05 | 105.18 | 95.50 | 88.11 | 93.08 | 100.20 | 96.18 |
| CNS cancer | | | | | | | | | | |
| SF-268 | 113.60 | 109.60 | 95.26 | 94.12 | 77.86 | 82.98 | 87.80 | 100.42 | 103.82 | 103.56 |
| SF-295 | 98.99 | 90.26 | 99.93 | 86.35 | 48.82 | 91.69 | 100.32 | 94.34 | 99.23 | 93.62 |
| SF-539 | 110.22 | 89.02 | 93.21 | 86.13 | 72.72 | 85.30 | 86.18 | 108.56 | 100.06 | 82.38 |
| SNB-19 | 97.17 | 107.89 | 101.37 | 89.36 | 76.46 | 87.07 | 84.81 | 95.52 | 105.57 | 99.37 |
| SNB-75 | 82.18 | 77.88 | 66.63 | 52.28 | 15.29 | 42.15 | 77.64 | 82.62 | 94.73 | 76.88 |
| U251 | 99.59 | 101.71 | 101.85 | 99.18 | 93.55 | 92.52 | 83.31 | 96.69 | 96.09 | 98.58 |
| Melanoma | | | | | | | | | | |
| LOX IMVI | 90.46 | 90.53 | 92.07 | 91.21 | 86.53 | 87.47 | 87.79 | 94.22 | 95.15 | 89.82 |
| MALME-3M | 107.05 | 95.87 | 93.26 | 94.19 | 89.70 | 108.36 | 119.20 | 112.36 | 121.84 | 118.84 |
| M14 | 106.90 | 106.18 | 94.76 | 88.40 | 94.36 | 102.15 | 101.70 | 93.00 | 104.02 | 110.35 |
| MDA-MB-435 | 102.02 | 100.64 | 103.18 | 103.83 | 107.18 | 105.80 | 98.24 | 96.99 | 102.39 | 102.07 |
| SK-MEL-2 | 119.91 | 95.54 | 103.04 | 105.52 | 87.26 | 97.53 | 104.06 | 107.37 | 104.26 | 98.77 |
| SK-MEL-28 | 98.95 | 101.80 | 116.59 | 112.31 | 96.60 | 107.92 | 100.66 | 104.19 | 104.22 | 111.28 |

TABLE 2-continued

In-vitro anticancer activity of compounds 2, 3, 4, 5, 6, 8,
10, 11, 12, and 13 in NCI's drug screen program.

| | Compounds/Growth percent[a] | | | | | | | | | |
|---|---|---|---|---|---|---|---|---|---|---|
| Panel/<br>Cell line | 2<br>NSC-<br>763977 | 3<br>NSC-<br>771780 | 4<br>NSC-<br>777199 | 5<br>NSC-<br>777200 | 6<br>NSC-<br>777202 | 8<br>NSC-<br>771775 | 10<br>NSC-<br>771776 | 11<br>NSC-<br>771777 | 12<br>NSC-<br>771778 | 13<br>NSC-<br>771779 |
| SK-MEL-5 | 98.07 | 97.42 | 100.69 | 99.74 | 97.92 | 99.54 | 94.13 | 98.38 | 103.57 | 95.88 |
| UACC-257 | 121.83 | 104.47 | 108.36 | 108.09 | 109.22 | 100.55 | 102.79 | 95.39 | 93.68 | 110.91 |
| UACC-62 | 102.05 | 89.69 | 105.86 | 96.15 | 87.80 | 99.27 | 91.36 | 96.00 | 104.48 | 87.86 |
| Ovarian cancer | | | | | | | | | | |
| IGROV1 | 103.57 | 96.06 | 78.35 | 71.44 | 68.16 | 80.08 | 71.67 | 93.49 | 91.38 | 80.90 |
| OVCAR-3 | 121.29 | 111.27 | 106.37 | 96.60 | 79.65 | 89.13 | 93.92 | 101.69 | 109.63 | 96.54 |
| OVCAR-4 | 98.41 | 87.91 | N.T. | N.T. | N.T. | 94.93 | 85.35 | 102.43 | 94.29 | 96.75 |
| OVCAR-5 | 112.47 | 100.07 | 111.17 | 106.70 | 98.05 | 98.14 | 95.70 | 111.92 | 108.10 | 95.97 |
| OVCAR-8 | 114.68 | 101.62 | 100.55 | 91.82 | 68.53 | 89.44 | 84.95 | 98.54 | 90.34 | 83.66 |
| NCI/ADR-RES | 97.75 | 102.80 | 96.84 | 96.10 | 87.86 | 81.35 | 92.05 | 98.31 | 100.81 | 98.16 |
| SK-OV-3 | N.T.[b] | 101.32 | 94.40 | 58.94 | 41.57 | 75.11 | 95.12 | 94.79 | 100.39 | 77.18 |
| Renal cancer | | | | | | | | | | |
| 786-0 | 104.44 | 105.25 | 99.76 | 99.15 | 87.00 | 90.48 | 85.58 | 105.57 | 101.58 | 99.31 |
| A498 | N.T. | 106.06 | 107.74 | 96.29 | 97.06 | 79.33 | 62.20 | 94.17 | 81.04 | 94.15 |
| ACHN | 113.47 | 86.84 | 95.52 | 74.89 | 64.81 | 89.73 | 83.05 | 96.39 | 94.99 | 82.54 |
| CAKI-1 | 76.26 | 94.31 | N.T. | N.T. | N.T. | 87.50 | 87.87 | 94.03 | 97.83 | 90.00 |
| RXF 393 | 113.90 | 102.55 | 116.94 | 109.68 | 83.17 | 88.57 | 70.31 | 100.71 | 107.68 | 108.61 |
| SN12C | 95.83 | 95.92 | 101.14 | 98.74 | 99.49 | 83.03 | 86.81 | 97.70 | 102.66 | 96.81 |
| TK-10 | 118.09 | 108.56 | 113.26 | 113.30 | 64.75 | 97.07 | 93.19 | 124.99 | 112.45 | 86.24 |
| UO-31 | 68.91 | 66.06 | 76.44 | 74.69 | 73.81 | 48.97 | 42.34 | 64.91 | 63.85 | 73.11 |
| Prostate cancer | | | | | | | | | | |
| PC-3 | 93.23 | 91.59 | 91.90 | 92.46 | 81.25 | 84.81 | 77.99 | 89.12 | 90.66 | 79.80 |
| DU-145 | 115.22 | 114.27 | 99.80 | 104.27 | 92.93 | 103.45 | 96.26 | 111.61 | 111.15 | 110.81 |
| Breast cancer | | | | | | | | | | |
| MCF | 91.95 | 82.58 | 69.90 | 65.39 | 22.19 | 76.60 | 51.73 | 68.32 | 74.16 | 50.59 |
| MDA-MB-231/ATCC | 95.70 | 84.28 | 81.80 | 78.12 | 71.03 | 57.30 | 55.49 | 89.11 | 94.34 | 71.53 |
| HS 578T | 88.33 | 95.14 | 113.28 | 66.51 | 60.38 | 65.57 | 76.01 | 76.42 | 85.20 | 83.27 |
| BT-549 | 124.20 | 110.01 | 85.17 | 94.85 | 92.96 | 96.25 | 90.05 | 114.05 | 123.95 | 113.81 |
| T-47D | 99.59 | 110.10 | 77.89 | 68.46 | 37.66 | 82.24 | 87.22 | 89.22 | 104.57 | 80.00 |
| MDA-MB-486 | 104.57 | 98.57 | 100.33 | 103.54 | 29.91 | 102.02 | 81.67 | 98.53 | 86.34 | 39.67 |
| Mean | 102.11 | 98.11 | 97.17 | 92.10 | 80.59 | 86.81 | 84.06 | 96.19 | 99.30 | 90.52 |
| Delta | 33.20 | 32.05 | 30.54 | 39.82 | 65.30 | 68.64 | 48.59 | 31.28 | 35.45 | 50.85 |
| Range | 55.29 | 57.22 | 50.31 | 61.02 | 93.93 | 92.74 | 83.73 | 60.08 | 60.10 | 79.17 |

[a]Data obtained from NCI in vitro 60-cell drug screen program at $10^{-5}$ molar concentration.
[b]N.T. = No test.

TABLE 3

Growth percentage of compounds N1, N2, N6, N7, N9,
N12, N13, and N14 in the NCI in vitro 60-cell Drug Screen Program.

| | Compounds/Growth percent[a] | | | | | | | |
|---|---|---|---|---|---|---|---|---|
| Panel/<br>Cell line | N1<br>NSC-<br>775512 | N2<br>NSC-<br>771784 | N6<br>NSC-<br>775513 | N7<br>NSC-<br>771785 | N9<br>NSC-<br>771786 | N12<br>NSC-<br>772854 | N13<br>NSC-<br>772855 | N14<br>NSC-<br>772865 |
| Leukemia | | | | | | | | |
| CCRF-CEM | 79.77 | 88.62 | 93.72 | −53.54 | 81.07 | 70.00 | 98.57 | −39.61 |
| HL-60(TB) | 131.66 | 103.33 | 141.93 | −47.40 | 104.58 | 96.29 | 103.96 | −47.50 |
| K-562 | 40.69 | 77.52 | 95.25 | −58.60 | 68.23 | 46.86 | 106.64 | −57.17 |
| MOLT-4 | 86.86 | 92.27 | 103.08 | −56.34 | 78.76 | 61.79 | 93.68 | −58.82 |
| RPMI-8226 | 93.10 | 79.66 | 108.60 | −37.68 | 83.81 | 73.50 | 97.78 | −27.48 |
| SR | 47.76 | 84.32 | 104.59 | −34.76 | 60.44 | 62.38 | 97.29 | −51.67 |
| Non-small cell lung cancer | | | | | | | | |
| A549/ATCC | 51.68 | 61.84 | 91.04 | 23.38 | 80.72 | 69.86 | 101.98 | −88.76 |
| EKVX | N.T.[b] | N.T. | N.T. | N.T. | N.T. | N.T. | N.T. | N.T. |
| HOP-62 | 79.39 | 57.49 | 95.32 | 56.42 | 81.90 | 55.91 | 88.69 | −97.40 |
| HOP-92 | 59.15 | −0.07 | 83.26 | −10.12 | 63.17 | N.T. | N.T. | N.T. |
| NCI-H226 | 73.53 | 41.31 | 79.22 | 58.08 | 83.55 | 77.56 | 87.55 | 28.55 |
| NCI-H23 | 44.39 | 86.29 | 94.17 | 72.59 | 86.06 | 81.25 | 95.10 | −5.25 |

TABLE 3-continued

Growth percentage of compounds N1, N2, N6, N7, N9,
N12, N13, and N14 in the NCI in vitro 60-cell Drug Screen Program.

| Panel/<br>Cell line | N1<br>NSC-<br>775512 | N2<br>NSC-<br>771784 | N6<br>NSC-<br>775513 | N7<br>NSC-<br>771785 | N9<br>NSC-<br>771786 | N12<br>NSC-<br>772854 | N13<br>NSC-<br>772855 | N14<br>NSC-<br>772865 |
|---|---|---|---|---|---|---|---|---|
| NCI-H322M | 60.89 | 74.88 | 92.45 | 49.16 | 79.00 | 58.98 | 85.51 | −50.28 |
| NCI-H460 | 73.84 | 53.33 | 99.42 | −71.14 | 100.97 | 83.78 | 95.17 | −62.39 |
| NCI-H522 | 97.00 | 80.75 | 99.02 | −8.99 | 76.94 | 64.07 | 102.30 | −66.59 |
| Colon cancer | | | | | | | | |
| COLO 205 | 94.82 | 82.36 | 107.68 | −82.85 | 99.13 | 68.37 | 93.45 | −87.22 |
| HCC-2998 | 105.34 | 98.02 | 119.79 | −83.65 | 101.55 | 99.61 | 112.26 | −90.43 |
| HCT-116 | 32.49 | 48.13 | 99.01 | −96.59 | 93.62 | 73.42 | 90.30 | −48.19 |
| HCT-15 | 68.73 | 79.72 | 95.35 | −30.05 | 78.61 | 77.58 | 96.97 | −45.92 |
| HT29 | 114.79 | 68.21 | 116.70 | −84.24 | 87.36 | 78.24 | 121.02 | −83.30 |
| KM12 | 68.75 | 85.79 | 94.04 | −77.07 | 91.93 | 82.37 | 105.66 | −85.99 |
| SW-620 | 84.37 | 84.65 | 104.94 | −67.82 | 97.18 | 84.32 | 92.80 | −66.88 |
| CNS cancer | | | | | | | | |
| SF-268 | 70.58 | 78.23 | 102.86 | 39.05 | 95.06 | 76.71 | 105.52 | −67.65 |
| SF-295 | 89.04 | 69.49 | 104.18 | −32.59 | 92.50 | 89.58 | 95.92 | −74.29 |
| SF-539 | 59.86 | 60.35 | 95.09 | 48.73 | 90.56 | 83.86 | N.T. | 2.13 |
| SNB-19 | 96.48 | 84.19 | 99.01 | 55.44 | 90.96 | 93.87 | 106.79 | 40.06 |
| SNB-75 | 67.29 | 12.12 | 73.24 | 33.36 | 90.05 | 31.01 | 85.02 | −43.13 |
| U251 | 85.19 | 76.58 | 97.05 | −39.75 | 84.10 | 74.49 | 105.12 | N.T. |
| Melanoma | | | | | | | | |
| LOX IMVI | 44.95 | 80.61 | 89.35 | −84.12 | 86.96 | 79.25 | 98.90 | N.T. |
| MALME-3M | 72.46 | 77.31 | 92.36 | −4.32 | 104.86 | 58.66 | 95.93 | −48.42 |
| M14 | 105.85 | 91.72 | 107.34 | −92.77 | 107.09 | 85.38 | 94.27 | −55.62 |
| MDA-MB-435 | 84.97 | 80.67 | 108.13 | −64.64 | 94.98 | 92.11 | 108.08 | −85.39 |
| SK-Mel-2 | 110.10 | 76.15 | 104.97 | −7.83 | 86.80 | N.T. | N.T. | N.T. |
| SK-MEL-28 | 83.41 | 93.07 | 98.40 | −76.79 | 100.76 | 82.86 | 106.87 | −96.20 |
| SK-MEL-5 | 80.13 | 73.99 | 90.08 | 18.83 | 97.36 | 87.19 | 90.71 | 68.64 |
| UACC-257 | 91.23 | 75.21 | 99.44 | −48.22 | 89.33 | 95.71 | 114.40 | −67.35 |
| UACC-62 | 77.66 | 69.06 | 83.74 | −76.58 | 76.52 | 76.17 | 96.09 | −96.67 |
| Ovarian cancer | | | | | | | | |
| IGROV1 | 67.97 | 59.26 | 80.40 | 33.20 | 88.51 | 66.54 | 74.77 | −77.31 |
| OVCAR-3 | N.T. | 76.51 | N.T. | 19.74 | 103.35 | 96.34 | 115.22 | −84.15 |
| OVCAR-4 | 71.33 | 23.19 | 98.77 | 60.67 | 102.67 | 83.23 | 86.07 | −20.15 |
| OVCAR-5 | 86.91 | 92.93 | 99.96 | 24.27 | 101.56 | 88.01 | 101.36 | −52.16 |
| OVCAR-8 | 31.61 | 62.54 | 95.31 | 1.22 | 78.13 | 68.74 | 92.79 | −74.59 |
| NCI/ADR-RES | 70.95 | 88.61 | 101.32 | 23.00 | 91.54 | 77.02 | 98.47 | −42.68 |
| SK-OV-3 | 88.67 | 28.90 | 99.71 | 70.10 | 104.57 | 58.93 | 86.70 | 12.25 |
| Renal cancer | | | | | | | | |
| 786-0 | 95.51 | 23.87 | 108.84 | 43.11 | 104.43 | 82.86 | 99.74 | −57.40 |
| A498 | 82.89 | 61.02 | 103.44 | 43.17 | 65.78 | 74.62 | 75.01 | 60.29 |
| ACHN | 84.47 | 43.77 | 84.92 | 7.55 | 82.25 | 69.12 | 91.24 | −92.31 |
| CAKI-1 | 68.09 | 72.44 | 73.26 | 34.60 | 89.29 | 59.29 | 86.38 | −75.30 |
| RXF 393 | 84.52 | 34.56 | 93.23 | −15.29 | 92.81 | 71.61 | 98.67 | −87.22 |
| SN12C | 92.52 | 84.57 | 94.28 | 48.67 | 92.52 | 81.98 | 95.14 | −93.98 |
| TK-10 | 81.21 | 47.11 | 138.89 | −89.05 | 78.14 | 77.45 | 123.23 | −28.04 |
| UO-31 | 65.34 | 32.06 | 78.57 | 21.83 | 51.97 | 51.01 | 78.64 | −92.77 |
| Prostate cancer | | | | | | | | |
| PC-3 | 61.41 | 77.80 | 84.63 | 33.32 | 71.70 | 58.35 | 86.33 | −97.71 |
| DU-145 | 80.29 | 87.67 | 109.54 | −80.85 | 102.77 | 87.04 | 113.48 | −96.35 |
| Breast cancer | | | | | | | | |
| MCF7 | 23.26 | 17.54 | 67.12 | −85.41 | 29.66 | 40.92 | 73.82 | −98.38 |
| MDA-MB-231/ATCC | 66.58 | 48.66 | 77.83 | −37.28 | 66.62 | 58.29 | 84.22 | −84.52 |
| HS 578T | 82.63 | 36.37 | 89.81 | 34.31 | 83.24 | 52.66 | 89.33 | 50.82 |
| BT-549 | 108.49 | 100.10 | 109.76 | 91.29 | 131.62 | 85.96 | 103.61 | 78.49 |
| T-47D | 42.13 | 38.28 | 73.62 | 26.06 | 74.45 | 46.94 | 73.76 | −82.45 |
| MDA-MB-486 | 8.75 | 26.29 | 95.79 | 12.81 | 39.59 | 80.85 | 96.02 | −62.13 |
| Mean | 75.06 | 65.97 | 96.94 | −11.06 | 86.33 | 73.52 | 96.33 | −51.89 |
| Delta | 66.31 | 66.04 | 29.82 | 85.53 | 56.67 | 42.51 | 22.57 | 46.49 |
| Range | 122.91 | 103.40 | 74.81 | 187.88 | 101.96 | 68.60 | 49.47 | 176.87 |

[a]Data obtained from NCI in vitro 60-cell drug screen program at $10^{-5}$ molar concentration.
[b]N.T. = No test.

TABLE 4

Growth percentage of compounds N16, N17, N19, N21, N25, N27,
N30, and N31 in the NCI in vitro 60-cell Drug Screen Program.

| Panel/ Cell line | N16 NSC777203 | N17 NSC775511 | N19 NSC777201 | N21 NSC772866 | N25 NSC772867 | N27 NSC775508 | N30 NSC775509 | N31 NSC775510 |
|---|---|---|---|---|---|---|---|---|
| Leukemia | | | | | | | | |
| CCRF-CEM | 82.21 | 69.06 | −54.78 | 92.23 | 102.34 | 88.86 | 114.29 | 100.93 |
| HL-60(TB) | 104.97 | 77.32 | −37.88 | 107.06 | 98.82 | 112.12 | 105.68 | 94.27 |
| K-562 | 17.67 | 47.53 | −66.94 | 102.86 | 90.61 | 80.37 | 82.82 | 91.76 |
| MOLT-4 | 80.91 | 70.71 | −47.57 | 92.42 | 92.42 | 87.55 | 87.33 | 82.02 |
| RPMI-8226 | 92.20 | 78.66 | 5.53 | 94.56 | 88.54 | 96.35 | 77.36 | 99.98 |
| SR | 67.74 | 48.48 | −51.40 | 85.52 | 85.46 | 79.57 | 89.88 | 94.13 |
| Non-small cell lung cancer | | | | | | | | |
| A549/ATCC | 95.12 | 81.19 | −64.45 | 85.28 | 68.33 | 104.74 | 88.44 | 93.49 |
| EKVX | N.T.[b] | N.T. | N.T. | N.T. | N.T. | N.T. | N.T. | N.T. |
| HOP-62 | 67.97 | 86.73 | 36.97 | 101.46 | 66.53 | 78.01 | 103.19 | 90.07 |
| HOP-92 | 58.79 | 40.76 | 23.01 | N.T. | N.T. | 45.39 | 73.02 | 67.57 |
| NCI-H226 | 94.09 | 81.01 | 86.75 | 93.26 | 79.35 | 53.50 | 77.00 | 72.39 |
| NCI-H23 | 83.07 | 100.25 | 54.26 | 91.11 | 74.37 | 79.93 | 89.89 | 92.72 |
| NCI-H322M | 76.96 | 82.29 | 10.05 | 91.10 | 91.00 | 73.65 | 117.72 | 99.19 |
| NCI-H460 | 100.49 | 88.06 | −80.98 | 91.29 | 64.41 | 76.71 | 95.11 | 98.14 |
| NCI-H522 | 76.66 | 98.76 | −59.68 | 83.95 | 75.71 | 78.43 | 93.93 | 93.69 |
| Colon cancer | | | | | | | | |
| COLO 205 | 79.39 | 91.35 | −87.17 | 103.96 | 80.79 | 87.63 | 100.02 | 105.41 |
| HCC-2998 | 90.51 | 108.36 | −74.47 | 109.83 | 95.77 | N.T. | 113.77 | 105.27 |
| HCT-116 | 81.64 | 70.19 | −91.19 | 65.37 | 66.87 | 69.98 | 85.77 | 98.46 |
| HCT-15 | 58.81 | 80.92 | −76.47 | 91.71 | 71.76 | 77.41 | 91.82 | 100.67 |
| HT29 | 43.13 | 90.98 | −83.53 | 105.11 | 77.16 | 82.91 | 109.15 | 120.78 |
| KM12 | 68.16 | 97.75 | −83.29 | 112.90 | 80.34 | 87.96 | 90.99 | 109.46 |
| SW-620 | 99.65 | 91.74 | −81.48 | 87.98 | 78.97 | 76.95 | 93.45 | 97.10 |
| CNS cancer | | | | | | | | |
| SF-268 | 79.49 | 87.67 | 17.28 | 92.06 | 73.68 | 93.24 | 101.32 | 100.14 |
| SF-295 | 102.17 | 95.14 | −93.00 | 92.22 | 74.33 | 94.39 | 95.46 | 95.31 |
| SF-539 | 76.72 | 87.85 | −47.59 | 91.20 | 80.59 | 77.12 | 97.86 | 95.67 |
| SNB-19 | 90.44 | 97.83 | 46.07 | 106.72 | 102.93 | 97.62 | 100.6 | 96.74 |
| SNB-75 | 60.74 | 60.99 | 23.66 | 81.91 | 14.83 | 57.14 | 68.76 | 74.50 |
| U251 | 76.34 | 84.19 | −66.76 | N.T. | N.T. | 81.03 | 96.78 | 98.72 |
| Melanoma | | | | | | | | |
| LOX IMVI | 67.43 | 66.16 | −82.79 | N.T. | N.T. | 78.69 | 89.03 | 87.78 |
| MALME-3M | 78.79 | 100.91 | −34.30 | 93.42 | 77.59 | 81.64 | 122.61 | 99.74 |
| M14 | 99.59 | 103.73 | 6.12 | 103.41 | 87.29 | 94.93 | 97.97 | 100.06 |
| MDA-MB-435 | 98.93 | 93.04 | −88.95 | 106.98 | 89.58 | 91.64 | 106.06 | 104.49 |
| SK-Mel-2 | 94.52 | 106.47 | 53.64 | N.T. | N.T. | 95.57 | 106.33 | 113.12 |
| SK-MEL-28 | 98.56 | 99.63 | −94.33 | 101.79 | 84.20 | 88.24 | 98.94 | 99.41 |
| SK-MEL-5 | 91.61 | 91.73 | 62.02 | 97.00 | 92.81 | 79.86 | 89.49 | 85.38 |
| UACC-257 | 106.52 | 107.40 | 45.70 | 103.68 | 83.24 | N.T. | 109.29 | 98.66 |
| UACC-62 | 94.58 | 102.63 | −77.63 | 93.23 | 89.20 | 72.96 | 74.67 | 80.17 |
| Ovarian cancer | | | | | | | | |
| IGROV1 | 74.11 | 87.27 | −43.25 | 83.31 | 53.42 | 67.81 | N.T. | 86.73 |
| OVCAR-3 | 97.14 | N.T. | N.T. | 91.85 | 76.59 | N.T. | N.T. | N.T. |
| OVCAR-4 | N.T. | 94.63 | 12.32 | 72.10 | 27.24 | 53.73 | 79.53 | 79.00 |
| OVCAR-5 | 68.98 | 106.26 | −65.05 | 98.06 | 91.27 | 84.38 | 102.03 | 100.83 |
| OVCAR-8 | 92.43 | 98.38 | 9.89 | 74.91 | 68.33 | 79.45 | 95.61 | 97.83 |
| NCI/ADR-RES | 77.03 | 96.94 | 26.35 | 95.91 | 77.36 | 91.11 | 96.51 | 103.78 |
| SK-OV-3 | 85.34 | 99.91 | 76.48 | 94.54 | 36.71 | 82.87 | 102.16 | 96.11 |
| Renal cancer | | | | | | | | |
| 786-0 | 83.16 | 93.30 | −17.60 | 97.69 | 72.48 | 95.83 | 108.00 | 100.71 |
| A498 | 80.54 | 78.57 | 61.88 | 93.00 | 86.46 | 75.91 | 83.22 | 99.56 |
| ACHN | 91.61 | 86.20 | −96.96 | 97.31 | 51.82 | 58.48 | 90.85 | 91.19 |
| CAKI-1 | N.T. | 84.31 | N.T. | 72.76 | 80.38 | 75.09 | 81.04 | 85.75 |
| RXF 393 | 93.21 | 76.32 | 43.67 | 97.03 | 71.08 | 74.20 | 96.74 | 88.50 |
| SN12C | 95.98 | 83.63 | 78.75 | 89.12 | 87.80 | 85.53 | 86.54 | 94.23 |
| TK-10 | 76.67 | 108.89 | −92.61 | 127.96 | 75.80 | 116.79 | 122.13 | 132.57 |
| UO-31 | 54.16 | 72.62 | 24.54 | 72.52 | 65.31 | 80.98 | 75.82 | 72.12 |
| Prostate cancer | | | | | | | | |
| PC-3 | 67.82 | 81.31 | −26.98 | 75.02 | 72.70 | 78.54 | 87.25 | 84.95 |
| DU-145 | 93.09 | 97.29 | −71.03 | 104.25 | 74.80 | 72.44 | 100.17 | 107.03 |

TABLE 4-continued

Growth percentage of compounds N16, N17, N19, N21, N25, N27, N30, and N31 in the NCI in vitro 60-cell Drug Screen Program.

| Panel/ Cell line | N16 NSC777203 | N17 NSC775511 | N19 NSC777201 | N21 NSC772866 | N25 NSC772867 | N27 NSC775508 | N30 NSC775509 | N31 NSC775510 |
|---|---|---|---|---|---|---|---|---|
| Breast cancer | | | | | | | | |
| MCF7 | 51.69 | 51.20 | −72.49 | 46.14 | 16.01 | 43.53 | 60.91 | 59.13 |
| MDA-MB-231/ATCC | 59.20 | 73.39 | −66.53 | 77.17 | 32.67 | 54.65 | 79.55 | 82.31 |
| HS 578T | 89.65 | 87.67 | 64.69 | 94.22 | 34.73 | 70.49 | 87.62 | 87.49 |
| BT-549 | 91.21 | 99.81 | 98.48 | 105.53 | 97.19 | 111.06 | 106.85 | 105.24 |
| T-47D | 47.63 | 79.82 | 16.26 | 72.43 | 38.08 | 74.41 | 71.96 | 69.90 |
| MDA-MB-486 | 74.34 | 43.26 | −24.00 | 108.92 | −9.83 | 60.47 | 63.11 | 53.93 |
| Mean | 80.38 | 85.32 | −21.33 | 92.62 | 71.97 | 81.18 | 93.22 | 93.38 |
| Delta | 62.71 | 44.56 | 75.63 | 46.48 | 81.80 | 36.65 | 32.31 | 39.45 |
| Range | 88.85 | 68.13 | 195.44 | 81.82 | 112.76 | 73.26 | 61.70 | 78.64 |

[a] Data obtained from NCI in vitro 60-cell drug screen program at $10^{-5}$ molar concentration.
[b] N.T. = No test.

TABLE 5

In vitro antitumor activity ($GI_{50}$ in μM), toxicity ($LC_{50}$ in μM) and TGI data of selected compounds N2, N7, N14, N19, and N25.

| Panel/ Cell line | N2 (NSC771784) | | | N7 (NSC771785) | | | N14 (NSC772865) | | | N19 (NSC777201) | | | N25 (NSC772867) | | |
|---|---|---|---|---|---|---|---|---|---|---|---|---|---|---|---|
| (μM) | $GI_{50}$ | TGI | $LC_{50}$ | $GI_{50}$ | TGI | $LC_{50}$ | $GI_{50}$ | TGI | $LC_{50}$ | $GI_{50}$ | TGI | $LC_{50}$ | $GI_{50}$ | TGI | $LC_{50}$ |
| Leukemia | | | | | | | | | | | | | | | |
| CCRF-CEM | >100 | >100 | >100 | 1.63 | 3.41 | 7.15 | 1.75 | 3.65 | 7.64 | 1.83 | 3.80 | — | >100 | >100 | >100 |
| HL-60 (TB) | >100 | >100 | >100 | 1.76 | 3.49 | 6.95 | N.T. | N.T. | N.T. | N.T. | N.T. | N.T. | N.T. | N.T. | N.T. |
| K-562 | >100 | >100 | >100 | 1.33 | 3.00 | 6.74 | 1.69 | 3.65 | 7.84 | 1.73 | — | >100 | >100 | >100 | >100 |
| MOLT-4 | >100 | >100 | >100 | 1.71 | 3.40 | 6.74 | 2.02 | 3.96 | 7.77 | 1.88 | — | — | >100 | >100 | >100 |
| RPMI-8226 | >100 | >100 | >100 | 1.76 | 3.68 | 7.69 | 2.26 | 4.92 | 62.30 | 1.84 | 4.21 | — | >100 | >100 | >100 |
| SR | >100 | >100 | >100 | 1.70 | 3.73 | 8.14 | 1.81 | 4.30 | >100 | 1.98 | 4.55 | >100 | >100 | >100 | >100 |
| Non-small cell lung cancer | | | | | | | | | | | | | | | |
| A549/ATCC | 48.1 | >100 | >100 | 1.66 | 3.17 | 6.06 | 1.83 | 3.50 | 6.68 | 1.76 | 3.30 | — | 14.40 | >100 | >100 |
| EKVX | N.T. | N.T. | N.T. | N.T. | N.T. | N.T. | N.T. | N.T. | N.T. | N.T. | N.T. | N.T. | N.T. | N.T. | N.T. |
| HOP-62 | 13.30 | 35.20 | 93.10 | 1.54 | 2.92 | 5.56 | 1.47 | 2.92 | — | 1.38 | 2.89 | — | 2.43 | 5.92 | 27.70 |
| HOP-92 | N.T. | N.T. | N.T. | N.T. | N.T. | N.T. | 1.03 | 3.05 | 9.04 | 1.23 | 4.58 | 26.70 | 1.75 | 7.53 | 53.60 |
| NCI-H226 | 33.20 | >100 | >100 | 1.84 | 4.38 | 24.30 | 1.36 | 2.95 | — | 1.90 | 4.46 | >100 | 1.84 | — | >100 |
| NCI-H23 | N.T. | N.T. | N.T. | N.T. | N.T. | N.T. | 1.72 | 3.37 | 6.63 | 1.89 | 3.68 | — | 15.20 | >100 | >100 |
| NCI-H322M | 69.50 | >100 | >100 | 1.74 | 3.18 | 5.81 | 1.65 | 3.34 | 6.74 | 1.80 | 3.56 | 7.03 | >100 | >100 | >100 |
| NCI-H460 | >100 | >100 | >100 | 1.76 | 3.38 | 6.50 | 1.69 | 3.45 | 7.05 | 1.66 | 3.35 | — | 5.00 | >100 | >100 |
| NCI-H522 | 24.80 | >100 | >100 | 1.59 | 3.07 | 5.90 | 1.86 | 3.59 | 6.92 | 1.85 | 3.56 | — | 25.30 | >100 | >100 |
| Colon cancer | | | | | | | | | | | | | | | |
| COLO 205 | >100 | >100 | >100 | 1.66 | 3.17 | 6.05 | 1.73 | 3.57 | — | 1.63 | 3.37 | — | — | >100 | >100 |
| HCC-2998 | >100 | >100 | >100 | 1.68 | 3.38 | 6.82 | 2.03 | 4.06 | 8.14 | 1.58 | 3.42 | — | >100 | >100 | >100 |
| HCT-116 | 6.31 | >100 | >100 | 1.57 | 3.18 | 6.45 | 1.63 | 2.99 | 5.47 | 1.60 | 3.05 | — | 5.59 | >100 | >100 |
| HCT-15 | >100 | >100 | >100 | 1.59 | 3.14 | 6.21 | 1.58 | 3.12 | 6.16 | 1.61 | 3.25 | 6.57 | 8.75 | >100 | >100 |
| HT29 | >100 | >100 | >100 | 1.65 | 3.36 | 6.88 | 1.78 | 3.29 | 6.09 | 2.05 | 4.00 | 7.82 | — | >100 | >100 |
| KM12 | >100 | >100 | >100 | 1.78 | 3.28 | 6.03 | 1.67 | 3.11 | 5.79 | 1.67 | 3.31 | — | 48.30 | >100 | >100 |
| SW-620 | >100 | >100 | >100 | 1.71 | 3.29 | 6.36 | 1.67 | 3.42 | 7.02 | 1.63 | 3.30 | — | — | >100 | >100 |
| CNS cancer | | | | | | | | | | | | | | | |
| SF-268 | 22.10 | >100 | >100 | 1.57 | 3.16 | 6.35 | 1.59 | 3.23 | 6.55 | 1.67 | 3.35 | — | 13.80 | >100 | >100 |
| SF-295 | 12.20 | 35.20 | >100 | 1.73 | 3.21 | 5.98 | 1.79 | 3.63 | — | 1.73 | 3.33 | — | 3.50 | 16.50 | >100 |
| SF-539 | 10.10 | 58.50 | >100 | 1.68 | 3.08 | 5.67 | 1.57 | 2.95 | 5.52 | 1.70 | 3.22 | 6.11 | 4.49 | 46.40 | >100 |
| SNB-19 | 26.60 | 81.10 | >100 | 1.54 | 3.07 | 6.10 | 1.65 | 3.18 | — | 1.64 | 3.26 | — | 8.56 | >100 | >100 |
| SNB-75 | 4.96 | 22.00 | 60.20 | 1.28 | 3.69 | 12.10 | 1.09 | 2.31 | 4.90 | 1.28 | 2.56 | 5.14 | 1.45 | 3.78 | 9.91 |
| U251 | 16.90 | 67.90 | >100 | 1.48 | 2.84 | 5.44 | 1.63 | 3.07 | 5.78 | 1.73 | 3.22 | — | 4.41 | 25.10 | >100 |
| Melanoma | | | | | | | | | | | | | | | |
| LOX IMVI | >100 | >100 | >100 | 1.68 | 3.24 | 6.24 | 1.68 | 3.16 | 5.96 | 1.80 | 3.80 | — | >100 | >100 | >100 |

TABLE 5-continued

In vitro antitumor activity (GI$_{50}$ in μM), toxicity (LC$_{50}$ in μM) and TGI data of selected compounds N2, N7, N14, N19, and N25.

| Panel/ Cell line (μM) | N2 (NSC771784) | | | N7 (NSC771785) | | | N14 (NSC772865) | | | N19 (NSC777201) | | | N25 (NSC772867) | | |
|---|---|---|---|---|---|---|---|---|---|---|---|---|---|---|---|
| | GI$_{50}$ | TGI | LC$_{50}$ | GI$_{50}$ | TGI | LC$_{50}$ | GI$_{50}$ | TGI | LC$_{50}$ | GI$_{50}$ | TGI | LC$_{50}$ | GI$_{50}$ | TGI | LC$_{50}$ |
| MALME-3M | N.T. | N.T. | N.T. | N.T. | N.T. | N.T. | 1.98 | 3.96 | 7.93 | 2.15 | 4.33 | — | >100 | >100 | >100 |
| M14 | >100 | >100 | >100 | 1.85 | 3.44 | 6.40 | 1.83 | 3.35 | 6.14 | 1.83 | 3.53 | 6.82 | >100 | >100 | >100 |
| MDA-MB-435 | >100 | >100 | >100 | 1.71 | 3.22 | 6.05 | 1.82 | 3.59 | — | 1.59 | 2.99 | 5.62 | >100 | >100 | >100 |
| SK-Mel-2 | 16.3 | 43.2 | >100 | 1.80 | 3.32 | 6.12 | 1.98 | 3.95 | 7.87 | 2.05 | 3.77 | 6.90 | 10.60 | 31.90 | 96.50 |
| SK-MEL-28 | >100 | >100 | >100 | 1.81 | 3.27 | 5.89 | 1.75 | 3.15 | 5.66 | 1.89 | 3.56 | — | — | >100 | >100 |
| SK-MEL-5 | — | >100 | >100 | 1.57 | 3.59 | 8.21 | 1.51 | 2.87 | 5.44 | 1.60 | 3.00 | 5.63 | 4.23 | >100 | >100 |
| UACC-257 | >100 | >100 | >100 | 1.74 | 3.21 | 5.93 | 1.90 | 3.56 | 6.70 | 1.86 | 3.44 | 6.33 | >100 | >100 | >100 |
| UACC-62 | 22.3 | >100 | >100 | 1.70 | 3.16 | 5.88 | 1.67 | 3.30 | 6.52 | 1.81 | 3.40 | 6.39 | 16.90 | >100 | >100 |
| Ovarian cancer | | | | | | | | | | | | | | | |
| IGROV1 | 11.90 | 54.40 | >100 | 1.70 | 3.34 | 6.58 | 1.61 | 3.45 | — | 1.66 | 3.60 | — | 4.64 | >100 | >100 |
| OVCAR-3 | 52.40 | >100 | >100 | 1.61 | 3.00 | 5.58 | N.T. | N.T. | N.T. | 1.79 | 3.51 | — | N.T. | N.T. | N.T. |
| OVCAR-4 | >100 | >100 | >100 | 1.19 | 2.75 | 6.35 | 1.52 | 3.15 | 6.54 | 1.60 | 3.23 | — | 15.00 | 3.74 | — |
| OVCAR-5 | >100 | >100 | >100 | 1.45 | 2.91 | 5.83 | 1.46 | 2.88 | 5.66 | 1.63 | 3.50 | 7.53 | >100 | >100 | >100 |
| OVCAR-8 | 17.70 | >100 | >100 | 1.64 | 3.15 | 6.06 | 1.89 | 4.12 | — | 1.75 | 3.32 | — | 7.75 | >100 | >100 |
| NCI/ADR-RES | 33.50 | >100 | >100 | 1.67 | 3.17 | 6.00 | 1.88 | 3.67 | — | 1.82 | 3.63 | — | 43.00 | >100 | >100 |
| SK-OV-3 | 11.10 | 35.20 | >100 | 1.68 | 3.06 | 5.58 | 1.78 | 3.38 | 6.42 | 1.68 | 3.38 | 6.80 | 3.56 | 13.90 | >100 |
| Renal cancer | | | | | | | | | | | | | | | |
| 786-0 | 10.5 | 33.8 | >100 | 1.84 | 3.45 | 6.46 | 1.76 | 3.20 | 5.81 | 1.72 | 3.37 | — | 9.55 | 48.70 | >100 |
| A498 | 15.3 | 91.3 | >100 | 2.70 | 9.44 | 3.52 | 1.45 | 4.99 | 29.20 | 1.27 | 3.62 | 15.00 | 8.05 | 39.20 | >100 |
| ACHN | 8.66 | >100 | >100 | 1.63 | 3.07 | 5.77 | 1.44 | 2.76 | 5.29 | 1.67 | 3.22 | — | 4.02 | >100 | >100 |
| CAKI-1 | 26.4 | >100 | >100 | 1.43 | 2.80 | 5.49 | 1.56 | 3.27 | — | 1.33 | 2.69 | 5.45 | 6.07 | >100 | >100 |
| RXF 393 | 13.1 | 44.6 | >100 | 1.60 | 3.41 | 7.29 | N.T. | N.T. | N.T. | 1.64 | 3.20 | — | N.T. | N.T. | N.T. |
| SN12C | 75.3 | >100 | >100 | 1.59 | 3.12 | 6.12 | 1.45 | 3.02 | — | 1.70 | 3.39 | 6.80 | 24.90 | >100 | >100 |
| TK-10 | N.T. | N.T. | >100 | N.T. | N.T. | N.T. | 2.06 | 3.58 | 6.21 | 2.09 | 3.74 | 6.69 | 5.02 | 22.30 | >100 |
| UO-31 | 29.4 | >100 | >100 | 1.19 | 2.50 | 5.22 | 1.29 | 2.78 | 5.96 | 1.36 | 2.94 | 6.35 | 57.80 | >100 | >100 |
| Prostate cancer | | | | | | | | | | | | | | | |
| PC-3 | >100 | >100 | >100 | 1.47 | 2.90 | 5.74 | 1.55 | 2.99 | 5.76 | 1.51 | 2.92 | 5.66 | 56.90 | >100 | >100 |
| DU-145 | >100 | >100 | >100 | 1.87 | 3.34 | 5.99 | 1.81 | 3.20 | 5.66 | 1.76 | 3.31 | 6.25 | 5.50 | >100 | >100 |
| Breast cancer | | | | | | | | | | | | | | | |
| MCF7 | 0.47 | >100 | >100 | 1.23 | 2.66 | 5.71 | 1.28 | 2.81 | — | 1.05 | 2.60 | — | 0.04 | 18.60 | >100 |
| MDA-MB-231/ATCC | 10.10 | 65.5 | >100 | 1.20 | 2.51 | 5.28 | 1.31 | 2.65 | 5.35 | 1.36 | 2.86 | 6.02 | 2.36 | 34.80 | >100 |
| HS 578T | 9.64 | 65.5 | >100 | 1.74 | 4.02 | 9.27 | 1.69 | 3.90 | — | 1.29 | 3.53 | 9.64 | 2.94 | 21.20 | >100 |
| BT-549 | 9.87 | >100 | >100 | 8.91 | 2.27 | 5.33 | 2.15 | 5.35 | 62.00 | 1.67 | 3.15 | — | 20.50 | >100 | >100 |
| T-47D | N.T. | N.T. | N.T. | N.T. | N.T. | N.T. | 1.56 | 3.37 | — | 1.50 | 3.43 | — | 1.26 | 7.11 | >100 |
| MDA-MB-486 | 0.040 | >100 | >100 | 1.47 | 3.28 | 7.34 | 1.27 | 2.80 | 6.15 | 1.06 | 2.56 | 6.20 | 0.03 | 0.66 | 63.10 |
| Mean | 28.84 | 83.18 | 100 | 1.66 | 3.39 | 6.92 | 1.66 | 3.39 | 7.94 | 1.66 | 3.39 | 9.55 | 11.22 | 53.70 | 91.20 |

What is claimed is:

1. A compound as shown in formulation (I):

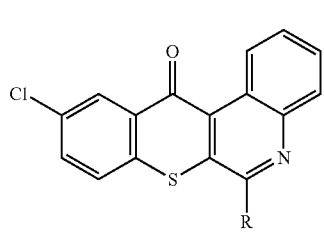

(I)

wherein the R is selected from the groups consisting of:
i) halo, amino, hydroxyl and thiol groups;
ii) linear alkyl chains of N(CH$_2$)$_n$H, alkyl groups with substituted side chains, alkyl side chains with a substituted amino group and alkyl side chains with a substituted hydroxyl group, wherein 1≤n≤10;
iii) O(CH$_2$)$_n$H, N(CH$_3$)$_2$, NH(CH$_2$)$_n$NH(CH$_2$)$_n$OH, wherein 1≤n≤10;
iv) nitrogen-containing cycloalkyl groups and heterocyclic compounds of C$_{3-12}$ which contain 1 to 3 heteroatoms selected from O, S and N, wherein the ortho-, para- and meta-position can be further selected independently from one of the groups consisting of: hydrogen group, (CH$_2$)$_n$ alkyl groups, (CH$_2$)$_n$ hydroxyl groups, (CH$_2$)$_n$ C$_{3-12}$ cycloalkyl groups, (CH$_2$)$_n$C$_{3-12}$ nitrogen-containing cycloalkyl groups, (CH$_2$)$_n$ benzene rings, formyl group and (CH$_2$)$_n$COC$_{3-12}$ nitrogen-containing cycloalkyl groups, wherein 0≤n≤10;
v) NH(CH$_2$)$_n$R$_1$, 0≤n≤10, wherein R$_1$ is selected from the groups consisting of: N(CH$_3$)$_2$, C(NH$_2$)$_2$, linear alkyl chains of NH(CH$_2$)$_n$H, alkyl groups with substituted side chains, alkyl side chains with a substituted amino group and alkyl side chains with a substituted hydroxyl group;

vi) NH(CH$_2$)$_n$R$_2$, 0≤n≤10, wherein R$_2$ is selected from the groups consisting of: benzene rings, C$_{3-12}$ cycloalkyl groups and heterocyclic groups of which contain 1 to 3 heteroatoms selected from O, S and N, wherein the ortho-, para- and meta-position can be further selected independently from one of the groups consisting of: Methoxyl group, amino group, benzene rings, alkyl, amino, nitro, hydroxyl groups with substituted C1-C3 side chains and C$_{3-12}$ heterocyclic groups; wherein the C$_{3-12}$ heterocyclic groups which contain 1 to 3 heteroatoms selected from O, S and N;

and their pharmaceutically acceptable salts, stereoisomers and enantimoers.

2. The compound according to claim 1, where the R group consisting of i)~iv) are selected from the group consisting of chlorine, hydroxyl, methoxyl, dimethylamino, piperazin-1-yl, 4-methylpiperazin-1-yl, 4-ethylpiperazin-1-yl, 4-(2-hydroxyethyl)piperazin-1-yl, 4-Benzylpiperazin-1-yl, 4-phenylpiperazin-1-yl, morpholino, thiomorpholino, piperidin-1-yl, 4-hydroxypiperidin-1-yl, 4-Benzylpiperidin-1-yl, (1,4'-Bipiperidin)-1'-yl, 4-(3-(piperidin-4-yl)propyl)piperidin-1-yl, pyrrolidin-1-yl, 2-oxopiperidin-1-yl, methylamino, ethylamino, propylamino, butylamino, isobutylamino, pentan-3-ylamino, (2-(dimethylamino)ethyl)amino, (2-(diethylamino)ethyl)amino, 2-ethanolamino, 3-propanolamino, 5-pentanolamino, (1-hydroxybutan-2-yl)amino, (4-methylpentan-2-yl)amino, (2-Aminoethyl)amino, (2-((2-hydroxyethyl)amino)ethyl)amino, (2-morpholinoethyl)amino, (3-(dimethylamino)propyl)amino, (3-(diethylamino)propyl)amino, (3-((2-hydroxyethyl)amino)propyl)amino, (2,3-dihydro-1H-inden-2-yl)amino, cyclohexylamino, (1-Benzylpiperidin-4-yl)amino, (thiophen-2-ylmethyl)amino, (cyclohexylmethyl)amino, benzylamino, (pyridin-2-ylmethyl)amino, (Benzo[d][1,3]dioxol-5-ylmethyl)amino, (2-methoxybenzyl)amino, (3,4-dimethoxybenzyl)amino, phenethylamino, (4-methoxyphenethyl)amino, (4-aminophenethyl)amino, guanidine and piperidin-1-ylamino.

3. The compound according to claim 1, wherein the compound is selected from the group consisting of:

3-((4-Chlorophenyl)thio)-2-hydroxyquinoline-4-carboxylic acid,
6,9-Dichloro-12H-thiochromeno[2,3-c]quinolin-12-one,
10-Chloro-6-hydroxy-12H-thiochromeno[2,3-c]quinolin-12-one,
10-Chloro-6-methoxy-12H-thiochromeno[2,3-c]quinolin-12-one
10-Chloro-6-dimethylamino-12H-thiochromeno[2,3-c]quinolin-12-one,
10-Chloro-6-(piperazin-1-yl)-12H-thiochromeno[2,3-c]quinolin-12-one,
10-Chloro-6-(4-methylpiperazin-1-yl)-12H-thiochromeno[2,3-c]quinolin-12-one,
10-Chloro-6-(4-ethylpiperazin-1-yl)-12H-thiochromeno[2,3-c]quinolin-12-one,
10-Chloro-6-(4-(2-hydroxyethyl)piperazin-1-yl)-12H-thiochromeno[2,3-c]quinolin-12one,
6-(4-Benzylpiperazin-1-yl)-10-chloro-12H-thiochromeno[2,3-c]quinolin-12-one,
10-Chloro-6-(4-phenylpiperazin-1-yl)-12H-thiochromeno[2,3-c]quinolin-12-one,
10-Chloro-6-morpholino-12H-thiochromeno[2,3-c]quinolin-12-one,
10-Chloro-6-thiomorpholino-12H-thiochromeno[2,3-c]quinolin-12-one,
10-Chloro-6-(piperidin-1-yl)-12H-thiochromeno[2,3-c]quinolin-12-one,
10-Chloro-6-(4-hydroxypiperidin-1-yl)-12H-thiochromeno[2,3-c]quinolin-12-one,
6-(4-Benzylpiperidin-1-yl)-10-chloro-12H-thiochromeno[2,3-c]quinolin-12-one,
6-([1,4'-Bipiperidin]-1'-yl)-10-chloro-12H-thiochromeno[2,3-c]quinolin-12-one,
10-Chloro-6-(4-(3-(piperidin-4-yl)propyl)piperidin-1-yl)-12H-thiochromeno[2,3-c]quinolin-12-one,
10-Chloro-6-(pyrrolidin-1-yl)-12H-thiochromeno[2,3-c]quinolin-12-one,
10-Chloro-6-(2-oxopiperidin-1-yl)-12H-thiochromeno[2,3-c]quinolin-12-one,
10-Chloro-6-methylamino-12H-thiochromeno[2,3-c]quinolin-12-one,
10-Chloro-6-ethylamino-12H-thiochromeno[2,3-c]quinolin-12-one,
10-Chloro-6-propylamino-12H-thiochromeno[2,3-c]quinolin-12-one,
6-(Butylamino)-10-chloro-12H-thiochromeno[2,3-c]quinolin-12-one,
10-Chloro-6-isobutylamino-12H-thiochromeno[2,3-c]quinolin-12-one,
10-Chloro-6-(pentan-3-ylamino)-12H-thiochromeno[2,3-c]quinolin-12-one,
10-Chloro-6-((2-(dimethylamino)ethyl)amino)-12H-thiochromeno[2,3-c]quinolin-12-one,
10-Chloro-6-((2-(diethylamino)ethyl)amino)-12H-thiochromeno[2,3-c]quinolin-12-one,
10-Chloro-6-(2-ethanolamino)-12H-thiochromeno[2,3-c]quinolin-12-one,
10-Chloro-6-(3-propanolamino)-12H-thiochromeno[2,3-c]quinolin-12-one,
10-Chloro-6-(5-pentanolamino)-12H-thiochromeno[2,3-c]quinolin-12-one,
10-Chloro-6-((1-hydroxybutan-2-yl)amino)-12H-thiochromeno[2,3-c]quinolin-12-one,
10-Chloro-6-((4-methylpentan-2-yl)amino)-12H-thiochromeno[2,3-c]quinolin-12-one,
6-((2-Aminoethyl)amino)-10-chloro-12H-thiochromeno[2,3-c]quinolin-12-one,
10-Chloro-6-((2-((2-hydroxyethyl)amino)ethyl)amino)-12H-thiochromeno[2,3-c]quinolin-12-one,
10-Chloro-6-((2-morpholinoethyl)amino)-12H-thiochromeno[2,3-c]quinolin-12-one,
10-Chloro-6-((3-(dimethylamino)propyl)amino)-12H-thiochromeno[2,3-c]quinolin-12-one,
10-Chloro-6-((3-(diethylamino)propyl)amino)-12H-thiochromeno[2,3-c]quinolin-12-one,
10-Chloro-6-((3-((2-hydroxyethyl)amino)propyl)amino)-12H-thiochromeno[2,3-c]quinolin-12-one,
10-Chloro-6-((2,3-dihydro-1H-inden-2-yl)amino)-12H-thiochromeno[2,3-c]quinolin-12-one,
10-Chloro-6-(cyclohexylamino)-12H-thiochromeno[2,3-c]quinolin-12-one,
6-((1-Benzylpiperidin-4-yl)amino)-10-chloro-12H-thiochromeno[2,3-c]quinolin-12-one,
10-Chloro-6-((thiophen-2-ylmethyl)amino)-12H-thiochromeno[2,3-c]quinolin-12-one,
10-Chloro-6-((cyclohexylmethyl)amino)-12H-thiochromeno[2,3-c]quinolin-12-one,
6-(Benzylamino)-10-chloro-12H-thiochromeno[2,3-c]quinolin-12-one,
10-Chloro-6-((pyridin-2-ylmethyl)amino)-12H-thiochromeno[2,3-c]quinolin-12-one, 6-((Benzo[d][1,3]dioxol-5-ylmethyl)amino)-10-chloro-12H-thiochromeno[2,3-c]quinolin-12-one,
10-Chloro-6-((2-methoxybenzyl)amino)-12H-thiochromeno[2,3-c]quinolin-12-one,
10-Chloro-6-((3,4-dimethoxybenzyl)amino)-12H-thiochromeno[2,3-c]quinolin-12-one,
10-Chloro-6-(phenethylamino)-12H-thiochromeno[2,3-c]quinolin-12-one,
10-Chloro-6-((4-methoxyphenethyl)amino)-12H-thiochromeno[2,3-c]quinolin-12-one,
6-((4-Aminophenethyl)amino)-10-chloro-12H-thiochromeno[2,3-c]quinolin-12-one,
2-(10-Chloro-12-oxo-12H-thiochromeno[2,3-c]quinolin-6-yl)guanidine,
10-Chloro-6-(piperidin-1-ylamino)-12H-thiochromeno[2,3-c]quinolin-12-one,
and their salts.

4. A pharmaceutical composition comprising the effective dosage compound according to claim 1 and at least one pharmaceutically acceptable vehicle, diluent or excipient.

5. A method for inhibiting Topoisomerase I activity which comprises administrating a effective amount of the compound according to claim 1.

6. A method for inhibiting Topoisomerase II activity which comprises administrating an effective amount of the compound according to claim 1.

7. A method for the treatment of cancer which comprises administrating an effective amount of the compound according to claim 1.

8. The method according to claim 7, wherein the cancer is selected from the groups consisting of leukemia, non-small cell lung cancer, colorectal cancer, central nervous system (CNS) cancer, melanoma, ovarian cancer, renal cancer, prostate cancer and breast cancer.

9. A method for preparation of thiochromeno[2,3-c]quinolin-12-one derivatives, wherein the method comprising:
(1) mix isatin, 2-((4-chlorophenyl)thio)acetic acid and sodium acetate was heated at 150° C. for 1 h, after cooling the mixture was added acetic acid, the precipitate was collected, washed with acetic acid, water and n-hexane, and obtained compound 2 (3-((4-Chlorophenyl)thio)-2-hydroxyquinoline-4-carboxylic acid);
(2) a solution of compound 2 (3-((4-Chlorophenyl)thio)-2-hydroxyquinoline-4-carboxylic acid) in phosphoryl trichloride was heated at 150° C. for 48 h, after cooling the mixture was poured into water 0° C., the precipitate was collected by filtration, then added into 10% NaHCO$_3$ with vigorous stirring for 1 h, the resulting precipitate was collected and washed with H$_2$O, the crude solid was recrystallized by dichloromethane to give compound 3 (6,9-Dichloro-12H-thiochromeno[2,3-c]quinolin-12-one);
(3) a solution of compound 3 (6,9-Dichloro-12H-thiochromeno[2,3-c]quinolin-12-one) in DMF was added conc. HCl and refluxed, after 6 hours, the conc. HCl was added dropwise and refluxed for another 12 hours, the mixture was evaporated in vacuo and treated with H$_2$O, after filtered the crude solid was washed with EtOH to give compound 4 (10-Chloro-6-hydroxy-12H-thiochromeno[2,3-c]quinolin-12-one);
(4) a suspension of compound 3 (6,9-Dichloro-12H-thiochromeno[2,3-c]quinolin-12-one) and sodium methoxide in methanol was refluxed for 16 h, after cooled the solvent was removed, filtrated and washed with ethanol and n-hexane to collect compound 5 (10-Chloro-6-methoxy-12H-thiochromeno[2,3-c]quinolin-12-one);

(5) a solution of compound 3 (6,9-Dichloro-12H-thiochromeno[2,3-c]quinolin-12-one), appropriate secondary amines and sodium carbonate in DMSO was refluxed for 10 hours, then the reaction was added ice-water, the precipitate was filtered, washed with water/methanol and collected to get compound 6-21:
10-Chloro-6-dimethylamino-12H-thiochromeno[2,3-c]quinolin-12-one,
10-Chloro-6-(piperazin-1-yl)-12H-thiochromeno[2,3-c]quinolin-12-one,
10-Chloro-6-(4-methylpiperazin-1-yl)-12H-thiochromeno[2,3-c]quinolin-12-one,
10-Chloro-6-(4-ethylpiperazin-1-yl)-12H-thiochromeno[2,3-c]quinolin-12-one,
10-Chloro-6-(4-(2-hydroxyethyl)piperazin-1-yl)-12H-thiochromeno[2,3-c]quinolin-12one,
6-(4-Benzylpiperazin-1-yl)-10-chloro-12H-thiochromeno[2,3-c]quinolin-12-one,
10-Chloro-6-(4-phenylpiperazin-1-yl)-12H-thiochromeno[2,3-c]quinolin-12-one,
10-Chloro-6-morpholino-12H-thiochromeno[2,3-c]quinolin-12-one,
10-Chloro-6-thiomorpholino-12H-thiochromeno[2,3-c]quinolin-12-one,
10-Chloro-6-(piperidin-1-yl)-12H-thiochromeno[2,3-c]quinolin-12-one,
10-Chloro-6-(4-hydroxypiperidin-1-yl)-12H-thiochromeno[2,3-c]quinolin-12-one,
6-(4-Benzylpiperidin-1-yl)-10-chloro-12H-thiochromeno[2,3-c]quinolin-12-one,
6-([1,4'-Bipiperidin]-1'-yl)-10-chloro-12H-thiochromeno[2,3-c]quinolin-12-one,
10-Chloro-6-(4-(3-(piperidin-4-yl)propyl)piperidin-1-yl)-12H-thiochromeno[2,3-c]quinolin-12-one,
10-Chloro-6-(pyrrolidin-1-yl)-12H-thiochromeno[2,3-c]quinolin-12-one, and
10-Chloro-6-(2-oxopiperidin-1-yl)-12H-thiochromeno[2,3-c]quinolin-12-one respectively;
(6) a solution of compound 3 (6,9-Dichloro-12H-thiochromeno[2,3-c]quinolin-12-one) in DMSO was added appropriate primary amines and refluxed for 8 hours, after cooled the reaction was added water, the precipitate was filtered and washed with water and methanol to collect compound N1~N34:
10-Chloro-6-methylamino-12H-thiochromeno[2,3-c]quinolin-12-one,
10-Chloro-6-ethylamino-12H-thiochromeno[2,3-c]quinolin-12-one,
10-Chloro-6-propylamino-12H-thiochromeno[2,3-c]quinolin-12-one,
6-(Butylamino)-10-chloro-12H-thiochromeno[2,3-c]quinolin-12-one,
10-Chloro-6-isobutylamino-12H-thiochromeno[2,3-c]quinolin-12-one,
10-Chloro-6-(pentan-3-ylamino)-12H-thiochromeno[2,3-c]quinolin-12-one,
10-Chloro-6-((2-(dimethylamino)ethyl)amino)-12H-thiochromeno[2,3-c]quinolin-12-one,
10-Chloro-6-((2-(diethylamino)ethyl)amino)-12H-thiochromeno[2,3-c]quinolin-12-one,
10-Chloro-6-(2-ethanolamino)-12H-thiochromeno[2,3-c]quinolin-12-one,
10-Chloro-6-(3-propanolamino)-12H-thiochromeno[2,3-c]quinolin-12-one,
10-Chloro-6-(5-pentanolamino)-12H-thiochromeno[2,3-c]quinolin-12-one, 10-Chloro-6-((1-hydroxybutan-2-yl)amino)-12H-thiochromeno[2,3-c]quinolin-12-one,
10-Chloro-6-((4-methylpentan-2-yl)amino)-12H-thiochromeno[2,3-c]quinolin-12-one,
6-((2-Aminoethyl)amino)-10-chloro-12H-thiochromeno[2,3-c]quinolin-12-one,
10-Chloro-6-((2-((2-hydroxyethyl)amino)ethyl)amino)-12H-thiochromeno[2,3-c]quinolin-12-one,
10-Chloro-6-((2-morpholinoethyl)amino)-12H-thiochromeno[2,3-c]quinolin-12-one,
10-Chloro-6-((3-(dimethylamino)propyl)amino)-12H-thiochromeno[2,3-c]quinolin-12-one,
10-Chloro-6-((3-(diethylamino)propyl)amino)-12H-thiochromeno[2,3-c]quinolin-12-one,
10-Chloro-6-((3-((2-hydroxyethyl)amino)propyl)amino)-12H-thiochromeno[2,3-c]quinolin-12-one,
10-Chloro-6-((2,3-dihydro-1H-inden-2-yl)amino)-12H-thiochromeno[2,3-c]quinolin-12-one,
10-Chloro-6-(cyclohexylamino)-12H-thiochromeno[2,3-c]quinolin-12-one,
6-((1-Benzylpiperidin-4-yl)amino)-10-chloro-12H-thiochromeno[2,3-c]quinolin-12-one,
10-Chloro-6-((thiophen-2-ylmethyl)amino)-12H-thiochromeno[2,3-c]quinolin-12-one,
10-Chloro-6-((cyclohexylmethyl)amino)-12H-thiochromeno[2,3-c]quinolin-12-one,
6-(Benzylamino)-10-chloro-12H-thiochromeno[2,3-c]quinolin-12-one,
10-Chloro-6-((pyridin-2-ylmethyl)amino)-12H-thiochromeno[2,3-c]quinolin-12-one,
6-((Benzo[d][1,3]dioxol-5-ylmethyl)amino)-10-chloro-12H-thiochromeno[2,3-c]quinolin-12-one,
10-Chloro-6-((2-methoxybenzyl)amino)-12H-thiochromeno[2,3-c]quinolin-12-one,
10-Chloro-6-((3,4-dimethoxybenzyl)amino)-12H-thiochromeno[2,3-c]quinolin-12-one,
10-Chloro-6-(phenethylamino)-12H-thiochromeno[2,3-c]quinolin-12-one,
10-Chloro-6-((4-methoxyphenethyl)amino)-12H-thiochromeno[2,3-c]quinolin-12-one,
6-((4-Aminophenethyl)amino)-10-chloro-12H-thiochromeno[2,3-c]quinolin-12-one,
2-(10-Chloro-12-oxo-12H-thiochromeno[2,3-c]quinolin-6-yl)guanidine, and
10-Chloro-6-(piperidin-1-ylamino)-12H-thiochromeno[2,3-c]quinolin-12-one respectively.

* * * * *